United States Patent
Himmelsbach et al.

(10) Patent No.: US 6,924,285 B2
(45) Date of Patent: Aug. 2, 2005

(54) BICYCLIC HETEROCYCLIC COMPOUNDS, PHARMACEUTICAL COMPOSITIONS CONTAINING THESE COMPOUNDS, THEIR USE AND PROCESS FOR PREPARING THEM

(75) Inventors: Frank Himmelsbach, Mittelbiberach (DE); Birgit Jung, Laupheim (DE); Flavio Solca, Vienna (AT)

(73) Assignee: Boehringer Ingelheim Pharma GmbH & Co., Ingelheim (DE)

( * ) Notice: Subject to any disclaimer, the term of this patent is extended or adjusted under 35 U.S.C. 154(b) by 17 days.

(21) Appl. No.: 10/400,370

(22) Filed: Mar. 27, 2003

(65) Prior Publication Data

US 2004/0048880 A1 Mar. 11, 2004

Related U.S. Application Data

(60) Provisional application No. 60/381,176, filed on May 16, 2002.

(30) Foreign Application Priority Data

Mar. 30, 2002 (DE) .......................... 102 14 412
Jul. 13, 2002 (DE) .......................... 102 31 711

(51) Int. Cl.$^7$ .................. A61K 31/535; C07D 239/72
(52) U.S. Cl. .................. 514/234.8; 544/293; 544/283; 544/119; 544/111; 544/129; 544/147; 514/259; 514/235.2; 514/227.8; 514/252.14
(58) Field of Search ................ 544/283, 293, 544/119, 111, 129, 147; 514/234.8, 259, 252.14, 227.8, 235.2, 266.2, 266.4, 313; 548/284; 546/159

(56) References Cited

U.S. PATENT DOCUMENTS 5,747,498 A * 5/1998 Schnur et al. ........... 514/266.4
5,866,572 A * 2/1999 Barker et al. ............ 514/234.5
2002/0049197 A1   4/2002 Himmelsbach et al.
2002/0082271 A1   6/2002 Himmelsbach et al.

FOREIGN PATENT DOCUMENTS

WO   WO-0055141 A1   9/2000

* cited by examiner

Primary Examiner—Johann Richter
Assistant Examiner—Chukwuma Nwaonicha
(74) Attorney, Agent, or Firm—Michael P. Morris; Mary-Ellen M. Devlin; David A. Dow

(57) ABSTRACT

The present invention relates to bicyclic heterocyclic groups of general formula

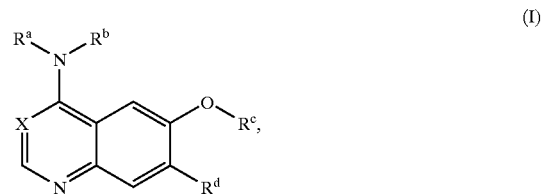

wherein $R^a$, $R^b$, $R^c$, $R^d$ and X are defined as in claim 1, the tautomers, the stereoisomers, the mixtures and the salts thereof, particularly the physiologically acceptable salts thereof with inorganic or organic acids which have valuable pharmacological properties, particularly an inhibitory effect on signal transduction mediated by tyrosine kinases, the use thereof for treating diseases, particularly tumoral diseases, as well as benign prostate hyperplasia (BPH), diseases of the lungs and respiratory tract, and the preparation thereof.

9 Claims, No Drawings

BICYCLIC HETEROCYCLIC COMPOUNDS, PHARMACEUTICAL COMPOSITIONS CONTAINING THESE COMPOUNDS, THEIR USE AND PROCESS FOR PREPARING THEM

RELATED APPLICATIONS

Benefit of U.S. Provisional Application Ser. No. 60/381,176 filed on May 16, 2002 is hereby claimed, and said Application is herein incorporated by reference.

FIELD OF INVENTION

This invention relates to bicyclic heterocyclic compounds active as inhibitors of signal transduction mediated by tyrosine kinases. The invention also relates to processes for preparing such compounds and pharmaceutical compositions comprising them.

BACKGROUND OF THE INVENTION

Inhibitors of signal transduction mediated by tyrosine kinases useful in the treatment of tumoral diseases as well as benign prostate hyperplasia (BPH) diseases of the lungs and respiratory tract. Tyrosine kinase inhibitors have been reported for the treatment of hyper-secretory respitory diseases. WO 00/10588.

SUMMARY AND DESCRIPTION OF THE INVENTION

The present invention relates to bicyclic heterocyclic groups of general formula

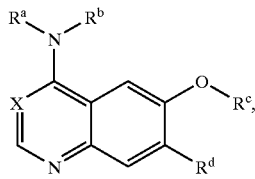

(I)

the tautomers, the stereoisomers, the mixtures and the salts thereof, particularly the physiologically acceptable salts thereof with inorganic or organic acids or bases which have valuable pharmacological properties, particularly an inhibitory effect on signal transduction mediated by tyrosine kinases, the use thereof for treating diseases, particularly tumoral diseases, as well as benign prostate hyperplasia (BPH), diseases of the lungs and respiratory tract, and the preparation thereof.

In the above general formula I $R^a$ denotes a hydrogen atom or a $C_{1-4}$-alkyl group, $R^b$ denotes a phenyl or 1-phenylethyl group, wherein the phenyl nucleus is substituted in each case by the groups $R^1$ to $R^3$, while $R^1$ and $R^2$, which may be identical or different, in each case denote a hydrogen, fluorine, chlorine, bromine or iodine atom, a $C_{1-4}$-alkyl, hydroxy, $C_{1-4}$-alkoxy, $C_{2-3}$-alkenyl or $C_{2-3}$-alkynyl group, an aryl, aryloxy, arylmethyl or arylmethoxy group, a heteroaryl, heteroaryloxy, heteroarylmethyl or heteroarylmethoxy group, a methyl or methoxy group substituted by 1 to 3 fluorine atoms or a cyano, nitro or amino group, and $R^3$ denotes a hydrogen, fluorine, chlorine or bromine atom or a methyl or trifluoromethyl group, $R^c$ denotes a cyclobutyl, cyclopentyl or cyclohexyl group which is substituted in each case by a group $R^4$—N—$R^5$, while $R^4$ denotes a hydrogen atom or a $C_{1-3}$-alkyl group and $R^5$ denotes a hydrogen atom or a $C_{1-3}$-alkyl group, an aminocarbonyl-$C_{1-3}$-alkyl, $C_{1-3}$-alkylaminocarbonyl-$C_{1-3}$-alkyl, di-($C_{1-3}$-alkyl)aminocarbonyl-$C_{1-3}$-alkyl, pyrrolidin-1-ylcarbonyl-$C_{1-3}$-alkyl, piperidin-1-ylcarbonyl-$C_{1-3}$-alkyl, homopiperidin-1-ylcarbonyl-$C_{1-3}$-alkyl, morpholin-4-ylcarbonyl-$C_{1-3}$-alkyl, homomorpholin-4-ylcarbonyl-$C_{1-3}$-alkyl, piperazin-1-ylcarbonyl-$C_{1-3}$-alkyl, 4-$C_{1-3}$-alkyl-piperazin-1-ylcarbonyl-$C_{1-3}$-alkyl, homopiperazin-1-ylcarbonyl-$C_{1-3}$-alkyl or a 4-$C_{1-3}$-alkyl-homopiperazin-1-ylcarbonyl-$C_{1-3}$-alkyl group, a hydroxy-$C_{2-4}$-alkyl, $C_{1-3}$-alkyloxy-$C_{2-4}$-alkyl, $C_{1-4}$-alkyloxy-carbonylamino-$C_{2-4}$-alkyl, amino-$C_{2-4}$-alkyl, $C_{1-3}$-alkylamino-$C_{2-4}$-alkyl, di-($C_{1-3}$-alkyl)amino-$C_{2-4}$-alkyl, $C_{1-3}$-alkylcarbonylamino-$C_{2-4}$-alkyl, aminocarbonylamino-$C_{2-4}$-alkyl, $C_{1-3}$-alkylaminocarbonylamino-$C_{2-4}$-alkyl, di-($C_{1-3}$-alkyl)amino-carbonylamino-$C_{2-4}$-alkyl, pyrrolidin-1-ylcarbonylamino-$C_{2-4}$-alkyl, piperidin-1-ylcarbonylamino-$C_{2-4}$-alkyl, morpholin-4-ylcarbonylamino-$C_{2-4}$-alkyl, $C_{1-3}$-alkylsulphonyl-$C_{2-4}$-alkyl or a $C_{1-3}$-alkylsulphonylamino-$C_{2-4}$-alkyl group, a (2-oxo-pyrrolidin-1-yl)-$C_{2-4}$-alkyl, (2-oxopiperidin-1-yl)-$C_{2-4}$-alkyl, (3-oxo-morpholin-4-yl)-$C_{2-4}$-alkyl, (2-oxo-imidazolidin-1-yl)-$C_{2-4}$-alkyl, (2-oxo-3-$C_{1-3}$-alkyl-imidazolidin-1-yl)-$C_{2-4}$-alkyl, (2-oxo-hexahydropyrimidin-1-yl)-$C_{2-4}$-alkyl or a (2-oxo-3-$C_{1-3}$-alkyl-hexahydropyrimidin-1-yl)-$C_{2-4}$-alkyl group, a $C_{1-4}$-alkylsulphonyl, chloro-$C_{1-4}$-alkylsulphonyl, bromo-$C_{1-4}$-alkylsulphonyl, amino-$C_{1-4}$-alkylsulphonyl, $C_{1-3}$-alkylamino-$C_{1-4}$-alkylsulphonyl, di-($C_{1-3}$-alkyl)amino-$C_{1-4}$-alkylsulphonyl, (pyrrolidin-1-yl)-$C_{1-4}$-alkylsulphonyl, (piperidin-1-yl)-$C_{1-4}$-alkylsulphonyl, (homopiperidin-1-yl)-$C_{1-4}$-alkylsulphonyl, (morpholin-4-yl)-$C_{1-4}$-alkylsulphonyl, (homomorpholin-4-yl)-$C_{1-4}$-alkylsulphonyl, (piperazin-1-yl)-$C_{1-4}$-alkylsulphonyl, (4-$C_{1-3}$-alkyl-piperazin-1-yl)-$C_{1-4}$-alkylsulphonyl, (homopiperazin-1-yl)-$C_{1-4}$-alkylsulphonyl or a (4-$C_{1-3}$-alkyl-homopiperazin-1-yl)-$C_{1-4}$-alkylsulphonyl group, a $C_{1-4}$-alkyloxycarbonyl group, a formyl, $C_{1-4}$-alkyl-carbonyl, $C_{1-3}$-alkyloxy-$C_{1-4}$-alkyl-carbonyl, tetrahydrofuranylcarbonyl, tetrahydropyranylcarbonyl, amino-$C_{1-4}$-alkyl-carbonyl, $C_{1-3}$-alkylamino-$C_{1-4}$-alkyl-carbonyl, di-($C_{1-3}$-alkyl)amino-$C_{1-4}$-alkyl-carbonyl, pyrrolidin-1-yl-$C_{1-4}$-alkyl-carbonyl, piperidin-1-yl-$C_{1-4}$-alkyl-carbonyl, (homopiperidin-1-yl)-$C_{1-4}$-alkyl-carbonyl, morpholin-4-yl-$C_{1-4}$-alkyl-carbonyl, (homomorpholin-4-yl)-$C_{1-4}$-alkyl-carbonyl, (piperazin-1-yl)-$C_{1-4}$-alkyl-carbonyl, (4-$C_{1-3}$-alkyl-piperazin-1-yl)-$C_{1-4}$-alkyl-carbonyl, (homopiperazin-1-yl)-$C_{1-4}$-alkyl-carbonyl, (4-$C_{1-3}$-alkyl-homopiperazin-1-yl)-$C_{1-4}$-alkyl-carbonyl or a $C_{1-3}$-alkylsulphonyl-$C_{1-4}$-alkyl-carbonyl group, a cyano, aminocarbonyl, $C_{1-3}$-alkyl-aminocarbonyl, di-($C_{1-3}$-alkyl)amino-carbonyl, ($C_{1-3}$-alkyloxy-$C_{2-4}$-alkyl)aminocarbonyl, N-($C_{1-3}$-alkyl)-N-($C_{1-3}$- alkyloxy-$C_{2-4}$-alkyl)aminocarbonyl, arylaminocarbonyl, pyrrolidin-1-ylcarbonyl, piperidin-1-ylcarbonyl, homopiperidin-1-ylcarbonyl, morpholin-4-ylcarbonyl, homomorpholin-4-ylcarbonyl, 2-oxa-5-aza-bicyclo[2.2.1]hept-5-ylcarbonyl, 3-oxa-8-aza-bicyclo[3.2.1]oct-8-ylcarbonyl, 8-oxa-3-aza-bicyclo[3.2.1]oct-3-ylcarbonyl, piperazin-1-ylcarbonyl, 4-$C_{1-3}$-alkyl-piperazin-1-ylcarbonyl, homopiperazin-1-ylcarbonyl, 4-$C_{1-3}$-alkyl-homopiperazin-1-ylcarbonyl, aminosulphonyl, $C_{1-3}$-alkyl-aminosulphonyl, di-($C_{1-3}$-alkyl)amino-sulphonyl, pyrrolidin-1-yl-sulphonyl, piperidin-1-ylsulphonyl, homopiperidin-1-ylsulphonyl, morpholin-4-ylsulphonyl, homomorpholin-4-ylsulphonyl, piperazin-1-ylsulphonyl, 4-$C_{1-3}$-alkyl-piperazin-1-ylsulphonyl, homopiperazin-1-ylsulphonyl or a 4-$C_{1-3}$-alkyl-homopiperazin-1-ylsulphonyl group, a cyclobutyl, cyclopentyl or cyclohexyl group which is substituted in each case by a group $R^6$, where $R^6$ denotes a 2-oxo-pyrrolidin-1-yl, 2-oxopiperidin-1-yl, 3-oxo-morpholin-4-yl, 2-oxo-imidazolidin-1-yl, 2-oxo-3-$C_{1-3}$-alkyl-imidazolidin-1-yl, 2-oxo-hexahydropyrimidin-1-yl or a 2-oxo-3-$C_{1-3}$-alkyl-hexahydropyrimidin-1-yl group, an azetidin-3-yl group which is substituted in the 1 position by the group $R^5$, while $R^5$ is as hereinbefore defined, a pyrrolidin-3-yl group which is substituted in the 1 position by the group $R^5$, while $R^5$ is as hereinbefore defined, a piperidin-3-yl group which is substituted in the 1 position by the group $R^5$, while $R^5$ is as hereinbefore defined, a piperidin-4-yl group which is substituted in the 1 position by the group $R^5$, while $R^5$ is as hereinbefore defined, or a tetrahydrofuran-3-yl, tetrahydropyran-3-yl or tetrahydropyran-4-yl group, $R^d$ denotes a hydrogen atom or a fluorine, chlorine or bromine atom, a hydroxy group, a $C_{1-4}$-alkyloxy group, a methoxy group substituted by 1 to 3 fluorine atoms, an ethyloxy group substituted by 1 to 5 fluorine atoms, a $C_{2-4}$-alkyloxy group which is substituted by a group $R^6$ or $R^7$, while $R^6$ is as hereinbefore defined and $R^7$ denotes a hydroxy, $C_{1-3}$-alkyloxy, $C_{3-6}$-cycloalkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, 2-oxa-5-aza-bicyclo[2.2.1]hept-5-yl, 3-oxa-8-aza-bicyclo[3.2.1]oct-8-yl, 8-oxa-3-aza-bicyclo[3.2.1]oct-3-yl, piperazin-1-yl, 4-$C_{1-3}$-alkyl-piperazin-1-yl, homopiperazin-1-yl or $C_{1-3}$-alkyl-homopiperazin-1-yl group, or a formylamino, $C_{1-4}$-alkylcarbonylamino, $C_{1-3}$-alkyloxy-$C_{1-3}$-alkyl-carbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, piperazin-1-ylcarbonylamino, 4-$C_{1-3}$-alkyl-piperazin-1-ylcarbonylamino, morpholin-4-ylcarbonylamino or a $C_{1-4}$-alkylsulphonylamino group, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a $C_{1-4}$-alkoxy group which is substituted by a pyrrolidinyl, piperidinyl or homopiperidinyl group substituted in the 1 position by the group $R^8$, while $R^8$ denotes a hydrogen atom or a $C_{1-3}$-alkyl group, or a $C_{1-4}$-alkoxy group which is substituted by a morpholinyl group substituted in the 4 position by the group $R^8$, while $R^8$ is as hereinbefore defined, and X denotes a methyne group substituted by a cyano group or a nitrogen atom, and by the aryl groups mentioned in the definition of the above groups is meant in each case a phenyl group which is mono- or disubstituted by $R^9$, while the substituents may be identical or different and $R^9$ denotes a hydrogen atom, a fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group, by the heteroaryl groups mentioned in the definition of the above groups is meant a pyridyl, pyridazinyl, pyrimidinyl or pyrazinyl group, while the abovementioned heteroaryl groups are each mono- or disubstituted by the group $R^9$, while the substituents may be identical or different and $R^9$ is as hereinbefore defined, and the abovementioned pyrrolidinyl, piperidinyl, piperazinyl and morpholinyl groups may be substituted in each case by one or two $C_{1-3}$-alkyl groups, and unless otherwise stated, the abovementioned alkyl groups may be straight-chained or branched, with the proviso that the compound 4-[(3-chloro-4-fluoro-phenyl)amino]-6-((S)-tetrahydrofuran-3-yloxy)-7-hydroxy-quinazoline is excluded.

Preferred compounds of the above general formula I are those wherein $R^a$ denotes a hydrogen atom, $R^b$ denotes a phenyl group substituted by the groups $R^1$ to $R^3$, while $R^1$ denotes a hydrogen, fluorine, chlorine or bromine atom, a methyl, trifluoromethyl or ethynyl group, a phenyloxy or phenylmethoxy group, while the phenyl moiety of the abovementioned groups is optionally substituted by a fluorine or chlorine atom, or a pyridyloxy or pyridinylmethoxy group, while the pyridinyl moiety of the abovementioned groups is optionally substituted by a methyl or trifluoromethyl group, $R^2$ denotes a hydrogen, fluorine or chlorine atom or a methyl group and $R^3$ denotes a hydrogen atom, $R^c$ denotes a cyclopentyl group which is substituted in the 3 position by a group $R^4$—N—$R^5$, while $R^4$ denotes a hydrogen atom or a $C_{1-3}$-alkyl group and $R^5$ denotes a hydrogen atom or a $C_{1-3}$-alkyl group, an aminocarbonyl-$C_{1-3}$-alkyl, $C_{1-3}$-alkylaminocarbonyl-$C_{1-3}$-alkyl, di-($C_{1-3}$-alkyl)aminocarbonyl-$C_{1-3}$-alkyl, pyrrolidin-1-ylcarbonyl-$C_{1-3}$-alkyl, piperidin-1-ylcarbonyl-$C_{1-3}$-alkyl, piperazin-1-ylcarbonyl-$C_{1-3}$-alkyl, 4-$C_{1-3}$-alkyl-piperazin-1-yl-carbonyl-$C_{1-3}$-alkyl or morpholin-4-ylcarbonyl-$C_{1-3}$-alkyl group, a hydroxy-$C_{2-4}$-alkyl, $C_{1-3}$-alkyloxy-$C_{2-4}$-alkyl, $C_{1-4}$-alkyloxy-carbonylamino-$C_{2-4}$-alkyl, amino-$C_{2-4}$-alkyl, $C_{1-3}$-alkylamino-$C_{2-4}$-alkyl, di-($C_{1-3}$-alkyl)amino-$C_{2-4}$-alkyl, $C_{1-3}$-alkylcarbonylamino-$C_{2-4}$-alkyl, aminocarbonylamino-$C_{2-4}$-alkyl, $C_{1-3}$-alkylaminocarbonylamino-$C_{2-4}$-alkyl, di-($C_{1-3}$-alkyl)amino-carbonylamino-$C_{2-4}$-alkyl, morpholin-4-ylcarbonylamino-$C_{2-4}$-alkyl, $C_{1-3}$-alkylsulphonyl-$C_{2-4}$-alkyl or $C_{1-3}$-alkylsulphonylamino-$C_{2-4}$-alkyl group, a (2-oxo-pyrrolidin-1-yl)-$C_{2-4}$-alkyl, (2-oxopiperidin-1-yl)-$C_{2-4}$-alkyl, (3-oxo-morpholin-4-yl)-$C_{2-4}$-alkyl, (2-oxo-imidazolidin-1-yl)-$C_{2-4}$-alkyl, (2-oxo-3-methyl-imidazolidin-1-yl)-$C_{2-4}$-alkyl, (2-oxo-hexahydropyrimidin-1-yl)-$C_{2-4}$-alkyl or (2-oxo-3-methyl-hexahydropyrimidin-1-yl)-$C_{2-4}$-alkyl group, a $C_{1-3}$-alkylsulphonyl, chloro-$C_{2-4}$-alkylsulphonyl, bromo-$C_{2-4}$-alkylsulphonyl, amino-$C_{2-4}$-alkylsulphonyl, $C_{1-3}$-alkylamino-$C_{2-4}$-alkylsulphonyl, di-($C_{1-3}$-alkyl)amino-$C_{2-4}$-alkylsulphonyl, (pyrrolidin-1-yl)-$C_{2-4}$-alkylsulphonyl, (piperidin-1-yl)-$C_{2-4}$-alkylsulphonyl or (morpholin-4-yl)-$C_{2-4}$-alkylsulphonyl group, a $C_{1-4}$-alkyloxy-carbonyl group, a formyl, $C_{1-3}$-alkyl-carbonyl, $C_{1-3}$-alkyloxy-$C_{1-3}$-alkyl-carbonyl, tetrahydrofuranylcarbonyl, tetrahydropyranylcarbonyl, amino-$C_{1-3}$-alkyl-carbonyl, $C_{1-3}$-alkylamino-$C_{1-3}$-alkyl-carbonyl, di-($C_{1-3}$-alkyl)amino-$C_{1-3}$-alkyl-carbonyl, pyrrolidin-1-yl-$C_{1-3}$-alkyl-carbonyl, piperidin-1-yl-$C_{1-3}$-alkyl-carbonyl, piperazin-1-yl-$C_{1-3}$-alkyl-carbonyl, 4-$C_{1-3}$-alkyl-piperazin-1-yl-$C_{1-3}$-alkyl-carbonyl, morpholin-4-yl-$C_{1-3}$-alkyl-carbonyl or a $C_{1-3}$-alkylsulphonyl-$C_{1-3}$-alkyl-carbonyl group, a cyano, aminocarbonyl, $C_{1-3}$-alkyl-aminocarbonyl, di-($C_{1-3}$-alkyl)amino-carbonyl, ($C_{1-3}$-alkyloxy-$C_{2-4}$-alkyl)aminocarbonyl, N-($C_{1-3}$-alkyl)-N-($C_{1-3}$-alkyloxy-$C_{2-4}$-alkyl)aminocarbonyl, phenylaminocarbonyl, pyrrolidin-1-ylcarbonyl, piperidin-1-ylcarbonyl, morpholin-4-ylcarbonyl, $C_{1-3}$-alkyl-morpholin-4-ylcarbonyl, di-($C_{1-3}$-alkyl)morpholin-4-ylcarbonyl, homomorpholin-4-ylcarbonyl, 2-oxa-5-aza-bicyclo[2.2.1]hept-5-ylcarbonyl, 3-oxa-8-aza-bicyclo[3.2.1]oct-8-ylcarbonyl, 8-oxa-3-aza-bicyclo[3.2.1]oct-3-ylcarbonyl, piperazin-1-ylcarbonyl, 4-($C_{1-3}$-alkyl)-piperazin-1-ylcarbonyl, aminosulphonyl, $C_{1-3}$-alkyl-aminosulphonyl, di-($C_{1-3}$-alkyl)amino-sulphonyl, pyrrolidin-1-yl-sulphonyl, piperidin-1-ylsulphonyl or a morpholin-4-ylsulphonyl group, or a cyclopentyl group which is substituted in the 3 position by a group $R^6$, while $R^6$ denotes a 2-oxo-pyrrolidin-1-yl, 2-oxopiperidin-1-yl, 3-oxo-morpholin-4-yl, 2-oxo-imidazolidin-1-yl, 2-oxo-3-methyl-imidazolidin-1-yl, 2-oxo-hexahydropyrimidin-1-yl or a 2-oxo-3-methyl-hexahydropyrimidin-1-yl group, a cyclohexyl group which is substituted in the 3 position or in the 4 position by a group $R^4$—N—$R^5$, while $R^4$ and $R^5$ are as hereinbefore defined, a cyclohexyl group which is substituted in the 3 position or in the 4 position by a group $R^6$, while $R^6$ is as hereinbefore defined, a pyrrolidin-3-yl group which is substituted in the 1 position by the group $R^5$, while $R^5$ is as hereinbefore defined, a piperidin-3-yl group which is substituted in the 1 position by the group $R^5$, while $R^5$ is as hereinbefore defined, a piperidin-4-yl group which is substituted in the 1 position by the group $R^5$, while $R^5$ is as hereinbefore defined, or a tetrahydrofuran-3-yl, tetrahydropyran-3-yl or tetrahydropyran-4-yl group, $R^d$ denotes a hydrogen atom, a $C_{1-3}$-alkyloxy group, a methoxy group which is substituted by one to three fluorine atoms, an ethyloxy group which is substituted in the 2 position by a group $R^6$ or $R^7$, while $R^6$ is as hereinbefore defined and $R^7$ denotes a hydroxy, $C_{1-3}$-alkyloxy, amino, $C_{1-3}$-alkylamino, di-($C_{1-3}$-alkyl)amino, bis-(2-methoxyethyl)-amino, pyrrolidin-1-yl, piperidin-1-yl, morpholin-4-yl, homomorpholin-4-yl, 2-oxa-5-azabicyclo[2.2.1]hept-5-yl, 3-oxa-8-aza-bicyclo[3.2.1]oct-8-yl, 8-oxa-3-aza-bicyclo[3.2.1]oct-3-yl, piperazin-1-yl or a 4-$C_{1-3}$-alkyl-piperazin-1-yl group, or a formylamino, $C_{1-4}$-alkylcarbonylamino, $C_{1-3}$-alkyloxy-$C_{1-3}$-alkyl-carbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, piperazin-1-ylcarbonylamino, 4-$C_{1-3}$-alkyl-piperazin-1-ylcarbonylamino-morpholin-4-ylcarbonylamino or a $C_{1-4}$-alkylsulphonylamino group, a propyloxy group which is substituted in the 3 position by a group $R^6$ or $R^7$, while $R^6$ and $R^7$ are as hereinbefore defined, or a butyloxy group which is substituted in the 4 position by a group $R^6$ or $R^7$, while $R^6$ and $R^7$ are as hereinbefore defined, and X denotes a nitrogen atom, while, unless stated otherwise, the abovementioned alkyl groups may be straight-chained or branched, their tautomers, their stereoisomers, their mixtures and their salts.

Particularly preferred compounds of the above general formula I are those wherein $R^a$ denotes a hydrogen atom, $R^b$ denotes a 3-ethynylphenyl, 3-bromophenyl, 3,4-difluorophenyl or 3-chloro-4-fluoro-phenyl group, a 3-chloro-4-benzyloxy-phenyl, 3-chloro-4-[(3-fluoro-benzyl)oxy]-phenyl, 4-(pyridin-3-yloxy)-phenyl, 4-[(6-methyl-pyridin-3-yl)oxy]-phenyl, 3-methyl-4-(pyridin-3-yloxy)-phenyl, 3-methyl-4-[(6-methyl-pyridin-3-yl)oxy]-phenyl, 3-chloro-4-(pyridin-3-yloxy)-phenyl or 3-chloro-4-[(6-methyl-pyridin-3-yl)oxy]-phenyl group, $R^c$ denotes a cyclohexyl group which is substituted in the 3 position or in the 4 position by a group $R^4$—N—$R^5$, while $R^4$ denotes a hydrogen atom, a methyl or ethyl group and $R^5$ denotes a hydrogen atom, a methyl, aminocarbonylmethyl, methylamino-carbonylmethyl, dimethylaminocarbonylmethyl, pyrrolidin-1-ylcarbonylmethyl, piperidin-1-ylcarbonylmethyl, piperazin-1-ylcarbonylmethyl, 4-methylpiperazin-1-ylcarbonylmethyl, morpholin-4-ylcarbonylmethyl, 2-(morpholin-4-yl-carbonyl)ethyl or 3-(morpholin-4-yl-carbonyl)propyl group, an ethyl, propyl, 2-hydroxyethyl, 3-hydroxypropyl, 2-methoxyethyl, 3-methoxypropyl, 2-(butyloxycarbonylamino)-ethyl, 2-aminoethyl, 3-aminopropyl, 2-(acetylamino)ethyl, 3-(acetylamino)propyl, 2-(ethylcarbonylamino)ethyl, 3-(ethylcarbonylamino)propyl, 2-(propylcarbonylamino)ethyl, 3-(propylcarbonylamino)propyl, 2-(ethylaminocarbonylamino)ethyl, 3-(ethylaminocarbonylamino)propyl, 2-(dimethylaminocarbonylamino)ethyl, 3-(dimethylaminocarbonylamino)propyl, 2-(morpholin-4-ylcarbonylamino)ethyl, 3-(morpholin-4-ylcarbonylamino)propyl, 2-(methylsulphonyl)ethyl, 3-(methylsulphonyl)propyl, 2-(methylsulphonylamino)ethyl or a 3-(methylsulphonylamino)propyl group, a 2-(2-oxo-pyrrolidin-1-yl)ethyl, 2-(2-oxopiperidin-1-yl)ethyl, 2-(3-oxo-morpholin-4-yl)ethyl, 2-(2-oxoimidazolidin-1-yl)ethyl, 2-(2-oxo-3-methyl-imidazolidin-1-yl)ethyl, 2-(2-oxo-hexahydropyrimidin-1-yl)ethyl or a 2-(2-oxo-3-methyl-hexahydropyrimidin-1-yl)ethyl group, a 3-(2-oxo-pyrrolidin-1-yl)propyl, 3-(2-oxopiperidin-1-yl)propyl, 3-(3-oxo-morpholin-4-yl)propyl, 3-(2-oxo-imidazolidin-1-yl)propyl, 3-(2-oxo-3-methyl-imidazolidin-1-yl)propyl, 3-(2-oxo-hexahydropyrimidin-1-yl)propyl or a 3-(2-oxo-3-methyl-hexahydropyrimidin-1-yl)propyl group, a methylsulphonyl, ethylsulphonyl, 3-chloropropylsulphonyl, 2-(morpholin-4-yl)-ethylsulphonyl or a 3-(morpholin-4-yl)-propylsulphonyl group, a propyloxycarbonyl or butyloxycarbonyl group, a formyl, acetyl, ethylcarbonyl, propylcarbonyl, methoxyacetyl, (2-methoxyethyl)carbonyl, (3-methoxypropyl)carbonyl, tetrahydrofuran-2-ylcarbonyl, tetrahydropyran-4-ylcarbonyl, aminoacetyl, methylaminoacetyl, dimethylaminoacetyl, morpholin-4-ylacetyl, [2-(morpholin-4-yl)ethyl]carbonyl, [3-(morpholin-4-yl)propyl]carbonyl or a methylsulphonylacetyl group, a cyano, aminocarbonyl, methylaminocarbonyl, dimethylaminocarbonyl, ethylaminocarbonyl, diethylaminocarbonyl, propylaminocarbonyl, (2-methoxyethyl)aminocarbonyl, N-methyl-N-(2-methoxyethyl)-aminocarbonyl, (3-methoxypropyl)aminocarbonyl, N-methyl-N-(3-methoxypropyl)-aminocarbonyl, phenylaminocarbonyl, pyrrolidin-1-ylcarbonyl, piperidin-1-ylcarbonyl, morpholin-4-ylcarbonyl, 2-methylmorpholin-4-ylcarbonyl, 2,6-dimethylmorpholin-4-ylcarbonyl, homomorpholin-4-ylcarbonyl, 2-oxa-5-aza-bicyclo[2.2.1]hept-5-ylcarbonyl, 3-oxa-8-aza-bicyclo[3.2.1]oct-8-ylcarbonyl, 8-oxa-3-aza-bicyclo[3.2.1]oct-3-ylcarbonyl, 4-methylpiperazin-1-ylcarbonyl, aminosulphonyl, methylaminosulphonyl, dimethylaminosulphonyl or a morpholin-4-ylsulphonyl group, a cyclohexyl group which is substituted in the 3 position or in the 4 position by a group $R^6$, while $R^6$ denotes a 2-oxo-pyrrolidin-1-yl, 2-oxopiperidin-1-yl, 3-oxo-morpholin-4-yl, 2-oxo-imidazolidin-1-yl, 2-oxo-3-methyl-imidazolidin-1-yl, 2-oxo-hexahydropyrimidin-1-yl or a 2-oxo-3-methyl-hexahydropyrimidin-1-yl group, a pyrrolidin-3-yl group which is substituted in the 1 position by the group $R^5$, while $R^5$ is as hereinbefore defined, a piperidin-3-yl group which is substituted in the 1 position by the group $R^5$, while $R^5$ is as hereinbefore defined, a piperidin-4-yl group which is substituted in the 1 position by the group $R^5$, while $R^5$ is as hereinbefore defined, a tetrahydrofuran-3-yl, tetrahydropyran-3-yl or tetrahydropyran-4-yl group, $R^d$ denotes a hydrogen atom, a methoxy, difluoromethoxy or ethyloxy group, an ethyloxy group which is substituted in the 2 position by a group $R^6$ or $R^7$, while $R^6$ is as hereinbefore defined and $R^7$ denotes a hydroxy, methoxy, ethoxy, amino, dimethylamino, diethylamino, bis-(2-methoxyethyl)-amino, pyrrolidin-1-yl, piperidin-1-yl, morpholin-4-yl, homomorpholin-4-yl, 2-oxa-5-aza-bicyclo[2.2.1]hept-5-yl, 3-oxa-8-aza-bicyclo[3.2.1]oct-8-yl, 8-oxa-3-aza-bicyclo[3.2.1]oct-3-yl, piperazin-1-yl, 4-methylpiperazin-1-yl or 4-ethylpiperazin-1-yl group, or an acetylamino, ethylcarbonylamino, propylcarbonylamino, butylcarbonylamino, methoxyacetylamino, butyloxycarbonylamino, ethylaminocarbonylamino, dimethylaminocarbonylamino, pyrrolidin-1-ylcarbonylamino, piperidin-1-ylcarbonylamino, morpholin-4-ylcarbonylamino, methylsulphonylamino, ethylsulphonylamino or butyl-sulphonylamino group, a propyloxy group which is substituted in the 3 position by a group $R^6$ or $R^7$, while $R^6$ and $R^7$ are as hereinbefore defined, or a butyloxy group which is substituted in the 4 position by a group $R^6$ or $R^7$, while $R^6$ and $R^7$ are as hereinbefore defined, and X denotes a nitrogen atom, while, unless stated otherwise, the abovementioned alkyl groups may be straight-chained or branched, their tautomers, their stereoisomers, their mixtures and their salts.

Most particularly preferred compounds of general formula I are those wherein $R^a$ denotes a hydrogen atom, $R^b$ denotes a 3-bromophenyl, 3,4-difluorophenyl, 3-chloro-4-fluoro-phenyl or a 3-ethynylphenyl group, or a 3-chloro-4-benzyloxy-phenyl, 3-chloro-4-[(3-fluorbenzyl)oxy]-phenyl, 4-(pyridin-3-yloxy)-phenyl, 4-[(6-methyl-pyridin-3-yl)oxy]-phenyl, 3-methyl-4-(pyridin-3-yloxy)-phenyl, 3-methyl-4-[(6-methyl-pyridin-3-yl)oxy]-phenyl, 3-chloro-4-(pyridin-3-yloxy)-phenyl or 3-chloro-4-[(6-methyl-pyridin-3-yl)oxy]-phenyl group, $R^c$ denotes a cyclohexyl group which is substituted in the 3 position by an amino, acetylamino, tert.-butyloxycarbonylamino or methylsulphonylamino group, a cyclohexyl group which is substituted in the 4 position by an amino, methylamino, ethylamino, dimethylamino, aminocarbonylmethylamino, methylaminocarbonylmethylamino, dimethylaminocarbonylmethylamino, morpholin-4-ylcarbonylmethylamino, [3-(morpholin-4-ylcarbonyl)propyl]amino, [2-(methylsulphonyl)ethyl]amino, [3-(methylsulphonyl)propyl]amino or [2-(methylsulphonylamino)ethyl]amino group, a cyclohexyl group which is substituted in the 4 position by a [2-(2-oxo-pyrrolidin-1-yl)ethyl]amino, [2-(2-oxopiperidin-1-yl)ethyl]amino, [2-(2-oxo-imidazolidin-1-yl)ethyl]amino, [2-(2-oxo-3-methyl-imidazolidin-1-yl)ethyl]amino, [2-(2-oxo-hexahydropyrimidin-1-yl)ethyl]amino or [2-(2-oxo-3-methyl-hexahydropyrimidin-1-yl)ethyl]amino group, a cyclohexyl group which is substituted in the 4 position by a [3-(2-oxo-pyrrolidin-1-yl)propyl]amino, [3-(2-oxopiperidin-1-yl)propyl]amino, [3-(2-oxo-imidazolidin-1-yl)propyl]amino, [3-(2-oxo-3-methyl-imidazolidin-1-yl)propyl]amino, [3-(2-oxo-hexahydropyrimidin-1-yl)propyl]amino or [3-(2-oxo-3-methyl-hexahydropyrimidin-1-yl)propyl]amino group, a cyclohexyl group which is substituted in the 4 position by an acetylamino, N-(acetyl)-methylamino, aminomethylcarbonylamino, methylaminomethylcarbonylamino, dimethylaminomethylcarbonylamino, morpholin-4-ylmethylcarbonylamino, methoxyacetylamino, N-(methoxyacetyl)-methylamino, tetrahydropyran-4-ylcarbonylamino, N-(tetrahydropyran-4-ylcarbonyl)-methylamino, tert.-butyloxycarbonylamino, N-(tert.-butyloxycarbonyl)-methylamino, aminocarbonylamino, methylaminocarbonylamino, N-(ethylaminocarbonyl)-methylamino, dimethylaminocarbonylamino, N-(dimethylaminocarbonyl)-methylamino, N-(piperidin-1-ylcarbonyl)-methylamino, morpholin-4-ylcarbonylamino, N-(morpholin-4-ylcarbonyl)-methylamino or N-(4-methylpiperazin-1-ylcarbonyl)-methylamino group, a cyclohexyl group which is substituted in the 4 position by a 2-oxo-pyrrolidin-1-yl, 2-oxopiperidin-1-yl, 3-oxo-morpholin-4-yl, 2-oxo-imidazolidin-1-yl, 2-oxo-3-methyl-imidazolidin-1-yl, 2-oxo-hexahydropyrimidin-1-yl or a 2-oxo-3-methyl-hexahydropyrimidin-1-yl group, a cyclohexyl group which is substituted in the 4 position by a methylsulphonylamino, N-(methylsulphonyl)-methylamino, ethylsulphonylamino, N-(ethylsulphonyl)-methylamino, dimethylaminosulphonylamino, N-(dimethylaminosulphonyl)-methylamino, morpholin-4-ylsulphonylamino, N-(morpholin-4-ylsulphonyl)-methylamino-3-chloropropylsulphonylamino, [2-(morpholin-4-yl)-ethyl]sulphonylamino or [3-(morpholin-4-yl)-propyl]sulphonylamino-group, a pyrrolidin-3-yl group, a pyrrolidin-3-yl group which is substituted in the 1 position by a methyl, acetyl, methoxyacetyl, tert.-butyloxycarbonyl, morpholin-4-ylcarbonyl or methylsulphonyl group, a piperidin-3-yl group, a piperidin-3-yl group which is substituted in the 1 position by a methyl, acetyl, methoxyacetyl, tert.-butyloxycarbonyl, morpholin-4-ylcarbonyl or methylsulphonyl group, a piperidin-4-yl group which is substituted in the 1 position by a methyl, ethyl, propyl, isopropyl, 2-hydroxyethyl, 2-methoxyethyl, 3-methoxypropyl, 2-(methylsulphonyl)-ethyl, 3-(methylsulphonyl)-propyl, 2-(tert.-butyloxycarbonylamino)-ethyl, 2-aminoethyl, 2-(acetylamino)-ethyl, 2-(ethylcarbonylamino)-ethyl, 2-(propylcarbonylamino)-ethyl, 2-(ethylaminocarbonylamino)-ethyl, 2-(dimethylaminocarbonylamino)-ethyl, 2-(morpholin-4-ylcarbonylamino)-ethyl, 3-(acetylamino)-propyl, 3-(ethylcarbonylamino)-propyl, 3-(propylcarbonylamino)-propyl, 3-(ethylaminocarbonylamino)-propyl, 3-(dimethylaminocarbonylamino)-propyl, 3-(morpholin-4-ylcarbonylamino)-propyl, 2-(methylsulphonylamino)-ethyl, 3-(methylsulphonylamino)-propyl, (aminocarbonyl)methyl, (methylaminocarbonyl)methyl, (dimethylaminocarbonyl)methyl, (pyrrolidin-1-ylcarbonyl)methyl, (morpholin-4-ylcarbonyl)methyl, 2-(morpholin-4-ylcarbonyl)-ethyl or 3-(morpholin-4-ylcarbonyl)-propyl group, a piperidin-4-yl group which is substituted in the 1 position by a 2-(2-oxo-pyrrolidin-1-yl)-ethyl, 2-(2-oxopiperidin-1-yl)-ethyl, 2-(3-oxomorpholin-4-yl)-ethyl, 2-(2-oxo-imidazolidin-1-yl)-ethyl, 2-(2-oxo-3-methyl-imidazolidin-1-yl)-ethyl, 2-(2-oxo-hexahydropyrimidin-1-yl)-ethyl or 2-(2-oxo-3-methyl-hexahydropyrimidin-1-yl)-ethyl group, a piperidin-4-yl group which is substituted in the 1 position by a 3-(2-oxo-pyrrolidin-1-yl)-propyl, 3-(2-oxopiperidin-1-yl)-propyl, 3-(3-oxomorpholin-4-yl)-propyl, 3-(2-oxo-imidazolidin-1-yl)-propyl, 3-(2-oxo-3-methyl-imidazolidin-1-yl)-propyl, 3-(2-oxo-hexahydropyrimidin-1-yl)-propyl or 3-(2-oxo-3-methyl-hexahydropyrimidin-1-yl)-propyl group, a piperidin-4-yl group which is substituted in the 1 position by a formyl, acetyl, methoxyacetyl, (2-methoxyethyl)carbonyl, (3-methoxypropyl)carbonyl, methylsulphonylacetyl, aminoacetyl, methylaminoacetyl, (dimethylamino)acetyl, (morpholin-4-yl)acetyl, [2-(morpholin-4-yl)-ethyl]carbonyl, [3-(morpholin-4-yl)-propyl]carbonyl, tetrahydrofuran-2-ylcarbonyl or tetrahydropyran-4-ylcarbonyl group, a piperidin-4-yl group which is substituted in the 1 position by a cyano, aminocarbonyl, methylaminocarbonyl, ethylaminocarbonyl, (2-methoxyethyl)aminocarbonyl, N-methyl-N-(2-methoxyethyl)-aminocarbonyl, (3-methoxypropyl)aminocarbonyl, N-methyl-N-(3-methoxypropyl)-aminocarbonyl, isopropylaminocarbonyl, phenylaminocarbonyl, dimethylaminocarbonyl, diethylaminocarbonyl, pyrrolidin-1-ylcarbonyl, piperidin-1-ylcarbonyl, morpholin-4-ylcarbonyl, 2-methylmorpholin-4-ylcarbonyl, 2,6-dimethylmorpholin-4-ylcarbonyl, homomorpholin-4-ylcarbonyl, 2-oxa-5-aza-bicyclo[2.2.1]hept-5-ylcarbonyl, 3-oxa-8-aza-bicyclo[3.2.1]oct-8-ylcarbonyl, 8-oxa-3-aza-bicyclo[3.2.1]oct-3-ylcarbonyl, 4-methylpiperazin-1-ylcarbonyl, isopropyloxycarbonyl or tert.-butyloxycarbonyl group, a piperidin-4-yl group which is substituted in the 1 position by a methylsulphonyl, ethylsulphonyl, [2-(morpholin-4-yl)-ethyl]sulphonyl, [3-(morpholin-4-yl)-propyl]sulphonyl, aminosulphonyl, methylaminosulphonyl, dimethylaminosulphonyl or morpholin-4-ylsulphonyl group, or a tetrahydrofuran-3-yl, tetrahydropyran-3-yl or tetrahydropyran-4-yl group, $R^d$ denotes a hydrogen atom, a methoxy, difluoromethoxy or ethyloxy group, a 2-(morpholin-4-yl)ethyloxy, 3-(morpholin-4-yl)propyloxy or 4-(morpholin-4-yl)butyloxy group, a 3-(dimethylamino)propyloxy, 3-(diethylamino)propyloxy, 3-[bis-(2-methoxyethyl)-amino]propyloxy, 3-(piperazin-1-yl)propyloxy, 3-(4-methylpiperazin-1-yl)propyloxy or 3-(4-ethylpiperazin-1-yl)propyloxy group, a 3-(homomorpholin-4-yl)-propyloxy, 3-(2-oxa-5-aza-bicyclo[2.2.1]hept-5-yl)-propyloxy, 3-(3-oxa-8-aza-bicyclo[3.2.1]oct-8-yl)-propyloxy or 3-(8-oxa-3-aza-bicyclo[3.2.1]oct-3-yl)-propyloxy group, a 2-(2-oxo-pyrrolidin-1-yl)-ethyloxy, 2-(2-oxopiperidin-1-yl)-ethyloxy, 2-(3-oxomorpholin-4-yl)-ethyloxy, 2-(2-oxo-imidazolidin-1-yl)-ethyloxy, 2-(2-oxo-3-methyl-imidazolidin-1-yl)-ethyloxy, 2-(2-oxo-hexahydropyrimidin-1-yl)-ethyloxy or 2-(2-oxo-3-methyl-hexahydropyrimidin-1-yl)-ethyloxy group, a 3-(2-oxo-pyrrolidin-1-yl)-propyloxy, 3-(2-oxopiperidin-1-yl)-propyloxy, 3-(3-oxomorpholin-4-yl)-propyloxy, 3-(2-oxo-imidazolidin-1-yl)-propyloxy, 3-(2-oxo-3-methyl-imidazolidin-1-yl)-propyloxy, 3-(2-oxo-hexahydropyrimidin-1-yl)-propyloxy or 3-(2-oxo-3-methyl-hexahydropyrimidin-1-yl)-propyloxy group, a 2-(methoxy)-ethyloxy, 2-(tert.-butyloxycarbonylamino)-ethyloxy, 2-(amino)-ethyloxy, 2-(acetylamino)-ethyloxy, 2-(ethylcarbonylamino)-ethyloxy, 2-(propylcarbonylamino)-ethyloxy, 2-(isobutylcarbonylamino)-ethyloxy, 2-(methoxyacetylamino)-ethyloxy, 2-(ethylaminocarbonylamino)-ethyloxy, 2-(dimethylaminocarbonylamino)-ethyloxy, 2-(pyrrolidin-1-ylcarbonylamino)-ethyloxy, 2-(piperidin-1-ylcarbonylamino)-ethyloxy, 2-(morpholin-4-ylcarbonylamino)-ethyloxy, 2-(methylsulphonylamino)-ethyloxy group, 2-(ethylsulphonylamino)-ethyloxy or 2-(butylsulphonylamino)-ethyloxy group, or a 3-(tert.-butyloxycarbonylamino)-propyloxy, 3-(amino)-propyloxy, 3-(acetylamino)-propyloxy or 3-(methylsulphonylamino)-propyloxy group,
and
X denotes a nitrogen atom,
their tautomers, their stereoisomers, their mixtures and their salts.

Particularly preferred compounds of general formula I are those wherein
$R^a$ denotes a hydrogen atom,
$R^b$ preferably denotes a 3-chloro-4-fluoro-phenyl group or also a 3-ethynylphenyl group,
$R^c$ denotes a cyclohexyl group which is substituted in the 3 position by an amino, acetylamino, tert.-butyloxycarbonylamino or methylsulphonylamino group,
a cyclohexyl group which is substituted in the 4 position by an amino, methylamino, dimethylamino, acetylamino, N-(acetyl)-methylamino, methoxyacetylamino, N-(methoxyacetyl)-methylamino, tetrahydropyran-4-ylcarbonylamino, N-(tetrahydropyran-4-ylcarbonyl)-methylamino, tert.-butyloxycarbonylamino, N-(tert.-butyloxycarbonyl)-methylamino, N-(ethylaminocarbonyl)-methylamino, dimethylaminocarbonylamino, N-(dimethylaminocarbonyl)-methylamino, N-(piperidin-1-ylcarbonyl)-methylamino, morpholin-4-ylcarbonylamino, N-(morpholin-4-ylcarbonyl)-methylamino, N-(4-methylpiperazin-1-ylcarbonyl)-methylamino, methylsulphonylamino, N-(methylsulphonyl)-methylamino, ethylsulphonylamino, N-(ethylsulphonyl)-methylamino, dimethylaminosulphonylamino, N-(dimethylaminosulphonyl)-methylamino, morpholin-4-ylsulphonylamino, N-(morpholin-4-ylsulphonyl)-methylamino, 3-chloropropylsulphonylamino, or [3-(morpholin-4-yl)-propyl]sulphonylamino group,
a pyrrolidin-3-yl group,
a pyrrolidin-3-yl group which is substituted in the 1 position by a tert.-butyloxycarbonyl or methylsulphonyl group,
a piperidin-3-yl group,
a piperidin-3-yl group which is substituted in the 1 position by a tert.-butyloxycarbonyl or methylsulphonyl group,
a piperidin-4-yl group,
a piperidin-4-yl group which is substituted in the 1 position by a methyl, (aminocarbonyl)methyl, (dimethylaminocarbonyl)methyl, (morpholin-4-ylcarbonyl)methyl, 2-(tert.-butyloxycarbonylamino)ethyl, 2-aminoethyl, 2-(acetylamino)ethyl, 2-(methylsulphonylamino)ethyl, cyano, acetyl, methoxyacetyl, (dimethylamino)acetyl, (morpholin-4-yl)acetyl, tetrahydropyran-4-ylcarbonyl, ethylaminocarbonyl, isopropylaminocarbonyl, phenylaminocarbonyl, dimethylaminocarbonyl, diethylaminocarbonyl, pyrrolidin-1-ylcarbonyl, piperidin-1-ylcarbonyl, morpholin-4-ylcarbonyl, 2-methylmorpholin-4-ylcarbonyl, 2,6-dimethylmorpholin-4-ylcarbonyl, homomorpholin-4-ylcarbonyl, 4-methylpiperazin-1-ylcarbonyl, isopropyloxycarbonyl, tert.-butyloxycarbonyl, methylsulphonyl, dimethylaminosulphonyl or morpholin-4-ylsulphonyl group, or
a tetrahydrofuran-3-yl, tetrahydropyran-3-yl or tetrahydropyran-4-yl group,
$R^d$ denotes a hydrogen atom,
a methoxy or ethyloxy group,
a 2-(morpholin-4-yl)ethyloxy, 3-(morpholin-4-yl)propyloxy or 4-(morpholin-4-yl)butyloxy group,
a 2-(3-methyl-2-oxo-hexahydropyrimidin-1-yl)-ethyloxy group,
a 2-(methoxy)-ethyloxy, 2-(tert.-butyloxycarbonylamino)-ethyloxy, 2-amino-ethyloxy, 2-(acetylamino)-ethyloxy or 2-(methylsulphonylamino)-ethyloxy group or
a 3-(tert.-butyloxycarbonylamino)-propyloxy, 3-amino-propyloxy, 3-(acetylamino)-propyloxy or 3-(methylsulphonylamino)-propyloxy group,
and
X denotes a nitrogen atom,
their tautomers, their stereoisomers, their mixtures and their salts.

Of the bicyclic heterocyclic groups of general formula I as described above as well as the sub-groups specified as being preferred, particularly preferred, most particularly preferred and especially preferred, special mention should be made of those compounds wherein
(a) $R^c$ denotes a cyclohexyl group substituted in the 4 position,
(b) $R^c$ denotes a pyrrolidin-3-yl group optionally substituted in the 1 position,
(c) $R^c$ denotes a piperidin-3-yl group optionally substituted in the 1 position,
(d) $R^c$ denotes a piperidin-4-yl group optionally substituted in the 1 position,
(e) $R^c$ denotes a tetrahydrofuran-3-yl group,
(f) $R^c$ denotes a tetrahydropyran-3-yl group, or
(g) $R^c$ denotes a tetrahydropyran-4-yl group,
while $R^a$, $R^b$, $R^d$ and X in each case are as hereinbefore defined.

The following are mentioned as examples of particularly preferred compounds of general formula I:
(1) 4-[(3-chloro-4-fluoro-phenyl)amino]-6-((S)-tetrahydrofuran-3-yloxy)-7-methoxy-quinazoline,
(2) 4-[(3-chloro-4-fluoro-phenyl)amino]-6-(tetrahydropyran-4-yloxy)-7-methoxy-quinazoline,
(3) 4-[(3-chloro-4-fluoro-phenyl)amino]-6-((R)-tetrahydrofuran-3-yloxy)-7-methoxy-quinazoline,
(4) 4-[(3-chloro-4-fluoro-phenyl)amino]-6-(trans-4-amino-cyclohexane-1-yloxy)-7-methoxy-quinazoline,
(5) 4-[(3-chloro-4-fluoro-phenyl)amino]-6-(trans-4-methanesulphonylamino-cyclohexane-1-yloxy)-7-methoxy-quinazoline,
(6) 4-[(3-chloro-4-fluoro-phenyl)amino]-6-(piperidin-4-yloxy)-7-methoxy-quinazoline,
(7) 4-[(3-chloro-4-fluoro-phenyl)amino]-6-(1-methanesulphonyl-piperidin-4-yloxy)-7-methoxy-quinazoline,
(8) 4-[(3-chloro-4-fluoro-phenyl)amino]-6-(cis-4-{[3-(morpholin-4-yl)-propyl]sulphonylamino}-cyclohexan-1-yloxy)-7-methoxy-quinazoline,
(9) 4-[(3-chloro-4-fluoro-phenyl)amino]-6-(tetrahydropyran-3-yloxy)-7-methoxy-quinazoline,
(10) 4-[(3-chloro-4-fluoro-phenyl)amino]-6-(trans-4-{[3-(morpholin-4-yl)-propyl]sulphonylamino}-cyclohexan-1-yloxy)-7-methoxy-quinazoline,
(11) 4-[(3-chloro-4-fluoro-phenyl)amino]-6-(1-methyl-piperidin-4-yloxy)-7-methoxy-quinazoline,
(12) 4-[(3-chloro-4-fluoro-phenyl)amino]-6-{1-[(morpholin-4-yl)carbonyl]-piperidin-4-yloxy}-7-methoxy-quinazoline,
(13) 4-[(3-chloro-4-fluoro-phenyl)amino]-6-{1-[(methoxymethyl)carbonyl]-piperidin-4-yloxy}-7-methoxy-quinazoline,
(14) 4-[(3-chloro-4-fluoro-phenyl)amino]-6-(1-cyano-piperidin-4-yloxy)-7-methoxy-quinazoline,

(15) 4-[(3-chloro-4-fluoro-phenyl)amino]-6-{1-[(morpholin-4-yl)sulphonyl]-piperidin-4-yloxy}-7-methoxy-quinazoline,

(16) 4-[(3-chloro-4-fluoro-phenyl)amino]-6-[1-(2-acetylamino-ethyl)-piperidin-4-yloxy]-7-methoxy-quinazoline,

(17) 4-[(3-chloro-4-fluoro-phenyl)amino]-6-{trans-4-[(dimethylamino)sulphonylamino]-cyclohexan-1-yloxy}-7-methoxy-quinazoline,

(18) 4-[(3-chloro-4-fluoro-phenyl)amino]-6-{trans-4-[(morpholin-4-yl)carbonylamino]-cyclohexan-1-yloxy}-7-methoxy-quinazoline,

(19) 4-[(3-chloro-4-fluoro-phenyl)amino]-6-{trans-4-[(morpholin-4-yl)sulphonylamino]-cyclohexan-1-yloxy}-7-methoxy-quinazoline,

(20) 4-[(3-chloro-4-fluoro-phenyl)amino]-6-(tetrahydropyran-4-yloxy)-7-(2-acetylamino-ethoxy)-quinazoline,

(21) 4-[(3-chloro-4-fluoro-phenyl)amino]-6-(tetrahydropyran-4-yloxy)-7-(2-methanesulphonylamino-ethoxy)-quinazoline and

(22) 4-[(3-chloro-4-fluoro-phenyl)amino]-6-(tetrahydropyran-4-yloxy)-7-(2-methoxy-ethoxy)-quinazoline, as well as their salts.

The compounds of general formula I may be prepared for example by the following methods:

a) reacting a compound of general formula

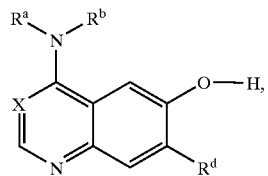

(II)

wherein $R^a$, $R^b$, $R^d$ and X are as hereinbefore defined, with a compound of general formula $$Z^1\text{-}R^c, \quad (III)$$

wherein $R^c$ is as hereinbefore defined and $Z^1$ denotes a leaving group such as a halogen atom, e.g. a chlorine or bromine atom, a sulphonyloxy group such as a methanesulphonyloxy or p-toluenesulphonyloxy group or a hydroxy group.

With a compound of general formula III wherein $Z^1$ denotes a hydroxy group, the reaction is carried out in the presence of a dehydrating agent, preferably in the presence of of a phosphine and an azodicarboxylic acid derivative such as e.g. triphenylphosphine/diethyl azodicarboxylate, conveniently in a solvent such as methylene chloride, acetonitrile, tetrahydrofuran, dioxane, toluene or ethyleneglycoldiethylether at temperatures between −50 and 150° C., but preferably at temperatures between −20 and 80° C.

b) In order to prepare compounds of general formula I wherein $R^d$ denotes one of the optionally substituted alkyloxy groups mentioned hereinbefore:

reacting a compound of general formula

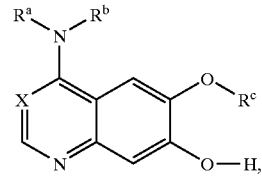

(IV)

wherein $R^a$, $R^b$, $R^c$ and X are as hereinbefore defined, with a compound of general formula $$Z^2\text{-}R^d, \quad (V)$$

wherein $R^d$ denotes a $C_{1-4}$-alkyl group, a methyl group substituted by 1 to 3 fluorine atoms, an ethyl group substituted by 1 to 5 fluorine atoms, a $C_{2-4}$-alkyl group substituted by a group $R^6$ or $R^7$, where $R^6$ and $R^7$ are as hereinbefore defined, a $C_{1-4}$-alkyl group which is substituted by a pyrrolidinyl, piperidinyl or homopiperidinyl group substituted in the 1 position by the group $R^8$, or a $C_{1-4}$-alkyl group which is substituted by a morpholinyl group substituted in the 4 position by the group $R^8$, while $R^8$ in each case is as hereinbefore defined, and $Z^2$ denotes a leaving group such as a halogen atom, an alkylsulphonyloxy, arylsulphonyloxy or a hydroxy group.

If the leaving group is a halogen atom such as a chlorine, bromine or iodine atom or an alkylsulphonyloxy or arylsulphonyloxy group such as the methanesulphonyloxy or p-toluenesulphonyloxy group, the reaction is preferably carried out in the presence of an organic or inorganic base such as potassium carbonate, sodium hydride or N-ethyldiisopropylamine. If the leaving group is a hydroxy group, the reaction is carried out in the presence of a dehydrating agent, preferably in the presence of a phosphine and an azodicarboxylic acid derivative such as e.g. triphenylphosphine/diethyl azodicarboxylate.

c) In order to prepare compounds of general formula I wherein $R^d$ denotes one of the abovementioned alkyloxy groups which is substituted by an optionally substituted amino, alkylamino or dialkylamino group or by an optionally substituted heterocyclic group bound via an imino-nitrogen atom:

reacting a compound of general formula

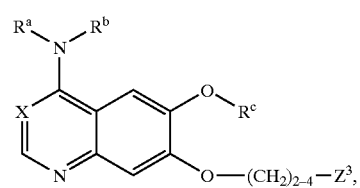

(VI)

wherein $R^a$, $R^b$, $R^c$ and X are as hereinbefore defined and $Z^3$ denotes a leaving group such as a halogen atom, e.g. a chlorine or bromine atom or a sulphonyloxy group such as a methanesulphonyloxy or p-toluenesulphonyloxy group, with ammonia, a corresponding, optionally substituted alkylamine, dialkylamine or an imino compound or the suitable salts or derivatives thereof, such as morpholine, for example.

d) In order to prepare compounds of general formula I wherein $R^d$ denotes a hydroxy group:

Cleaving a protecting group from a compound of general formula

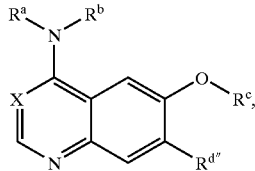

(VII)

wherein $R^a$, $R^b$, $R^c$ and X are as hereinbefore defined and $R^{d''}$ denotes a group which may be converted into a hydroxy group, for example an optionally substituted benzyloxy group, a trimethylsilyloxy, acetyloxy, benzoyloxy, methoxy, ethoxy, tert-butoxy or trityloxy group.

The protecting group is cleaved for example by hydrolysis in an aqueous solvent, e.g. in water, isopropanol/water, acetic acid/water, tetrahydrofuran/water or dioxan/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl or methoxybenzyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in tri-fluoroacetic acid in the presence of anisole.

A tert.butyl or benzyl group is cleaved for example by treating with an acid such as trifluoroacetic acid, hydrochloric acid or hydrobromic acid or by treating with iodotrimethylsilane, optionally using a solvent such as methylene chloride, dioxan, methanol or diethyl ether.

e) In order to prepare compounds of general formula I wherein $R^c$ contains a —NH— group:

cleaving a protecting group from a compound of general formula

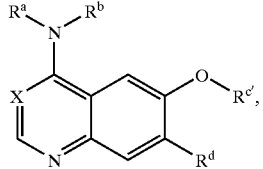

(VIII)

wherein $R^a$, $R^b$, $R^d$ and X are as hereinbefore defined and $R^c$ has the meanings given for $R^c$ hereinbefore, with the proviso that $R^c$ contains a protected nitrogen atom.

Conventional protecting groups for an amino, alkylamino or imino group are for example the formyl, acetyl, trifluoroacetyl, ethoxycarbonyl, tert.-butoxycarbonyl, benzyloxycarbonyl, benzyl, methoxybenzyl or 2,4-dimethoxybenzyl group, while for the amino group the phthalyl group is an additional possibility.

The protecting group is cleaved for example by hydrolysis in an aqueous solvent, e.g. in water, isopropanol/water, acetic acid/water, tetrahydrofuran/water or dioxan/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxan, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

f) In order to prepare compounds of general formula I wherein $R^c$ contains an alkyl group substituted by an optionally substituted amino, alkylamino or dialkyamino group or by an optionally substituted heterocyclic group bound via a nitrogen atom:

reacting a compound of general formula

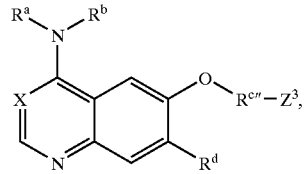

(IX)

wherein $R^a$, $R^b$, $R^d$ and X are as hereinbefore defined, $Z^3$ denotes a leaving group, for example a halogen atom such as a chlorine or bromine atom, or a sulphonyloxy group such as a methanesulphonyloxy or p-toluenesulphonyloxy group, and $R^c$ has the meanings given for $R^c$ hereinbefore with the proviso that a hydrogen atom bound to an aliphatic carbon atom is replaced by the group $Z^3$, with ammonia, a corresponding, optionally substituted alkylamine, dialkylamine or an imino compound or the appropriate salts or derivatives thereof, such as morpholine, for example.

If according to the invention a compound of general formula I is obtained which contains an amino, alkylamino or imino group, this may be converted by acylation, cyanation or sulphonylation into a corresponding acyl, cyano or sulphonyl compound of general formula I, the acylating agents being for example isocyanate, carbamoyl chloride, carboxylic acid halide, carboxylic acid anhydride and carboxylic acids with activating agents such as N,N'-carbonyldiimidazole, N,N'-dicyclohexylcarbodiimide or O-(benzotriazol-1-yl)-N,N,N'N'-tetramethyluronium-tetrafluoroborate, the sulphonylating agents being sulphonyl halides and the cyanating agents being chlorine or bromocyanogen, and/or if a compound of general formula I is obtained which contains an amino, alkylamino or imino group, this may be converted by alkylation or reductive alkylation into a corresponding alkyl compound of general formula I and/or if a compound of general formula I is obtained which contains a chloro-$C_{1-4}$-alkylsulphonyl or bromo-$C_{1-4}$-alkylsulphonyl group, this may be converted by reaction with an amine into a corresponding amino-$C_{1-4}$-alkylsulphonyl compound and/or if a compound of general formula I is obtained which contains a tert.-butyloxycarbonylamino, N-alkyl-N-(tert.-butyloxycarbonyl)amino or a N-tert.-butyloxycarbonylimino group, this may be converted into a corresponding amino, alkylamino or imino compound of general formula I by treatment with an acid such as hydrochloric acid or trifluoroacetic acid.

In the reactions described hereinbefore, any reactive groups present such as hydroxy, carboxy or imino groups may be protected during the reaction by conventional protecting groups which are cleaved again after the reaction.

For example, a protecting group for a hydroxy group may be a trimethylsilyl, acetyl, trityl, benzyl or tetrahydropyranyl group.

Protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group, for example.

Any protecting group used is optionally subsequently cleaved for example by hydrolysis in an aqueous solvent, e.g. in water, isopropanol/water, acetic acid/water, tetrahydrofuran/water or dioxan/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxan, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Al-linger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds of general formulae II to I used as starting materials are known from the literature in some cases or may be obtained by methods known from the literature (cf. Examples I to XXII) or the methods described hereinbefore, optionally with the additional use of protecting groups (e.g. compounds of formula IV or VII and VIII).

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself. It is also possible that the transmission of signals to components located further down is blocked.

The biological properties of the new compounds were investigated as follows:

The inhibition of human EGF-receptor kinase was determined using the cytoplasmic tyrosine kinase domain (methionine 664 to alanine 1186 based on the sequence published in Nature 309 (1984), 418). For this the protein was expressed in Sf9 insect cells as GST fusion protein using the Baculovirus expression system.

The enzyme activity was measured in the presence or absence of the test compounds in serial dilutions. The polymer pEY (4:1) obtained from SIGMA was used as the substrate. Biotinylated pEY (bio-pEY) was added as the tracer substrate. 100 μl of reaction solution contained 10 μl of the inhibitor in 50% DMSO, 20 μl of the substrate solution (200 mM HEPES pH 7.4, 50 mM magnesium acetate, 2.5 mg/ml poly(EY), 5 μg/ml bio-pEY) and 20 μl of enzyme preparation. The enzyme reaction was started by the addition of 50 μl of a 100 μM ATP solution in 10 mM of magnesium chloride. The dilution of the enzyme preparation was adjusted so that the incorporation of phosphate in the bio-pEY was linear in terms of time and quantity of enzyme. The enzyme preparation was diluted in 20 mM HEPES pH 7.4, 1 mM EDTA, 130 mM common salt, 0.05% Triton X-100, 1 mM DTT and 10% glycerol.

The enzyme assays were carried out at ambient temperature over a period of 30 minutes and ended by the addition of 50 μl of a stopping solution (250 mM EDTA in 20 mM HEPES pH 7.4). 100 μl were placed on a streptavidine-coated microtitre plate and incubated for 60 minutes at ambient temperature. Then the plate was washed with 200 μl of a wash solution (50 mM Tris, 0.05% Tween 20). After the addition of 100 μl of an HRPO-labelled anti-PY antibody (PY20H Anti-PTyr:HRP made by Transduction Laboratories, 250 ng/ml) the preparation was incubated for 60 minutes. Then the microtitre plate was washed three times with 200 μl of wash solution. The samples were then combined with 100 μl of a TMB-peroxidase solution (A:B= 1:1, Kirkegaard Perry Laboratories). After 10 minutes the reaction was stopped. The extinction was measured at $OD_{450\ nm}$ with an ELISA reader. All the results were measured three times.

The data were adapted by iterative calculation using an analytical pogramme for sigmoidal curves (Graph Pad Prism Version 3.0) with a variable Hill pitch. All the iterative data produced had a correlation coefficient of more than 0.9 and the upper and lower values of the curves showed a spread of at least a factor of 5. The active substance concentration which inhibits the activity of EGF receptor kinase by 50% ($IC_{50}$) was derived from the curves.

The following results were obtained:

| Compound (Example Nr.) | Inhibition of EGF receptor kinase $IC_{50}$ [nM] |
|---|---|
| 1 | 0.13 |
| 1(1) | 0.12 |
| 1(2) | 2 |
| 1(3) | 1.1 |
| 1(4) | 0.6 |
| 1(5) | 0.6 |
| 1(6) | 0.69 |
| 1(7) | 1.6 |
| 2 | 4.5 |
| 2(1) | 0.16 |
| 2(2) | 0.22 |
| 3 | 0.9 |
| 3(1) | 0.14 |
| 3(2) | 0.22 |
| 3(7) | 0.7 |
| 3(8) | 0.6 |
| 3(9) | 0.2 |

-continued

| Compound (Example Nr.) | Inhibition of EGF receptor kinase $IC_{50}$ [nM] |
|---|---|
| 3(11) | 0.1 |
| 3(15) | 1 |
| 3(16) | 1 |
| 3(17) | 0.3 |
| 3(18) | 0.4 |
| 3(20) | 1 |
| 3(21) | 0.4 |
| 4 | 0.41 |
| 4(1) | 0.16 |
| 7(5) | 1 |

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g. in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome.

In addition, the compounds of general formula I and the physiologically acceptable salts thereof may be used to treat other diseases caused by abnormal function of tyrosine kinases, such as e.g. epidermal hyperproliferation (psoriasis), benign prostate hyperplasia (BPH), inflammatory processes, diseases of the immune system, hyperproliferation of haematopoietic cells, the treatment of nasal polyps, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic (e.g. ambroxol, N-acetylcysteine), broncholytic (e.g. tiotropium or ipratropium or fenoterol, salmeterol, salbutamol) and/or anti-inflammatory activity (e.g. theophylline or glucocorticoids). For treating diseases in the region of the gastrointestinal tract, these compounds may also be administered on their own or in conjunction with substances having an effect on motility or secretion. These combinations may be administered either simultaneously or sequentially.

These compounds may be administered either on their own or in conjunction with other active substances by intravenous, subcutaneous, intramuscular, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:
Preparation of the Starting Compounds:

EXAMPLE I

4-[(3-chloro-4-fluoro-phenyl)amino]-6-(tetrahydropyran-4-yloxy)-7-benzyloxy-quinazoline-hydrochloride A mixture of 10.84 g 4-chloro-6-(tetrahydropyran-4-yloxy)-7-benzyloxy-quinazoline and 4.50 g 3-chloro-4-fluoranilin in 300 ml isopropanol is refluxed for four hours and then left to stand overnight at ambient temperature. The precipitate formed is suction filtered, washed with isopropanol and stirred with 150 ml of methanol. The suspension is stirred for another half hour at ambient temperature and then suction filtered. The filter cake is washed repeatedly with methanol and dried.

Yield: 9.07 g (60% of theory)

$R_f$ value: 0.27 (silica gel, cyclohexane/ethyl acetate=1:1)

Mass spectrum (ESI⁻): m/z=478, 480 [M–H]⁻

The following compounds are obtained analogously to Example I:
(1) 4-[(3-chloro-4-fluoro-phenyl)amino]-6-((S)-tetrahydrofuran-3-yloxy)-7-benzyloxy-quinazoline-hydrochloride
$R_f$ value: 0.34 (silica gel, cyclohexane/ethyl acetate=1:1)
Mass spectrum (ESI⁺): m/z=466, 468 [M+H]⁺
(2) 4-[(3-chloro-4-fluoro-phenyl)amino]-6-(1-trifluoroacetyl-piperidin-4-yloxy)-quinazoline-hydrochloride
$R_f$ value: 0.17 (Reversed phase ready-made TLC plate (E. Merck), acetonitrile/water/trifluoroacetic acid=50:50:1)
Mass spectrum (ESI⁺): m/z=469, 471 [M+H]⁺
(3) 4-[(3-chloro-4-fluoro-phenyl)amino]-6-(1-trifluoroacetyl-piperidin-4-yloxy)-7-acetoxy-quinazoline-hydrochloride
$R_f$ value: 0.70 (silica gel, methylene chloride/methanol/conc. aqueous ammonia=90:10:1)
Mass spectrum (ESI⁺): m/z=527, 529 [M+H]⁺
(4) 4-[(3-ethynyl-phenyl)amino]-6-acetoxy-7-methoxy-quinazoline
$R_f$ value: 0.59 (silica gel, ethyl acetate)
Mass spectrum (ESI⁺): m/z=334 [M+H]⁺
(5) 4-({3-chloro-4-[(3-fluorobenzyl)oxy]-phenyl}amino)-6-(acetyloxy)-7-methoxy-quinazoline
$R_f$ value: 0.20 (Reversed phase ready-made TLC plate (E. Merck), acetonitrile/water/trifluoroacetic acid=50:50:1)
Mass spectrum (ESI⁺): m/z=466, 468 [M+H]⁺
(6) 4-{[3-methyl-4-(pyridin-3-yloxy)-phenyl]amino}-6-(acetyloxy)-7-methoxy-quinazoline The 3-methyl-4-(pyridin-3-yloxy)-aniline used ($R_f$ value: 0.30 (silica gel, cyclohexane/ethyl acetate=1:1)) was prepared by reacting the sodium salt of 3-hydroxypyridine with 3-methyl-4-fluoro-nitrobenzene in dimethylformamide and subsequently hydrogenating the 3-methyl-4-(pyridin-3-yloxy)-nitrobenzene ($R_f$ value: 0.58 (silica gel, cyclohexane/ethyl acetate=1:1)) in the presence of palladium on activated charcoal.
$R_f$ value: 0.50 (Reversed phase ready-made TLC plate (E. Merck), acetonitrile/water/trifluoroacetic acid=50:50:1)
Mass spectrum (ESI⁺): m/z=415 [M–H]⁻

EXAMPLE II 4-chloro-6-(tetrahydropyran-4-yloxy)-7-benzyloxy-quinazoline

Prepared by reacting 6-(tetrahydropyran-4-yloxy)-7-benzyloxy-3H-quinazoline-4-on with thionyl chloride in the presence of N,N-dimethylformamide in acetonitrile at reflux temperature.

$R_f$ value: 0.90 (silica gel, ethyl acetate/methanol=9:1)

The following compounds are obtained analogously to Example II:
(1) 4-chloro-6-((S)-tetrahydrofuran-3-yloxy)-7-benzyloxy-quinazoline
$R_f$ value: 0.85 (silica gel, ethyl acetate/methanol=9:1)
(2) 4-chloro-6-(1-trifluoroacetyl-piperidin-4-yloxy)-quinazoline
$R_f$ value: 0.92 (silica gel, ethyl acetate)
(3) 4-chloro-6-(1-trifluoroacetyl-piperidin-4-yloxy)-7-acetoxy-quinazoline

EXAMPLE III 6-(tetrahydropyran-4-yloxy)-7-benzyloxy-3H-quinazoline-4-on

A mixture of 15.08 g 2-amino-4-benzyloxy-5-(tetrahydropyran-4-yloxy)-benzoic acid and 14.40 g formamidine acetate in 250 ml of absolute ethanol is refluxed overnight. The cooled reaction mixture is combined with 250 ml of water. The precipitate formed is suction filtered and dried at 70° C. in the drying cupboard.

Yield: 10.00 g (65% of theory)

$R_f$ value: 0.40 (Reversed phase ready-made TLC plate (E. Merck), acetonitrile/water/trifluoroacetic acid=50:50:1)

Mass spectrum (ESI⁺): m/z=353 [M+H]⁺

The following compounds are obtained analogously to Example III:
(1) 6-((S)-tetrahydrofuran-3-yloxy)-7-benzyloxy-3H-quinazoline-4-one
$R_f$ value: 0.60 (Reversed phase ready-made TLC plate (E. Merck), acetonitrile/water/trifluoroacetic acid=50:50:1)

Mass spectrum (ESI$^+$): m/z=339 [M+H]$^+$
(2) 6-[1-(tert.-butyloxycarbonyl)-piperidin-4-yloxy]-3H-quinazolin-4-one
R$_f$ value: 0.48 (silica gel, ethyl acetate/methanol=9:1)
Mass spectrum (ESI$^+$): m/z=346 [M+H]$^+$
(3) 6-[1-(tert.-butyloxycarbonyl)-piperidin-4-yloxy]-7-hydroxy-3H-quinazolin-4-one
R$_f$ value: 0.35 (silica gel, methylene chloride/methanol=9:1)
Mass spectrum (ESI$^+$): m/z=362 [M+H]$^+$

EXAMPLE IV 2-amino-4-benzyloxy-5-(tetrahydropyran-4-yloxy)-benzoic Acid 16.40 g 2-nitro-4-benzyloxy-5-(tetrahydropyran-4-yloxy)-benzoic acid are hydrogenated in the presence of 1.64 g Raney nickel in 800 ml of methanol at 55° C., until the calculated amount of hydrogen has been taken up. The catalyst is filtered off and the filtrate evaporated down, whereupon the desired product crystallises out.

Yield: 15.08 g (100% of theory)
R$_f$ value: 0.60 (Reversed phase ready-made TLC plate (E. Merck), acetonitrile/water/trifluoroacetic acid=50:50:1)

The following compounds are obtained analogously to Example IV:
(1) benzyl 2-amino-4-benzyloxy-5-((S)-tetrahydrofuran-3-yloxy)-benzoate
R$_f$ value: 0.70 (silica gel, cyclohexane/ethyl acetate=1:1)
Mass spectrum (ESI$^+$): m/z=420 [M+H]$^+$
(2) 2-amino-5-[1-(tert.-butyloxycarbonyl)-piperidin-4-yloxy]-benzoic acid
R$_f$ value: 0.43 (silica gel, methylene chloride/methanol=9:1)
Mass spectrum (ESI$^+$): m/z=337 [M+H]$^+$
(3) 2-amino-4-hydroxy-5-[1-(tert.-butyloxycarbonyl)-piperidin-4-yloxy]-benzoic acid
R$_f$ value: 0.23 (silica gel, methylene chloride/methanol/acetic acid=90:10:1)

EXAMPLE V 2-nitro-4-benzyloxy-5-(tetrahydropyran-4-yloxy)-benzoic Acid

Prepared by saponification of benzyl 2-nitro-4-benzyloxy-5-(tetrahydropyran-4-yloxy)-benzoate with 1 N sodium hydroxide solution in methanol at ambient temperature.

R$_f$ value: 0.20 (Reversed phase ready-made TLC plate (E. Merck), acetonitrile/water/trifluoroacetic acid=50:50:1)
Mass spectrum (ESI$^+$): m/z=374 [M+H]$^+$

EXAMPLE VI

Benzyl 2-nitro-4-benzyloxy-5-(tetrahydro-pyran-4-yloxy)-benzoate 42.60 g potassium-tert.-butoxide are added to 38 ml of tetrahydrofuran-4-ol in 228 ml N,N-dimethylformamide while cooling with an ice bath. The mixture is stirred for one hour at ambient temperature, then 22.90 g 6-nitro-benzo[1,3]dioxol-5-carboxylic acid are added. After 1.5 hours the reaction is complete according to thin layer chromatography and 28.94 ml of benzylbromide are added dropwise while cooling with an ice bath. The reaction mixture is stirred overnight at ambient temperature, combined with 100 ml 10% citric acid and stirred for another day at ambient temperature. Then the reaction mixture is evaporated down in vacuo at 60° C. and added to 800 ml ice water. The aqueous phase is extracted with ethyl acetate and the combined extracts are washed with water and saturated sodium chloride solution, dried over magnesium sulphate and evaporated.

The residue is stirred with diethyl ether, while 2-nitro-4-benzyloxy-5-(tetrahydropyran-4-yloxy)-benzoic acid crystallises out as a by-product. This is filtered off and the filtrate is evaporated down. The main product remaining is benzyl 2-nitro-4-benzyloxy-5-(tetrahydro-pyran-4-yloxy)-benzoate, which is saponified without any further purification to form carboxylic acid (see Example V).

The following compounds are obtained analogously to Example VI:
(1) benzyl 2-nitro-4-benzyloxy-5-((S)-tetrahydrofuran-3-yloxy)-benzoate
R$_f$ value: 0.75 (silica gel, cyclohexane/ethyl acetate=1:1)
Mass spectrum (ESI$^+$): m/z=450 [M+H]$^+$
(2) 2-nitro-4-hydroxy-5-[1-(tert.-butyloxycarbonyl)-piperidin-4-yloxy]-benzoic acid
No reaction is carried out with benzyl bromide.
R$_f$ value: 0.40 (silica gel, methylene chloride/methanol/acetic acid=90:10:1)
Mass spectrum (ESI$^-$): m/z=381 [M–H]$^-$

EXAMPLE VII

4-[(3-chloro-4-fluoro-phenyl)amino]-6-{1-[2-(tert.-butyloxycarbonylamino)-ethyl]-piperidin-4-yloxy}-7-methoxy-quinazoline A mixture of 410 mg 4-[(3-chloro-4-fluoro-phenyl)amino]-6-(piperidin-4-yloxy)-7-methoxy-quinazoline-dihydrochloride, 240 mg N-(tert.-butyloxycarbonyl)-2-bromo-ethylamine and 360 mg potassium carbonate in 5 ml N,N-dimethylformamide is stirred overnight at ambient temperature. Then a further 80 mg of N-(tert.-butyloxycarbonyl)-2-bromo-ethylamine are added and the reaction mixture is stirred for a further four hours at ambient temperature. For working up it is diluted with water and extracted with ethyl acetate. The combined organic phases are washed with saturated sodium chloride solution, dried over magnesium sulphate and evaporated. The residue is chromatographed through a silica gel column with ethyl acetate/methanol (95:5 to 90:1) as eluant.

Yield: 370 mg (79% of theory)
R$_f$ value: 0.33 (Reversed phase ready-made TLC plate (E. Merck), acetonitrile/water/trifluoroacetic acid=50:50:1)
Mass spectrum (ESI$^-$): m/z=544, 546 [M–H]$^-$ The following compound is obtained analogously to Example VII:
(1) 4-[(3-chloro-4-fluoro-phenyl)amino]-6-{1-[2-(tert.-butyloxycarbonylamino)-ethyl]-piperidin-4-yloxy}-quinazoline
R$_f$ value: 0.38 (Reversed phase ready-made TLC plate (E. Merck), acetonitrile/water/trifluoroacetic acid=50:50:1)
Mass spectrum (ESI$^+$): m/z=516, 518 [M+H]$^+$

EXAMPLE VIII

4-[(3-chloro-4-fluoro-phenyl)amino]-6-(piperidin-4-yloxy)-7-methoxy-quinazoline-dihydrochloride Prepared by treating 4-[(3-chloro-4-fluoro-phenyl)amino]-6-[1-(tert.-butyloxycarbonyl)-piperidin-4-yloxy]-7- methoxy-quinazoline with concentrated hydrochloric acid in dioxane at ambient temperature.

$R_f$ value: 0.53 (Reversed phase ready-made TLC plate (E. Merck), acetonitrile/water/trifluoroacetic acid=50:50:1)

Mass spectrum (ESI$^+$): m/z=403, 405 [M+H]$^+$

The following compounds are obtained analogously to Analog Example VII:

(1) 6-(piperidin-4-yloxy)-3H-quinazolin-4-one x 2 trifluoroacetic acid

Carried out with trifluoroacetic acid in methylene chloride.

Mass spectrum (ESI$^+$): m/z=246 [M+H]$^+$ (2) 6-(piperidin-4-yloxy)-7-hydroxy-3H-quinazolin-4-one Carried out with trifluoroacetic acid in methylene chloride.

$R_f$ value: 0.60 (Reversed phase ready-made TLC plate (E. Merck), acetonitrile/water/trifluoroacetic acid=50:50:1)

Mass spectrum (ESI$^+$): m/z=262 [M+H]$^+$

EXAMPLE IX

4-[(3-chloro-4-fluoro-phenyl)amino]-6-[1-(tert.-butyloxycarbonyl)-piperidin-4-yloxy]-7-methoxy-quinazoline A solution of 7.80 ml diethyl azodicarboxylate in 100 ml methylene chloride is added dropwise to a mixture of 10.00 g 4-[(3-chloro-4-fluoro-phenyl)amino]-6-hydroxy-7-methoxy-quinazoline and 9.40 g 1-(tert.-butyloxycarbonyl)-4-hydroxy-piperidine and 12.40 g triphenylphosphine in 400 ml methylene chloride at ambient temperature. The suspension is stirred for three days at ambient temperature and then suction filtered. The filtrate is evaporated and chromatographed through a silica gel column with methylene chloride/methanol (98:2 auf 95:5) as eluant. The crude product obtained is combined with diisopropylether, stirred overnight therein, suction filtered and dried.

Yield: 5.34 g (34% of theory)

$R_f$ value: 0.46 (silica gel, ethyl acetate/methanol=9:1)

Mass spectrum (ESI$^+$): m/z=503, 505 [M+H]$^+$

EXAMPLE X

4-[(3-chloro-4-fluoro-phenyl)amino]-6-(tetrahydropyran-4-yloxy)-7-(4-bromo-butyloxy)-quinazoline A mixture of 500 mg 4-[(3-chloro-4-fluoro-phenyl)amino]-6-(tetrahydropyran-4-yloxy)-7-hydroxy-quinazoline, 165 μl 1-bromo-4-chloro-propane and 360 mg potassium carbonate in 5 ml N,N-dimethylformamide is stirred overnight at 80° C. For working up the reaction mixture is diluted with water and extracted with ethyl acetate. The combined organic phases are washed with saturated sodium chloride solution, dried over magnesium sulphate and evaporated. The crude product is further reacted without any more purification.

Yield: 650 mg (97% of theory)

The following compounds are obtained analogously to Example X:

(1) 4-[(3-chloro-4-fluoro-phenyl)amino]-6-((S)-tetrahydrofuran-3-yloxy)-7-(4-bromo-butyloxy)-quinazoline $R_f$ value: 0.84 (silica gel, ethyl acetate/methanol=9:1)

(2) 4-[(3-chloro-4-fluoro-phenyl)amino]-6-(1-trifluoroacetyl-piperidin-4-yloxy)-7-ethoxy-quinazoline Mass spectrum (ESI$^+$): m/z=513, 515 [M+H]$^+$ (3) 4-[(3-chloro-4-fluoro-phenyl)amino]-6-(1-trifluoroacetyl-piperidin-4-yloxy)-7-(2-methoxy-ethoxy)-quinazoline $R_f$ value: 0.38 (silica gel, methylene chloride/methanol=9:1)

Mass spectrum (ESI$^+$): m/z=543, 545 [M+H]$^+$

EXAMPLE XI 1-(2-hydroxy-ethyl)-3-methyl-tetrahydropyrimidin-2-on

Prepared by hydrogenolytically cleaving 1-(2-benzyloxy-ethyl)-3-methyl-tetrahydropyrimidin-2-one in the presence of palladium on activated charcoal in methanol at ambient temperature.

$R_f$ value: 0.23 (silica gel, ethyl acetate/methanol/conc. aqueous ammonia=90:10:1)

Mass spectrum (ESI$^+$): m/z=159 [M+H]$^+$

EXAMPLE XII 1-(2-benzyloxy-ethyl)-3-methyl-tetrahydropyrimidin-2-on

Prepared by reacting 1-(2-benzyloxy-ethyl)-tetrahydropyrimidin-2-one with methyl iodide in the presence of potassium-tert.-butoxide in N,N-dimethylformamide at ambient temperature.

$R_f$ value: 0.62 (silica gel, ethyl acetate/methanol/conc. aqueous ammonia=90:10:1)

Mass spectrum (ESI$^+$): m/z=249 [M+H]$^+$

EXAMPLE XIII 1-(2-benzyloxy-ethyl)-tetrahydropyrimidin-2-on

Prepared by treating 1-(2-benzyloxy-ethyl)-3-(3-chloropropyl)-urea with potassium-tert.-butoxide in N,N-dimethylformamide at ambient temperature.

$R_f$ value: 0.42 (silica gel, ethyl acetate/methanol/conc. aqueous ammonia=90:10:1)

Mass spectrum (ESI$^+$): m/z=235 [M+H]$^+$

EXAMPLE XIV 1-(2-benzyloxy-ethyl)-tetrahydropyrimidin-2-one

Prepared by reacting 2-benzyloxy-ethylamine with 3-chloropropyl-isocyanate in tetrahydrofuran.

$R_f$ value: 0.73 (silica gel, ethyl acetate/methanol/conc. aqueous ammonia=90:10:1)

Mass spectrum (ESI$^+$): m/z=271, 273 [M+H]$^+$

EXAMPLE XV 3-(tert.-butyloxycarbonylamino)-cyclohexanol

Prepared by reacting 3-amino-cyclohexanol with di-tert.butyl pyrocarbonate in the presence of triethylamine in a mixture of dioxan/water (2:1) at 50° C.

$R_f$ value: 0.34 (silica gel, methylene chloride/methanol/conc. aqueous ammonia=90:10:1)

Mass spectrum (ESI$^-$): m/z=214 [M−H]$^-$

The following compounds are obtained analogously to Example XV:
(1) cis-4-[(N-(tert.-butyloxycarbonyl)-N-methyl-amino]-cyclohexanol
The reaction takes place in methanol.
$R_f$ value: 0.70 (silica gel, ethyl acetate)
Mass spectrum (ESI$^+$): m/z=230 [M+H]$^+$

EXAMPLE XVI 6-(1-trifluoroacetyl-piperidin-4-yloxy)-3H-quinazolin-4-one

Prepared by reacting 6-(piperidin-4-yloxy)-3H-quinazolin-4-one x 2 trifluoroacetic acid with trifluoroacetic acid anhydride in the presence of triethylamine in tetrahydrofuran.

$R_f$ value: 0.48 (silica gel, ethyl acetate/methanol=9:1)
Mass spectrum (ESI$^+$): m/z=342 [M+H]$^+$
The following compounds are obtained analogously to Example XVI:
(1) 6-(1-trifluoroacetyl-piperidin-4-yloxy)-7-hydroxy-3H-quinazolin-4-one
Carried out with methyl trifluoroacetate in the presence of Hünig base in methanol.
$R_f$ value: 0.80 (silica gel, methylene chloride/methanol=4:1)
Mass spectrum (ESI$^+$): m/z=358 [M+H]$^+$

EXAMPLE XVII 2-nitro-5-[1-(tert.-butyloxycarbonyl)-piperidin-4-yloxy]-benzoic Acid 21.00 g potassium-tert.-butoxide are added batchwise to 25.14 g 1-(tert.-butyloxycarbonyl)-piperidin-4-ol in 120 ml N,N-dimethylformamide while cooling with an ice bath, while the temperature is kept below 10° C. The mixture is stirred for a further 30 minutes while cooling with an ice bath, then 11.60 g of 5-fluoro-2-nitro-benzoic acid are added. After another three hours the reaction mixture is poured onto water, adjusted to pH 1 with conc. hydrochloric acid and extracted with ethyl acetate. The combined organic phases are washed with dilute citric acid solution, dried over magnesium sulphate and evaporated. The residue is triturated with diethyl ether, suction filtered and dried. More product crystallises out of the filtrate after standing for some time, and this is also suction filtered and dried.

Yield: 9.58 g (42% of theory)
$R_f$ value: 0.43 (silica gel, methylene chloride/methanol/acetic acid=90:10:1)
Mass spectrum (ESI$^+$): m/z=367[M+H]$^+$

EXAMPLE XVIII

4-[(3-chloro-4-fluoro-phenyl)amino]-6-(1-bromacetyl-piperidin-4-yloxy)-quinazoline and 4-[(3-chloro-4-fluoro-phenyl)amino]-6-(1-chloracetyl-piperidin-4-yloxy)-quinazoline Prepared by reacting 4-[(3-chloro-4-fluoro-phenyl) amino]-6-(piperidin-4-yloxy)-quinazoline with bromoacetic acid chloride in the presence of Honig base in tetrahydrofuran at ambient temperature. A mixture of the bromine and chlorine compounds is obtained.

$R_f$ value: 0.43 (silica gel, methylene chloride/methanol=9:1)
Mass spectrum (ESI$^+$): m/z=493, 495, 497 [M1+H]$^+$ and 449, 451, 453 [M2+H]$^+$ The following compounds are obtained analogously to Example XVIII:
(1) 4-[(3-chloro-4-fluoro-phenyl)amino]-6-(1-chloracetyl-piperidin-4-yloxy)-7-methoxy-quinazoline
The reaction takes place with chloroacetyl chloride.
$R_f$ value: 0.59 (silica gel, ethyl acetate/methanol/conc. aqueous ammonia=90:10:1)
Mass spectrum (ESI$^-$): m/z=477, 479, 481 [M−H]$^-$

EXAMPLE XIX 1-methyl-3-[([1,4]oxazepan-4-yl)carbonyl]-3H-imidazol-1-ium-iodide Prepared by reacting 3-[([1,4]oxazepan-4-yl)carbonyl]-3H-imidazole with methyl iodide in acetonitrile at ambient temperature. The crude product is reacted further without any more purification.

The following compounds are obtained analogously to Example XIX:
(1) 1-methyl-3-[(cis-2,6-dimethyl-morpholin-4-yl)carbonyl]-3H-imidazol-1-ium-iodide
$R_f$ value: 0.12 (silica gel, ethyl acetate/methanol/conc. aqueous ammonia=90:10:1)
(2) 1-methyl-3-[(2-methyl-morpholin-4-yl)carbonyl]-3H-imidazol-1-ium-iodide
$R_f$ value: 0.02 (silica gel, ethyl acetate/methanol/conc. aqueous ammonia=90:10:1)
(3) 1-methyl-3-[(S,S)-2-oxa-5-aza-bicyclo[2.2.1]hept-5-yl)carbonyl]-3H-imidazol-1-ium-iodide
$R_f$ value: 0.01 (silica gel, ethyl acetate/methanol/conc. aqueous ammonia=90:10:1)
(4) 1-methyl-3-[(N-methyl-N-2-methoxyethyl-amino)carbonyl]-3H-imidazol-1-ium-iodide
$R_f$ value: 0.03 (silica gel, ethyl acetate/methanol/conc. aqueous ammonia=90:10:1)
(5) 1-methyl-3-[(N-methyl-N-3-methoxypropyl-amino)carbonyl]-3H-imidazol-1-ium-iodide
$R_f$ value: 0.12 (silica gel, ethyl acetate/methanol/conc. aqueous ammonia=90:10:1)

EXAMPLE XX

3-[([1,4]oxazepan-4-yl)carbonyl]-3H-imidazole

Prepared by reacting [1,4]oxazepan with N,N'-carbonyldiimidazole in the presence of triethylamine in tetrahydrofuran at ambient temperature.

$R_f$ value: 0.30 (silica gel, ethyl acetate/methanol/conc. aqueous ammonia=90:10:1)
Mass spectrum (ESI$^+$): m/z=196 [M+H]$^+$
The following compounds are obtained analogously to Example XX:
(1) 3-[(cis-2,6-dimethyl-morpholin-4-yl)carbonyl]-3H-imidazole
$R_f$ value: 0.46 (silica gel, ethyl acetate/methanol/conc. aqueous ammonia=90:10:1)
(2) 3-[(2-methyl-morpholin-4-yl)carbonyl]-3H-imidazole
$R_f$ value: 0.43 (silica gel, ethyl acetate/methanol/conc. aqueous ammonia=90:10:1)
(3) 3-[(S, S)-(2-oxa-5-aza-bicyclo[2.2.1]hept-5-yl)carbonyl]-3H-imidazole
$R_f$ value: 0.59 (Reversed phase ready-made TLC plate (E. Merck), acetonitrile/water/trifluoroacetic acid=50:50:1)
(4) 3-[(N-methyl-N-2-methoxyethyl-amino)carbonyl]-3H-imidazole
$R_f$ value: 0.32 (silica gel, ethyl acetate/methanol/conc. aqueous ammonia=90:10:1)

(5) 3-[(N-methyl-N-3-methoxypropyl-amino)carbonyl]-3H-imidazole $R_f$ value: 0.36 (silica gel, ethyl acetate/methanol/conc. aqueous ammonia=90:10:1)

EXAMPLE XXI

4-[(3-chloro-4-fluoro-phenyl)amino]-6-(1-trifluoroacetyl-piperidin-4-yloxy)-7-hydroxy-quinazoline Prepared by treating 4-[(3-chloro-4-fluoro-phenyl)amino]-6-(1-trifluoroacetyl-piperidin-4-yloxy)-7-acetoxy-quinazoline-hydrochloride with saturated sodium hydrogen carbonate solution in methanol at ambient temperature. In addition to the desired product, some 4-[(3-chloro-4-fluoro-phenyl)amino]-6-(piperidin-4-yloxy)-7-hydroxy-quinazoline is also isolated as a by-product.

$R_f$ value: 0.20 (silica gel, methylene chloride/methanol=20:1)

Mass spectrum (ESI$^-$): m/z=483, 485 [M-H]$^-$

The following compounds are obtained analogously to Example XXI:

(1) 4-[(3-ethynyl-phenyl)amino]-6-hydroxy-7-methoxy-quinazoline

Carried out with 40% sodium hydroxide solution in ethanol.

$R_f$ value: 0.32 (silica gel, ethyl acetate)
Mass spectrum (ESI$^+$): m/z=292 [M+H]$^+$ (2) 4-({3-chloro-4-[(3-fluorobenzyl)oxy]-phenyl}amino)-6-hydroxy-7-methoxy-quinazoline $R_f$ value: 0.70 (silica gel, methylene chloride/methanol=9:1)

Mass spectrum (ESI$^-$): m/z=424, 426 [M-H]$^-$ (3) 4-{[3-methyl-4-(pyridin-3-yloxy)phenyl]amino}-6-hydroxy-7-methoxy-quinazoline $R_f$ value: 0.23 (silica gel, methylene chloride/methanol=9:1)

Mass spectrum (ESI$^-$): m/z=373 [M-H]$^-$

EXAMPLE XXII 6-(1-trifluoroacetyl-piperidin-4-yloxy)-7-acetoxy-3H-quinazolin-4-one Prepared by reacting 6-(1-trifluoroacetyl-piperidin-4-yloxy)-7-hydroxy-3H-quinazolin-4-one with acetic anhydride in pyridine at 80° C.

$R_f$ value: 0.60 (silica gel, methylene chloride/methanol=9:1)

Mass spectrum (ESI$^+$): m/z=400 [M+H]$^+$

EXAMPLE XXIII

4-[(3-Chloro-4-fluorophenyl)amino]-6-{1-[(4-nitrophenyloxy)-carbonyl]-piperidin-4-yloxy}-7-methoxy-quinazoline Prepared by reacting 4-[(3-chloro-4-fluorophenyl)amino]-6-(piperidin-4-yloxy)-7-methoxy-quinazoline (Example 2(2)) with (4-nitrophenyl) chloroformate.

$R_f$ value: 0.48 (silica gel, methylene chloride/methanol/conc. aqueous ammonia=90:10:1)

Preparation of the End Compounds:

EXAMPLE 1

4-[(3-chloro-4-fluoro-phenyl)amino]-6-((S)-tetrahydrofuran-3-yloxy)-7-methoxy-quinazoline

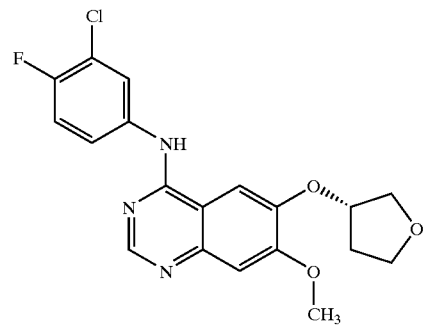

300 mg of 4-[(3-chloro-4-fluoro-phenyl)amino]-6-hydroxy-7-methoxy-quinazoline in 6 ml acetonitrile are combined with 114 μl (R)-3-hydroxy-tetrahydrofuran and 370 mg triphenylphosphine. Then 234 μl diethyl azodicarboxylate are added and the reaction mixture is stirred overnight at ambient temperature. For working up the reaction mixture is filtered and the filtrate evaporated down in vacuo. The crude product is purified by chromatography over a silica gel column with ethyl acetate/methanol (95:5) as eluant.

Yield: 53 mg (15% of theory)

melting point: 178° C.

Mass spectrum (ESI$^+$): m/z=390, 392 [M+H]$^+$

The following compounds are obtained analogously to Example 1:

(1) 4-[(3-chloro-4-fluoro-phenyl)amino]-6-(tetrahydropyran-4-yloxy)-7-methoxy-quinazoline

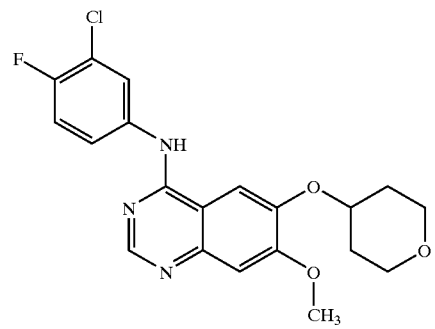

$R_f$ value: 0.54 (silica gel, ethyl acetate/methanol=9:1)
Mass spectrum (ESI$^+$): m/z=404, 406 [M+H]$^+$ (2) 4-[(3-chloro-4-fluoro-phenyl)amino]-6-[cis-4-(tert.-butyloxycarbonylamino)-cyclohexan-1-yloxy]-7-methoxy-quinazoline

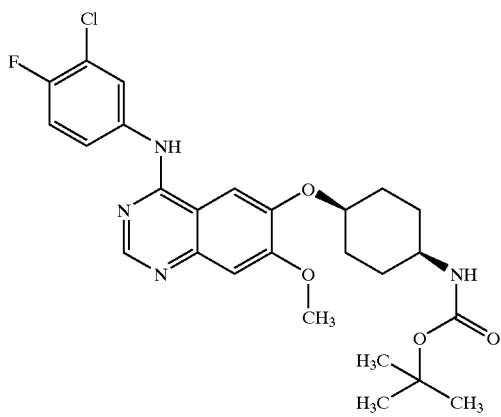

R$_f$ value: 0.70 (silica gel, ethyl acetate/methanol=9:1)
Mass spectrum (ESI$^+$): m/z=517, 519 [M+H]$^+$ (3) 4-[(3-chloro-4-fluoro-phenyl)amino]-6-((R)-tetrahydrofuran-3-yloxy)-7-methoxy-quinazoline

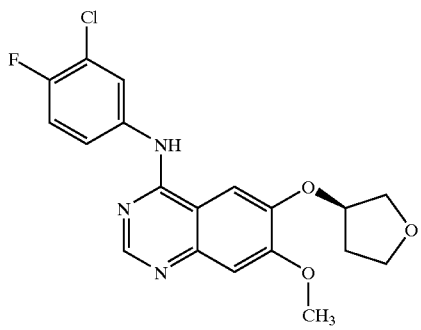

R$_f$ value: 0.64 (silica gel, ethyl acetate/methanol=9:1)
Mass spectrum (ESI$^+$): m/z=390, 392 [M+H]$^+$ (4) 4-[(3-chloro-4-fluoro-phenyl)amino]-6-[trans-4-(tert.-butyloxycarbonylamino)-cyclohexan-1-yloxy]-7-methoxy-quinazoline

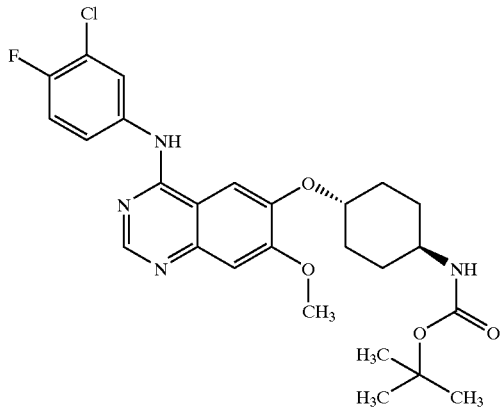

R$_f$ value: 0.65 (silica gel, ethyl acetate/methanol=9:1)
Mass spectrum (ESI$^+$): m/z=517, 519 [M+H]$^+$ (5) 4-[(3-chloro-4-fluoro-phenyl)amino]-6-[1-(tert.-butyloxycarbonyl)-piperidin-4-yloxy]-7-methoxy-quinazoline

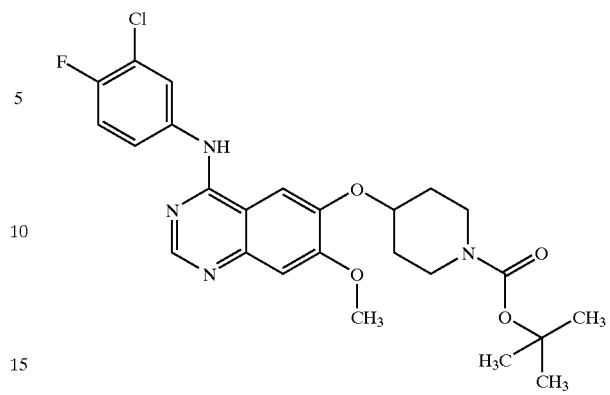

melting point: 184° C.
Mass spectrum (ESI$^+$): m/z=503, 505 [M+H]$^+$ (6) 4-[(3-chloro-4-fluoro-phenyl)amino]-6-(tetrahydropyran-3-yloxy)-7-methoxy-quinazoline

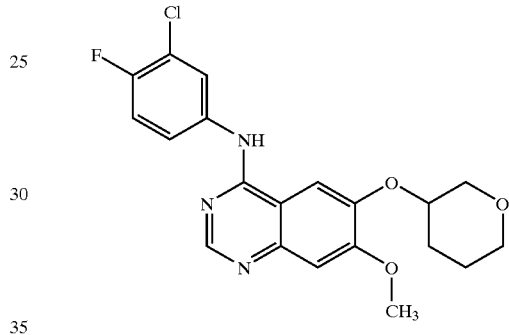

R$_f$ value: 0.52 (silica gel, methylene chloride/methanol=9:1)
Mass spectrum (ESI$^+$): m/z=404, 406 [M+H]$^+$ (7) 4-[(3-chloro-4-fluoro-phenyl)amino]-6-(1-methyl-piperidin-4-yloxy)-7-methoxy-quinazoline

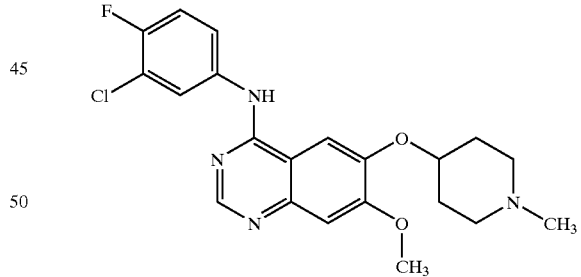

melting point: 218° C.
Mass spectrum (ESI$^+$): m/z=417, 419 [M+H]$^+$ (8) 4-[(3-chloro-4-fluoro-phenyl)amino]-6-[(S)-1-(tert.-butyloxycarbonyl)-pyrrolidin-3-yloxy]-7-methoxy-quinazoline Carried out with diisopropyl azodicarboxylate in methylene chloride.

R$_f$ value: 0.51 (silica gel, methylene chloride/methanol=9:1)
Mass spectrum (ESI$^+$): m/z=489, 491 [M+H]$^+$ (9) 4-[(3-chloro-4-fluoro-phenyl)amino]-6-[1-(tert.-butyloxycarbonyl)-piperidin-3-yloxy]-7-methoxy-quinazoline Carried out with diisopropyl azodicarboxylate in methylene chloride.

R$_f$ value: 0.56 (silica gel, methylene chloride/methanol= 9:1)

Mass spectrum (ESI$^-$): m/z=501, 503 [M−H]$^-$

(10) 4-[(3-chloro-4-fluoro-phenyl)amino]-6-((S)-tetrahydrofuran-3-yloxy)-7-[2-(3-methyl-2-oxo-hexahydropyrimidin-1-yl)-ethoxy]-quinazoline Carried out with diisopropyl azodicarboxylate in methylene chloride.

melting point: 235° C.

Mass spectrum (ESI$^+$): m/z=516, 518 [M+H]$^+$

(11) 4-[(3-chloro-4-fluoro-phenyl)amino]-6-[3-(tert.-butyloxycarbonylamino)-cyclohexan-1-yloxy]-7-methoxy-quinazoline Carried out with diisopropyl azodicarboxylate in methylene chloride.

R$_f$ value: 0.68 (silica gel, ethyl acetate/methanol=9:1)

Mass spectrum (ESI$^-$): m/z=515, 517 [M−H]$^-$

(12) 4-[(3-chloro-4-fluoro-phenyl)amino]-6-{cis-4-[N-(tert.-butyloxycarbonyl)-N-methyl-amino]-cyclohexan-1-yloxy}-7-methoxy-quinazoline Carried out with diisopropyl azodicarboxylate in methylene chloride.

R$_f$ value: 0.37 (silica gel, methylene chloride/methanol= 9:1)

Mass spectrum (ESI$^+$): m/z=531, 533 [M+H]$^+$

(13) 4-[(3-chloro-4-fluoro-phenyl)amino]-6-{trans-4-[N-(tert.-butyloxycarbonyl)-N-methyl-amino -cyclohexan-1-yloxy}-7-methoxy-quinazoline Carried out with diisopropyl azodicarboxylate in methylene chloride.

melting point: 231° C.

Mass spectrum (ESI$^+$): m/z=531, 533 [M+H]$^+$

EXAMPLE 2

4-[(3-chloro-4-fluoro-phenyl)amino]-6-(cis-4-amino-cyclohexan-1-yloxy)-7-methoxy-quinazoline x Trifluoroacetic Acid

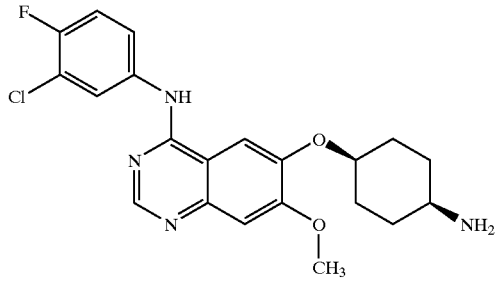

Prepared by treating 4-[(3-chloro-4-fluoro-phenyl)amino]-6-[cis-4-(tert.-butyloxycarbonylamino)-cyclohexan-1-yloxy]-7-methoxy-quinazoline with trifluoroacetic acid in methylene chloride at ambient temperature.

melting point: 221° C.

Mass spectrum (ESI$^+$): m/z=417, 419 [M+H]$^+$

The following compounds are obtained analogously to Example 2:

(1) 4-[(3-chloro-4-fluoro-phenyl)amino]-6-(trans-4-amino-cyclohexan-1-yloxy)-7-methoxy-quinazoline

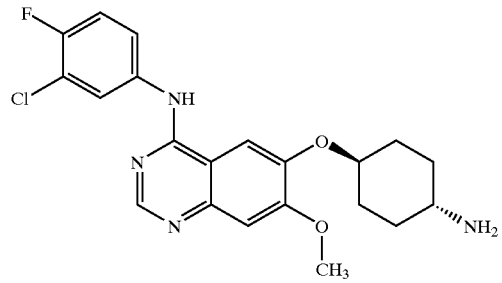

Mass spectrum (ESI$^+$): m/z=417, 419 [M+H]$^+$ (2) 4-[(3-chloro-4-fluoro-phenyl)amino]-6-(piperidin-4-yloxy)-7-methoxy-quinazoline x trifluoroacetic acid

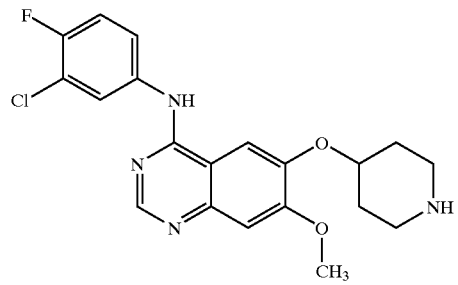

melting point: 232° C.

Mass spectrum (ESI$^+$): m/z=403, 405 [M+H]$^+$

EXAMPLE 3

4-[(3-chloro-4-fluoro-phenyl)amino]-6-(cis-4-methanesulphonylamino-cyclohexan-1-yloxy)-7-methoxy-quinazoline

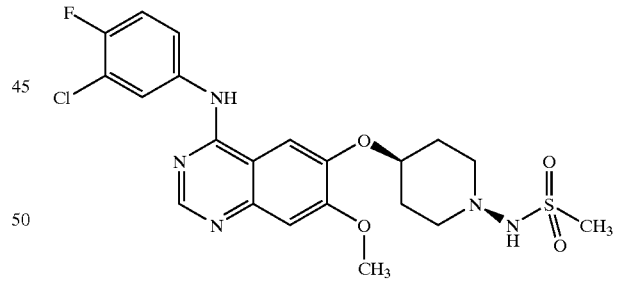

Prepared by reacting 4-[(3-chloro-4-fluoro-phenyl) amino]-6-(cis-4-amino-cyclohexan-1-yloxy)-7-methoxy-quinazoline x trifluoroacetic acid with methanesulphonic acid chloride in the presence of Hünig base in tetrahydrofuran at ambient temperature.

R$_f$ value: 0.77 (silica gel, ethyl acetate/methanol/conc. aqueous ammonia=40:10:1)

Mass spectrum (ESI$^+$): m/z=495, 497 [M+H]$^+$

The following compounds are obtained analogously to Example 3:

(1) 4-[(3-chloro-4-fluoro-phenyl)amino]-6-(trans-4-methanesulphonylamino-cyclohexan-1-yloxy)-7-methoxy-quinazoline

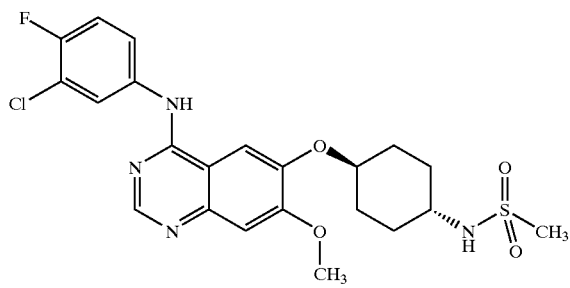

$R_f$ value: 0.20 (silica gel, ethyl acetate)

Mass spectrum (ESI⁺): m/z=495, 497 [M+H]⁺

(2) 4-[(3-chloro-4-fluoro-phenyl)amino]-6-(1-methanesulphonyl-piperidin-4-yloxy)-7-methoxy-quinazoline

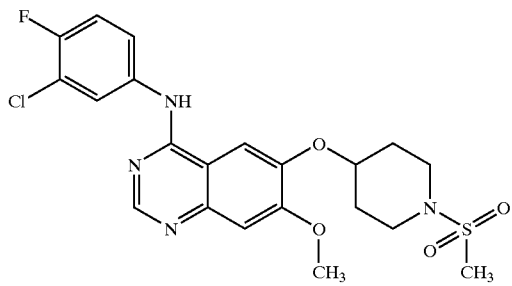

$R_f$ value: 0.59 (silica gel, ethyl acetate/methanol/conc. aqueous ammonia=90:10:1)

Mass spectrum (ESI⁺): m/z=481, 483 [M+H]⁺

(3) 4-[(3-chloro-4-fluoro-phenyl)amino]-6-{cis-4-[(3-chloropropyl)sulphonylamino]-cyclohexan-1-yloxy}-7-methoxy-quinazoline

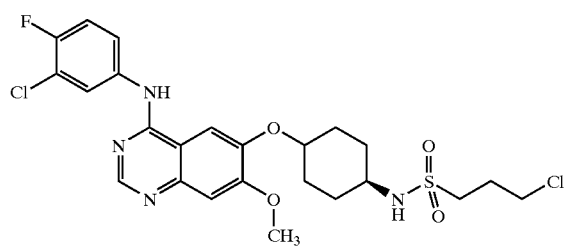

The reaction takes place with 3-chloropropansulphonyl chloride.

$R_f$ value: 0.79 (silica gel, ethyl acetate/methanol=9:1)

Mass spectrum (ESI⁻): m/z=555, 557, 559 [M−H]⁻

(4) 4-[(3-chloro-4-fluoro-phenyl)amino]-6-{trans-4-[(3-chloropropyl)sulphonylamino]-cyclohexan-1-yloxy}-7-methoxy-quinazoline

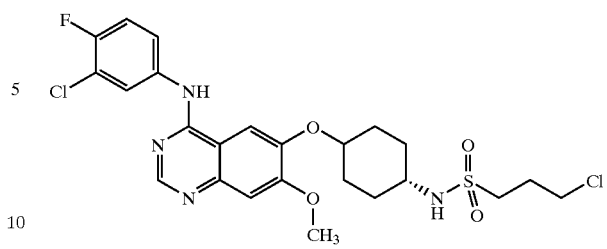

The reaction takes place with 3-chloropropanesulphonyl chloride.

$R_f$ value: 0.42 (silica gel, ethyl acetate)

Mass spectrum (ESI⁺): m/z=557, 559, 561 [M+H]⁺

(5) 4-[(3-chloro-4-fluoro-phenyl)amino]-6-(1-methylcarbonyl-piperidin-4-yloxy)-7-methoxy-quinazoline

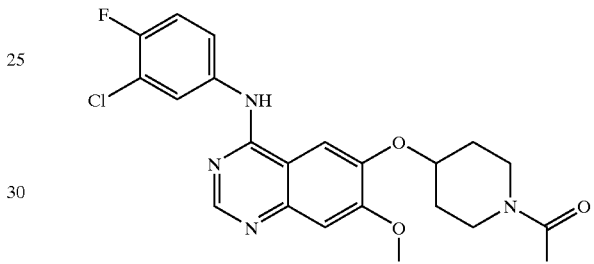

The reaction takes place with acetic anhydride.

melting point: 216° C.

Mass spectrum (ESI⁺): m/z=445, 447 [M+H]⁺

(6) 4-[(3-chloro-4-fluoro-phenyl)amino]-6-{1-[(dimethylamino)carbonyl]-piperidin-4-yloxy}-7-methoxy-quinazoline

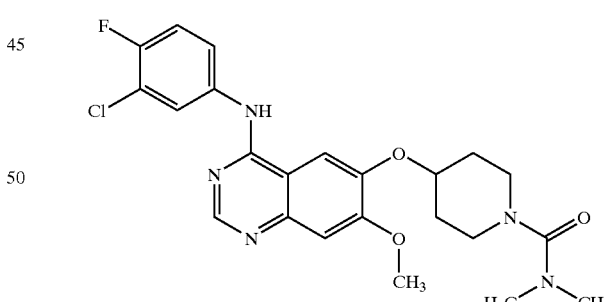

The reaction takes place with N,N-dimethylcarbamoylchloride.

$R_f$ value: 0.28 (Reversed phase ready-made TLC plate (E. Merck), acetonitrile/water/trifluoroacetic acid=50:50:1)

Mass spectrum (ESI⁺): m/z=474, 476 [M+H]⁺

(7) 4-[(3-chloro-4-fluoro-phenyl)amino]-6-{1-[(morpholin-4-yl)carbonyl]-piperidin-4-yloxy}-7-methoxy-quinazoline

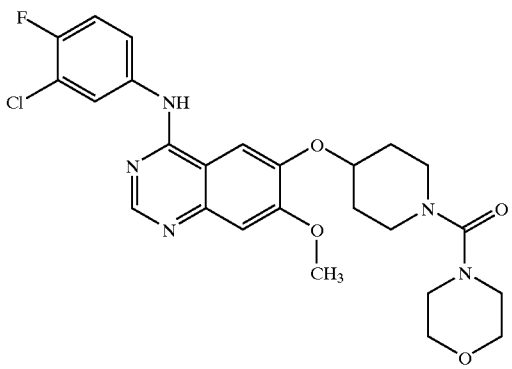

The reaction takes place with (morpholin-4-yl) carbonylchloride in acetonitrile.
$R_f$ value: 0.37 (Reversed phase ready-made TLC plate (E. Merck), acetonitrile/water/trifluoroacetic acid=50:50:1)
Mass spectrum (ESI$^+$): m/z=516, 518 [M+H]$^+$
(8) 4-[(3-chloro-4-fluoro-phenyl)amino]-6-{1-[(methoxymethyl)carbonyl]-piperidin-4-yloxy}-7-methoxy-quinazoline

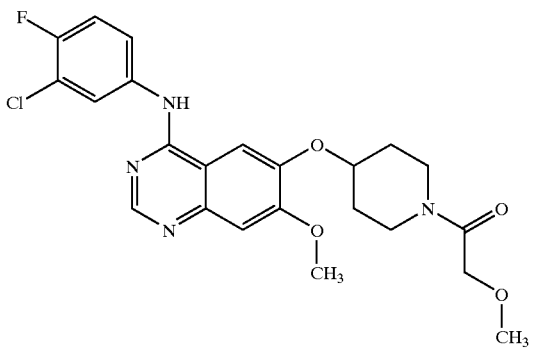

The reaction takes place with methoxyacetic acid chloride.
$R_f$ value: 0.80 (silica gel, methylene chloride/methanol=9:1)
Mass spectrum (ESI$^+$): m/z=475, 477 [M+H]$^+$
(9) 4-[(3-chloro-4-fluoro-phenyl)amino]-6-(1-cyano-piperidin-4-yloxy)-7-methoxy-quinazoline

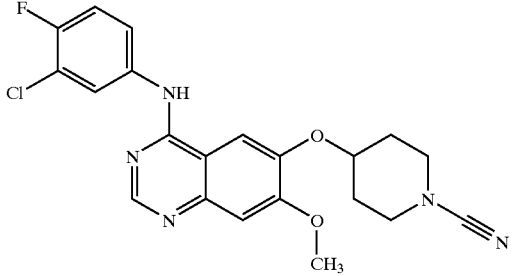

The reaction takes place with bromocyanogen in methylene chloride.
$R_f$ value: 0.40 (Reversed phase ready-made TLC plate (E. Merck), acetonitrile/water/trifluoroacetic acid=50:50:1)
Mass spectrum (ESI$^+$): m/z=428, 430 [M+H]$^+$
(10) 4-[(3-chloro-4-fluoro-phenyl)amino]-6-{1-[(dimethylamino)sulphonyl]-piperidin-4-yloxy}-7-methoxy-quinazoline

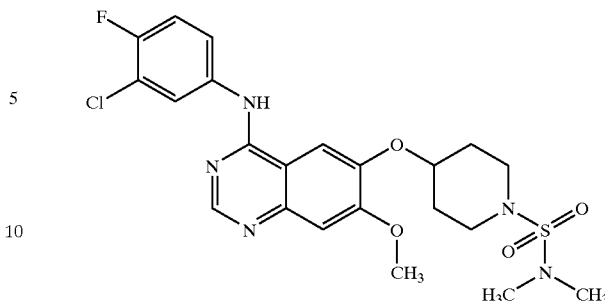

The reaction takes place with N,N-dimethylsulphamoylchloride in acetonitrile.
$R_f$ value: 0.24 (Reversed phase ready-made TLC plate (E. Merck), acetonitrile/water/trifluoroacetic acid=50:50:1)
Mass spectrum (ESI$^+$): m/z=510, 512 [M+H]$^+$
(11) 4-[(3-chloro-4-fluoro-phenyl)amino]-6-{1-[(morpholin-4-yl)sulphonyl]-piperidin-4-yloxy}-7-methoxy-quinazoline

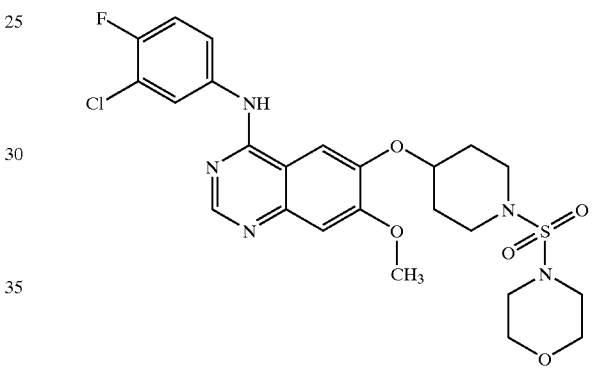

The reaction takes place with (morpholin-4-yl)sulphonyl chloride in acetonitrile.
$R_f$ value: 0.29 (Reversed phase ready-made TLC plate (E. Merck), acetonitrile/water/trifluoroacetic acid=50:50:1)
Mass spectrum (ESI$^+$): m/z=552, 554 [M+H]$^+$
(12) 4-[(3-chloro-4-fluoro-phenyl)amino]-6-(1-methanesulphonyl-piperidin-3-yloxy)-7-methoxy-quinazoline
$R_f$ value: 0.33 (Reversed phase ready-made TLC plate (E. Merck), acetonitrile/water/trifluoroaceticacid=50:50:1)
Mass spectrum (ESI$^+$): m/z=481, 483 [M+H]$^+$
(13) 4-[(3-chloro-4-fluoro-phenyl)amino]-6-((S)-1-methanesulphonyl-pyrrolidin-3-yloxy)-7-methoxy-quinazoline
melting point: 249° C.
Mass spectrum (ESI$^+$): m/z=467, 469 [M+H]$^+$
(14) 4-[(3-chloro-4-fluoro-phenyl)amino]-6-[1-(2-methanesulphonylamino-ethyl)-piperidin-4-yloxy]-7-methoxy-quinazoline
$R_f$ value: 0.49 (Reversed phase ready-made TLC plate (E. Merck), acetonitrile/water/trifluoroacetic acid=50:50:1)
Mass spectrum (ESI$^+$): m/z=524, 526 [M+H]$^+$
(15) 4-[(3-chloro-4-fluoro-phenyl)amino]-6-[1-(2-acetylamino-ethyl)-piperidin-4-yloxy]-7-methoxy-quinazoline The reaction takes place with acetic anhydride.
R$_f$ value: 0.51 (Reversed phase ready-made TLC plate (E. Merck), acetonitrile/water/trifluoroacetic acid=50:50:1)
Mass spectrum (ESI$^+$): m/z=488, 490 [M+H]$^+$

(16) 4-[(3-chloro-4-fluoro-phenyl)amino]-6-{trans-4-[(dimethylamino)sulphonylamino]-cyclohexan-1-yloxy}-7-methoxy-quinazoline The reaction takes place with N,N-dimethylsulphamoylchloride in acetonitrile.
R$_f$ value: 0.69 (silica gel, ethyl acetate/methanol/conc. aqueous ammonia=90:10:1)
Mass spectrum (ESI$^+$): m/z=524, 526 [M+H]$^+$

(17) 4-[(3-chloro-4-fluoro-phenyl)amino]-6-{trans-4-[(morpholin-4-yl)carbonylamino]-cyclohexan-1-yloxy}-7-methoxy-quinazoline The reaction takes place with (morpholin-4-yl)carbonylchloride in acetonitrile.
R$_f$ value: 0.38 (silica gel, ethyl acetate/methanol=9:1)
Mass spectrum (ESI$^+$): m/z=530, 532 [M+H]$^+$

(18) 4-[(3-chloro-4-fluoro-phenyl)amino]-6-{trans-4-[(morpholin-4-yl)sulphonylamino]-cyclohexan-1-yloxy}-7-methoxy-quinazoline The reaction takes place with (morpholin-4-yl)sulphonyl chloride in acetonitrile.
melting point: 237° C.
Mass spectrum (ESI$^-$): m/z=564, 566 [M-H]$^-$

(19) 4-[(3-chloro-4-fluoro-phenyl)amino]-6-(3-methanesulphonylamino-cyclohexan-1-yloxy)-7-methoxy-quinazoline
R$_f$ value: 0.66 (silica gel, ethyl acetate/methanol=9:1)
Mass spectrum (ESI$^-$): m/z=493, 495 [M-H]$^-$

(20) 4-[(3-chloro-4-fluoro-phenyl)amino]-6-(tetrahydropyran-4-yloxy)-7-(2-acetylamino-ethoxy)-quinazoline The reaction takes place with acetylchloride in acetonitrile.
melting point: 224° C.
Mass spectrum (ESI$^+$): m/z=475, 477 [M+H]$^+$

(21) 4-[(3-chloro-4-fluoro-phenyl)amino]-6-(tetrahydropyran-4-yloxy)-7-(2-methanesulphonylamino-ethoxy)-quinazoline
melting point: 227° C.
Mass spectrum (ESI$^+$): m/z=511, 513 [M+H]$^+$

(22) 4-[(3-chloro-4-fluoro-phenyl)amino]-6-(cis-3-acetylamino-cyclohexan-1-yloxy)-7-methoxy-quinazoline The reaction takes place with acetylchloride in acetonitrile. Cis- and trans-isomer are separated by chromatography over a silica gel column.
R$_f$ value: 0.43 (silica gel, methylene chloride/methanol/conc. aqueous ammonia=90:10:1)
Mass spectrum (ESI$^+$): m/z=459, 461 [M+H]$^+$

(23) 4-[(3-chloro-4-fluoro-phenyl)amino]-6-(trans-3-acetylamino-cyclohexan-1-yloxy)-7-methoxy-quinazoline The reaction takes place with acetylchloride in acetonitrile. Cis- and trans-isomer are separated by chromatography over a silica gel column.
R$_f$ value: 0.49 (silica gel, methylene chloride/methanol/conc. aqueous ammonia=90:10:1)
Mass spectrum (ESI$^+$): m/z=459, 461 [M+H]$^+$

(24) 4-[(3-chloro-4-fluoro-phenyl)amino]-6-(tetrahydropyran-4-yloxy)-7-(3-acetylamino-propyloxy)-quinazoline The reaction takes place with acetylchloride.
melting point: 225° C.
Mass spectrum (ESI$^+$): m/z=489, 491 [M+H]$^+$

(25) 4-[(3-chloro-4-fluoro-phenyl)amino]-6-(tetrahydropyran-4-yloxy)-7-(3-methanesulphonylamino-propyloxy)-quinazoline
melting point: 222° C.
Mass spectrum (ESI$^+$): m/z=525, 527 [M+H]$^+$

(26) 4-[(3-chloro-4-fluoro-phenyl)amino]-6-(1-methanesulphonyl-piperidin-4-yloxy)-quinazoline
R$_f$ value: 0.44 (silica gel, methylene chloride/methanol=9:1)
Mass spectrum (ESI$^+$): m/z=451, 453 [M+H]$^+$

(27) 4-[(3-chloro-4-fluoro-phenyl)amino]-6-{1-[(morpholin-4-yl)carbonyl]-piperidin-4-yloxy}-quinazoline The reaction takes place with (morpholin-4-yl)carbonylchloride in acetonitrile.
R$_f$ value: 0.40 (silica gel, methylene chloride/methanol=9:1)
Mass spectrum (ESI$^+$): m/z=486, 488 [M+H]$^+$

(28) 4-[(3-chloro-4-fluoro-phenyl)amino]-6-(1-acetyl-piperidin-4-yloxy)-quinazoline The reaction takes place with acetic anhydride.
R$_f$ value: 0.50 (silica gel, methylene chloride/methanol=9:1)
Mass spectrum (ESI$^+$): m/z=415, 417 [M+H]$^+$

(29) 4-[(3-chloro-4-fluoro-phenyl)amino]-6-{1-[(dimethylamino)carbonyl]-piperidin-4-yloxy}-quinazoline The reaction takes place with N,N-dimethylcarbamoylchloride.
R$_f$ value: 0.47 (silica gel, methylene chloride/methanol=9:1)
Mass spectrum (ESI$^+$): m/z=444, 446 [M+H]$^+$

(30) 4-[(3-chloro-4-fluoro-phenyl)amino]-6-{trans-4-acetylamino-cyclohexan-1-yloxy}-7-methoxy-quinazoline The reaction takes place with acetic anhydride.
R$_f$ value: 0.50 (silica gel, methylene chloride/methanol=9:1)
Mass spectrum (ESI$^+$): m/z=459, 461 [M+H]$^+$

(31) 4-[(3-chloro-4-fluoro-phenyl)amino]-6-{trans-4-[(dimethylamino)carbonylamino]-cyclohexan-1-yloxy}-7-methoxy-quinazoline The reaction takes place with N,N-dimethylcarbamoylchloride.
R$_f$ value: 0.40 (silica gel, methylene chloride/methanol=9:1)
Mass spectrum (ESI$^+$): m/z=488, 490 [M+H]$^+$

(32) 4-[(3-chloro-4-fluoro-phenyl)amino]-6-[trans-4-(2-methoxy-acetylamino)-cyclohexan-1-yloxy]-7-methoxy-quinazoline The reaction takes place with methoxyacetic acid chloride.
R$_f$ value: 0.35 (silica gel, methylene chloride/methanol=9:1)
Mass spectrum (ESI$^+$): m/z=489, 491 [M+H]$^+$

(33) 4-[(3-chloro-4-fluoro-phenyl)amino]-6-[1-(2-methoxy-acetyl)-piperidin-4-yloxy]-quinazoline The reaction takes place with methoxyacetic acid chloride.
R$_f$ value: 0.41 (silica gel, methylene chloride/methanol=9:1)
Mass spectrum (ESI$^+$): m/z=445, 447 [M+H]$^+$

(34) 4-[(3-chloro-4-fluoro-phenyl)amino]-6-(1-isopropyloxycarbonyl-piperidin-4-yloxy)-7-methoxy-quinazoline The reaction takes place with isopropyl chloroformate.
$R_f$ value: 0.67 (silica gel, ethyl acetate/methanol/conc. aqueous ammonia=98:2:1)
Mass spectrum (ESI$^+$): m/z=489, 491 [M+H]$^+$

(35) 4-[(3-chloro-4-fluoro-phenyl)amino]-6-(1-cyano-piperidin-4-yloxy)-quinazoline
The reaction takes place with bromocyanogen in methylene chloride.
$R_f$ value: 0.49 (silica gel, methylene chloride/methanol 9:1)
Mass spectrum (ESI$^-$): m/z=396, 398 [M–H]$^-$

(36) 4-[(3-chloro-4-fluoro-phenyl)amino]-6-{1-[(dimethylamino)sulphonyl]-piperidin-4-yloxy}-quinazoline
The reaction takes place with N,N-dimethylsulphamoylchloride in acetonitrile.
$R_f$ value: 0.34 (silica gel, methylene chloride/methanol=9:1)
Mass spectrum (ESI$^+$): m/z=480, 482 [M+H]$^+$

(37) 4-[(3-chloro-4-fluoro-phenyl)amino]-6-{1-[(morpholin-4-yl)sulphonyl]-piperidin-4-yloxy}-quinazoline
The reaction takes place with (morpholin-4-yl)sulphonyl chloride in acetonitrile.
$R_f$ value: 0.15 (silica gel, cyclohexane/ethyl acetate=1:1)
Mass spectrum (ESI$^+$): m/z=522, 524 [M+H]$^+$

(38) 4-[(3-chloro-4-fluoro-phenyl)amino]-6-[1-(2-acetylamino-ethyl)-piperidin-4-yloxy]-quinazoline
The reaction takes place with acetic anhydride in acetonitrile.
melting point: 221° C.
Mass spectrum (ESI$^+$): m/z=458, 460 [M+H]$^+$

(39) 4-[(3-chloro-4-fluoro-phenyl)amino]-6-{1-[(diethylamino)carbonyl]-piperidin-4-yloxy}-7-methoxy-quinazoline
The reaction takes place with N,N-diethylcarbamoylchloride.
$R_f$ value: 0.40 (silica gel, ethyl acetate/methanol/conc. aqueous ammonia=95:5:1)
Mass spectrum (ESI$^+$): m/z=502, 504 [M+H]$^+$

(40) 4-[(3-chloro-4-fluoro-phenyl)amino]-6-{1-[(piperidin-1-yl)carbonyl]-piperidin-4-yloxy}-7-methoxy-quinazoline
The reaction takes place with (piperidin-1-yl)carbonylchloride.
$R_f$ value: 0.51 (silica gel, ethyl acetate/methanol/conc. aqueous ammonia=95:5:1)
Mass spectrum (ESI$^-$): m/z=512, 514 [M–H]$^-$

(41) 4-[(3-chloro-4-fluoro-phenyl)amino]-6-{1-[(pyrrolidin-1-yl)carbonyl]-piperidin-4-yloxy}-7-methoxy-quinazoline
The reaction takes place with (pyrrolidin-1-yl)carbonylchloride.
melting point: 237° C.
Mass spectrum (ESI$^+$): m/z=500, 502 [M+H]$^+$

(42) 4-[(3-chloro-4-fluoro-phenyl)amino]-6-{1-[(4-methyl-piperazin-1-yl)carbonyl]-piperidin-4-yloxy}-7-methoxy-quinazoline
The reaction takes place with (4-methyl-piperazin-1-yl)carbonylchloride-hydrochloride.
$R_f$ value: 0.28 (silica gel, methylene chloride/methanol/conc. aqueous ammonia=90:10:1)
Mass spectrum (ESI$^-$): m/z=527, 529 [M–H]$^-$

(43) 4-[(3-chloro-4-fluoro-phenyl)amino]-6-[cis-4-(N-methanesulphonyl-N-methyl-amino)-cyclohexan-1-yloxy]-7-methoxy-quinazoline
The reaction takes place in methylene chloride.
$R_f$ value: 0.71 (silica gel, ethyl acetate/methanol=9:1)
Mass spectrum (ESI$^+$): m/z=509, 511 [M+H]$^+$

(44) 4-[(3-chloro-4-fluoro-phenyl)amino]-6-[cis-4-(N-acetyl-N-methyl-amino)-cyclohexan-1-yloxy]-7-methoxy-quinazoline
The reaction takes place with acetic anhydride.
melting point: 234° C.
Mass spectrum (ESI$^+$): m/z=473, 475 [M+H]$^+$

(45) 4-[(3-chloro-4-fluoro-phenyl)amino]-6-{cis-4-[N-(2-methoxy-acetyl)-N-methyl-amino]-cyclohexan-1-yloxy}-7-methoxy-quinazoline
The reaction takes place with methoxyacetic acid chloride.
$R_f$ value: 0.40 (silica gel, ethyl acetate/methanol=9:1)
Mass spectrum (ESI$^+$): m/z=503, 505 [M+H]$^+$

(46) 4-[(3-chloro-4-fluoro-phenyl)amino]-6-[cis-4-(N-dimethylaminocarbonyl-N-methyl-amino)-cyclohexan-1-yloxy]-7-methoxy-quinazoline
The reaction takes place with N,N-dimethylcarbamoylchloride.
$R_f$ value: 0.51 (silica gel, ethyl acetate/methanol=9:1)
Mass spectrum (ESI$^+$): m/z=502, 504 [M+H]$^+$

(47) 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline
The reaction takes place with (morpholin-4-yl)carbonylchloride.
$R_f$ value: 0.50 (silica gel, ethyl acetate/methanol=9:1)
Mass spectrum (ESI$^+$): m/z=544, 546 [M+H]$^+$

(48) 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
The reaction takes place with (morpholin-4-yl)sulphonyl chloride in acetonitrile.
$R_f$ value: 0.24 (Reversed phase ready-made TLC plate (E. Merck), acetonitrile/water/trifluoroacetic acid=50:50:1)
Mass spectrum (ESI$^+$): m/z=580, 582 [M+H]$^+$

(49) 4-[(3-chloro-4-fluoro-phenyl)amino]-6-[cis-4-(N-dimethylaminosulphonyl-N-methyl-amino)-cyclohexan-1-yloxy]-7-methoxy-quinazoline
The reaction takes place with N,N-dimethylsulphamoylchloride in acetonitrile.
$R_f$ value: 0.53 (silica gel, ethyl acetate)
Mass spectrum (ESI$^+$): m/z=538, 540 [M+H]$^+$

(50) 4-[(3-chloro-4-fluoro-phenyl)amino]-6-(trans-4-ethanesulphonylamino-cyclohexan-1-yloxy)-7-methoxy-quinazoline
The reaction takes place with ethanesulphonic acid chloride in methylene chloride.
$R_f$ value: 0.41 (silica gel, ethyl acetate)
Mass spectrum (ESI$^+$): m/z=509, 511 [M+H]$^+$

(51) 4-[(3-chloro-4-fluoro-phenyl)amino]-6-1-[(morpholin-4-yl)carbonyl]-piperidin-4-yloxy}-7-ethoxy-quinazoline
The reaction takes place with (morpholin-4-yl)carbonylchloride.
$R_f$ value: 0.48 (silica gel, methylene chloride/methanol=9:1)
Mass spectrum (ESI$^+$): m/z=530, 532 [M+H]$^+$

(52) 4-[(3-chloro-4-fluoro-phenyl)amino]-6-(1-methanesulphonyl-piperidin-4-yloxy)-7-ethoxy-quinazoline
$R_f$ value: 0.50 (silica gel, methylene chloride/methanol=9:1)
Mass spectrum (ESI$^+$): m/z=495, 497 [M+H]$^+$

(53) 4-[(3-chloro-4-fluoro-phenyl)amino]-6-[1-(2-methoxy-acetyl)-piperidin-4-yloxy]-7-ethoxy-quinazoline The reaction takes place with methoxyacetic acid chloride.

R$_f$ value: 0.40 (silica gel, methylene chloride/methanol=20:1)

Mass spectrum (ESI$^+$): m/z=489, 491 [M+H]$^+$

(54) 4-[(3-chloro-4-fluoro-phenyl)amino]-6-(1-methanesulphonyl-piperidin-4-yloxy)-7-(2-methoxy-ethoxy)-quinazoline R$_f$ value: 0.47 (silica gel, methylene chloride/methanol=9:1)

Mass spectrum (ESI$^+$): m/z=525, 527 [M+H]$^+$

(55) 4-[(3-chloro-4-fluoro-phenyl)amino]-6-{1-[(morpholin-4-yl)carbonyl]-piperidin-4-yloxy}-7-(2-methoxy-ethoxy)-quinazoline The reaction takes place with (morpholin-4-yl)carbonylchloride.

R$_f$ value: 0.48 (silica gel, methylene chloride/methanol=9:1)

Mass spectrum (ESI$^+$): m/z=560, 562 [M+H]$^+$

(56) 4-[(3-chloro-4-fluoro-phenyl)amino]-6-[1-(2-methoxy-acetyl)-piperidin-4-yloxy]-7-(2-methoxy-ethoxy)-quinazoline The reaction takes place with methoxyacetic acid chloride.

R$_f$ value: 0.48 (silica gel, methylene chloride/methanol=9:1)

Mass spectrum (ESI$^+$): m/z=519, 521 [M+H]$^+$

(57) 4-[(3-chloro-4-fluoro-phenyl)amino]-6-(cis-4-acetylamino-cyclohexan-1-yloxy)-7-methoxy-quinazoline The reaction takes place with acetic anhydride.

melting point: 281° C.

Mass spectrum (ESI$^+$): m/z=459, 461 [M+H]$^+$

(58) 4-[(3-chloro-4-fluoro-phenyl)amino]-6-(cis-4-(2-methoxy-acetylamino)-cyclohexan-1-yloxy]-7-methoxy-quinazoline The reaction takes place with methoxyacetic acid chloride.

melting point: 264° C.

Mass spectrum (ESI$^+$): m/z=489, 491 [M+H]$^+$

(59) 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline The reaction takes place with (piperidin-1-yl)carbonylchloride.

melting point: 253° C.

Mass spectrum (ESI$^+$): m/z=542, 544 [M+H]$^+$

(60) 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline The reaction takes place with (4-methyl-piperazin-1-yl)carbonylchloride-hydrochloride.

melting point: 262° C.

Mass spectrum (ESI$^+$): m/z=557, 559 [M+H]$^+$

(61) 4-[(3-chloro-4-fluoro-phenyl)amino]-6-[cis-4-(N-ethanesulphonyl-N-methyl-amino)-cyclohexan-1-yloxy]-7-methoxy-quinazoline The reaction takes place with ethanesulphonic acid chloride in methylene chloride.

R$_f$ value: 0.19 (Reversed phase ready-made TLC plate (E. Merck), acetonitrile/water/trifluoroacetic acid=50:50:1)

Mass spectrum (ESI$^+$): m/z=523, 525 [M+H]$^+$

(62) 4-[(3-chloro-4-fluoro-phenyl)amino]-6-{cis-4-[(morpholin-4-yl)carbonylamino]-cyclohexan-1-yloxy}-7-methoxy-quinazoline The reaction takes place with (morpholin-4-yl)carbonylchloride.

R$_f$ value: 0.33 (Reversed phase ready-made TLC plate (E. Merck), acetonitrile/water/trifluoroacetic acid=50:50:1)

Mass spectrum (ESI$^+$): m/z=530, 532 [M+H]$^+$

(63) 4-[(3-chloro-4-fluoro-phenyl)amino]-6-{cis-4-[(morpholin-4-yl)sulphonylamino]-cyclohexan-1-yloxy}-7-methoxy-quinazoline The reaction takes place with (morpholin-4-yl)sulphonyl chloride in acetonitrile.

R$_f$ value: 0.81 (silica gel, ethyl acetate/methanol=9:1)

Mass spectrum (ESI$^+$): m/z=566, 568 [M+H]$^+$

(64) 4-[(3-ethynyl-phenyl)amino]-6-(1-acetyl-piperidin-4-yloxy)-7-methoxy-quinazoline The reaction takes place with acetic anhydride.

R$_f$ value: 0.30 (silica gel, ethyl acetate/methanol/conc. aqueous ammonia=90:10:1)

Mass spectrum (ESI$^+$): m/z=417 [M+H]$^+$

(65) 4-[(3-ethynyl-phenyl)amino]-6-[1-(2-methoxy-acetyl)-piperidin-4-yloxy]-7-methoxy-quinazoline The reaction takes place with methoxyacetic acid chloride.

R$_f$ value: 0.37 (silica gel, methylene chloride/methanol/conc. aqueous ammonia=90:10:1)

Mass spectrum (ESI$^+$): m/z=447 [M+H]$^+$

(66) 4-[(3-ethynyl-phenyl)amino]-6-(1-methanesulphonyl-piperidin-4-yloxy)-7-methoxy-quinazoline R$_f$ value: 0.59 (silica gel, ethyl acetate/methanol/conc. aqueous ammonia=90:10:1)

Mass spectrum (ESI$^+$): m/z=453 [M+H]$^+$

(67) 4-[(3-ethynyl-phenyl)amino]-6-{1-[(morpholin-4-yl)carbonyl]-piperidin-4-yloxy}-7-methoxy-quinazoline The reaction takes place with (morpholin-4-yl)carbonylchloride.

R$_f$ value: 0.43 (silica gel, ethyl acetate/methanol/conc. aqueous ammonia=90:10:1)

Mass spectrum (ESI$^+$): m/z=488 [M+H]$^+$

(68) 4-[(3-chloro-4-fluoro-phenyl)amino]-6-[trans-4-(N-methanesulphonyl-N-methyl-amino)-cyclohexan-1-yloxy]-7-methoxy-quinazoline R$_f$ value: 0.50 (silica gel, methylene chloride/methanol=9:1)

Mass spectrum (ESI$^+$): m/z=509, 511 [M+H]$^+$

(69) 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline The reaction takes place with (morpholin-4-yl)carbonylchloride.

R$_f$ value: 0.54 (silica gel, methylene chloride/methanol=9:1)

Mass spectrum (ESI$^+$): m/z=544, 546 [M+H]$^+$

(70) 4-{[3-methyl-4-(pyridin-3-yloxy)-phenyl]amino}-6-(1-methanesulphonyl-piperidin-4-yloxy)-7-methoxy-quinazoline-methanesulphonate R$_f$ value: 0.58 (Reversed phase ready-made TLC plate (E. Merck), acetonitrile/water/trifluoroacetic acid=50:50:1)

Mass spectrum (ESI$^+$): m/z=536 [M+H]$^+$

(71) 4-[(3-chloro-4-[(3-fluoro-benzyl)oxy]-phenyl)amino]-6-(1-methanesulphonyl-piperidin-4-yloxy)-7-methoxy-quinazoline R$_f$ value: 0.80 (silica gel, methylene chloride/methanol=9:1)

Mass spectrum (ESI$^+$): m/z=587, 589 [M+H]$^+$

EXAMPLE 4

4-[(3-chloro-4-fluoro-phenyl)amino]-6-(cis-4-{[3-(morpholin-4-yl)-propyl]sulphonylamino}-cyclohexan-1-yloxy)-7-methoxy-quinazoline

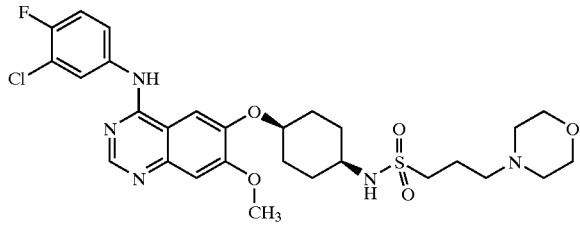

23 μl of morpholine are added to 60 mg of 4-[(3-chloro-4-fluoro-phenyl)amino]-6-{cis-4-[(3-chloropropyl)sulphonylamino]-cyclohexan-1-yloxy}-7-methoxy-quinazoline in 2 ml acetonitrile and the reaction mixture is refluxed overnight. For working up the mixture is taken up in ethyl acetate and washed with water. The organic phase is dried over magnesium sulphate and evaporated down. The crude product is purified through a silica gel column with methylene chloride/methanol (9:1) as eluant.

Yield: 18 mg (27% of theory)

$R_f$ value: 0.36 (silica gel, methylene chloride/methanol=9:1)

Mass spectrum (ESI$^+$): m/z=608, 610 [M+H]$^+$

The following compounds are obtained analogously to Example 4:

(1) 4-[(3-chloro-4-fluoro-phenyl)amino]-6-(trans-4-{[3-(morpholin-4-yl)-propyl]sulphonylamino}-cyclohexan-1-yloxy)-7-methoxy-quinazoline

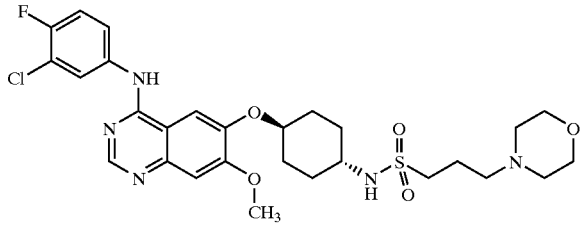

$R_f$ value: 0.16 (silica gel, ethyl acetate/methanol/conc. aqueous ammonia=90:10:1)

Mass spectrum (ESI$^+$): m/z=608, 610 [M+H]$^+$ (2) 4-[(3-chloro-4-fluoro-phenyl)amino]-6-(tetrahydropyran-4-yloxy)-7-[4-(morpholin-4-yl)-butyloxy]-quinazoline Carried out in the presence of sodium carbonate and sodium iodide in N-methylpyrrolidone at 100° C.

$R_f$ value: 0.18 (silica gel, ethyl acetate/methanol/conc. aqueous ammonia=40:10:0.5)

Mass spectrum (ESI$^+$): m/z=531, 533 [M+H]$^+$ (3) 4-[(3-chloro-4-fluoro-phenyl)amino]-6-((S)-tetrahydrofuran-3-yloxy)-7-[4-(morpholin-4-yl)-butyloxy]-quinazoline Carried out in the presence of sodium carbonate and sodium iodide in N-methylpyrrolidone at 100° C.

$R_f$ value: 0.32 (silica gel, ethyl acetate/methanol/conc. aqueous ammonia=80:20:1)

Mass spectrum (ESI$^+$): m/z=517, 519 [M+H]$^+$ (4) 4-[(3-chloro-4-fluoro-phenyl)amino]-6-{1-[(morpholin-4-yl)acetyl]-piperidin-4-yloxy}-quinazoline Carried out in the presence of Hunig base in tetrahydrofuran at ambient temperature.

$R_f$ value: 0.30 (silica gel, methylene chloride/methanol=9:1)

Mass spectrum (ESI$^+$): m/z=500, 502 [M+H]$^+$ (5) 4-[(3-chloro-4-fluoro-phenyl)amino]-6-(1-dimethylaminoacetyl-piperidin-4-yloxy)-quinazoline Carried out in the presence of Hunig base in tetrahydrofuran at ambient temperature.

$R_f$ value: 0.11 (silica gel, methylene chloride/methanol/conc. aqueous ammonia=90:10:1)

Mass spectrum (ESI$^+$): m/z=458, 460 [M+H]$^+$ (6) 4-[(3-chloro-4-fluoro-phenyl)amino]-6-(1-dimethylaminoacetyl-piperidin-4-yloxy)-7-methoxy-quinazoline Carried out in the presence of Hunig base in tetrahydrofuran at ambient temperature.

$R_f$ value: 0.19 (silica gel, ethyl acetate/methanol/conc. aqueous ammonia=90:10:1)

Mass spectrum (ESI$^+$): m/z=488, 490 [M+H]$^+$ (7) 4-[(3-chloro-4-fluoro-phenyl)amino]-6-{1-[(morpholin-4-yl)acetyl]-piperidin-4-yloxy}-7-methoxy-quinazoline Carried out in the presence of Hunig base in tetrahydrofuran at ambient temperature.

Mass spectrum (ESI$^+$): m/z=530, 532 [M+H]$^+$

EXAMPLE 5

4-[(3-chloro-4-fluoro-phenyl)amino]-6-((S)-pyrrolidin-3-yloxy)-7-methoxy-quinazoline-dihydrochloride A solution of 370 mg 4-[(3-chloro-4-fluoro-phenyl)amino]-6-[(S)-1-(tert.-butyloxy-carbonyl)-pyrrolidin-3-yloxy]-7-methoxy-quinazoline in 5 ml dioxane is combined with 0.32 ml concentrated hydrochloric acid and stirred overnight at ambient temperature. The precipitate formed is suction filtered and washed with copious amounts of dioxane. The crude product is dissolved in a little methanol and re-precipitated by the addition of the same amount of ethyl acetate. The white solid thus obtained is suction filtered and dried.

Yield: 200 mg (57% of theory)

melting point: 281° C.

Mass spectrum (ESI$^+$): m/z=389, 391 [M+H]$^+$

The following compounds are obtained analogously to Example 5:

(1) 4-[(3-chloro-4-fluoro-phenyl)amino]-6-(piperidin-3-yloxy)-7-methoxy-quinazoline-dihydrochloride melting point: 263° C.

Mass spectrum (ESI$^+$): m/z=403, 505 [M+H]$^+$ (2) 4-[(3-chloro-4-fluoro-phenyl)amino]-6-[1-(2-amino-ethyl)-piperidin-4-yloxy]-7-methoxy-quinazoline-dihydrochloride melting point: 277° C.

Mass spectrum (ESI$^+$): m/z=446, 448 [M+H]$^+$ (3) 4-[(3-chloro-4-fluoro-phenyl)amino]-6-(3-amino-cyclohexan-1-yloxy)-7-methoxy-quinazoline-dihydrochloride Mass spectrum (ESI$^+$): m/z=417, 419 [M+H]$^+$ (4) 4-[(3-chloro-4-fluoro-phenyl)amino]-6-(tetrahydropyran-4-yloxy)-7-(2-amino-ethoxy)-quinazoline-dihydrochloride Carried out with isopropanolic hydrochloric acid (5-6 M) in methylene chloride.

$R_f$ value: 0.58 (Reversed phase ready-made TLC plate (E. Merck), acetonitrile/water/trifluoroacetic acid=50:50:1)

Mass spectrum (ESI⁺): m/z=433, 435 [M+H]⁺

(5) 4-[(3-chloro-4-fluoro-phenyl)amino]-6-(tetrahydropyran-4-yloxy)-7-(3-amino-propyloxy)-quinazoline-dihydrochloride Carried out with isopropanolic hydrochloric acid (5-6 M) in methylene chloride.

$R_f$ value: 0.44 (Reversed phase ready-made TLC plate (E. Merck), methanol/5% aqueous sodium chloride solution=7:3)

Mass spectrum (ESI⁺): m/z=447, 449 [M+H]⁺

(6) 4-[(3-chloro-4-fluoro-phenyl)amino]-6-[1-(2-aminoethyl)-piperidin-4-yloxy]-quinazoline-dihydrochloride $R_f$ value: 0.50 (Reversed phase ready-made TLC plate (E. Merck), acetonitrile/water/trifluoroacetic acid=50:50: 1)

Mass spectrum (ESI⁺): m/z=416, 418 [M+H]⁺

(7) 4-[(3-chloro-4-fluoro-phenyl)amino]-6-(cis-4-methylamino-cyclohexan-1-yloxy)-7-methoxy-quinazoline-dihydrochloride Carried out with isopropanolic hydrochloric acid (5-6 M) in methylene chloride.

$R_f$ value: 0.35 (Reversed phase ready-made TLC plate (E. Merck), acetonitrile/water/trifluoroacetic acid=50:50:1)

Mass spectrum (ESI⁺): m/z=431, 433 [M+H]⁺

(8) 4-[(3-ethynyl-phenyl)amino]-6-(piperidin-4-yloxy)-7-methoxy-quinazoline-dihydrochloride Carried out with isopropanolic hydrochloric acid (5-6 M) in methylene chloride.

$R_f$ value: 0.50 (Reversed phase ready-made TLC plate (E. Merck), acetonitrile/water/trifluoroacetic acid=50:50:1)

Mass spectrum (ESI⁺): m/z=375 [M+H]⁺

(9) 4-[(3-chloro-4-fluoro-phenyl)amino]-6-(trans-4-methylamino-cyclohexan-1-yloxy)-7-methoxy-quinazoline-dihydrochloride melting point: 251° C.

Mass spectrum (ESI⁺): m/z=431, 433 [M+H]⁺

(10) 4-{[3-methyl-4-(pyridin-3-yloxy)-phenyl]amino)-6-(piperidin-4-yloxy)-7-methoxy-quinazoline dihydrochloride $R_f$ value: 0.50 (Reversed phase ready-made TLC plate (E. Merck), acetonitrile/water/trifluoroacetic acid=50:50:1)

Mass spectrum (ESI⁺): m/z=458 [M+H]⁺

(11) 4-({3-chloro-4-[(3-fluorobenzyl)oxy]-phenyl}amino)-6-(piperidin-4-yloxy)-7-methoxy-quinazoline dihydrochloride $R_f$ value: 0.38 (Reversed phase ready-made TLC plate (E. Merck), acetonitrile/water/trifluoroacetic acid=50:50:1)

Mass spectrum (ESI⁺): m/z=507, 509 [M−H]⁻

(12) 4-{[3-methyl-4-(pyridin-3-yloxy)-phenyl}amino)-6-(trans-4-aminocyclohexan-1-yloxy)-7-methoxy-quinazoline dihydrochloride $R_f$ value: 0.58 (Reversed phase ready-made TLC plate (E. Merck), acetonitrile/water/trifluoroacetic acid=50:50:1)

Mass spectrum (ESI⁺): m/z=472 [M+H]⁺

(13) 4-({3-chloro-4-[(3-fluorobenzyl)oxy]-phenyl}amino)-6-(trans-4-aminocyclohexan-1-yloxy)-7-methoxy-quinazoline dihydrochloride $R_f$ value: 0.48 (Reversed phase ready-made TLC plate (E. Merck), acetonitrile/water/trifluoroacetic acid=50:50:1)

Mass spectrum (ESI⁺): m/z=523, 525 [M+H]⁺

EXAMPLE 6

4-[(3-chloro-4-fluoro-phenyl)amino]-6-(tetrahydropyran-4-yloxy)-7-hydroxy-quinazoline A mixture of 9.00 g 4-[(3-chloro-4-fluoro-phenyl)amino]-6-(tetrahydropyran-4-yloxy)-7-benzyloxy-quinazoline-hydrochloride and 50 ml trifluoroacetic acid is heated to 100° C. for 1.5 hours. Then the reaction mixture is evaporated and the residue is taken up in 10 ml acetonitrile. This solution is added dropwise to 100 ml saturated sodium hydrogen carbonate solution with vigorous stirring. After 1.5 hours the precipitate formed is suction filtered and washed several times with water. The crude product is stirred with diethyl ether, suction filtered and dried.

Yield: 5.90 g (87% of theory)

$R_f$ value: 0.21 (silica gel, ethyl acetate)

Mass spectrum (ESI⁺): m/z=390, 392 [M+H]⁺

The following compounds are obtained analogously to Example 6:

(1) 4-[(3-chloro-4-fluoro-phenyl)amino]-6-((S)-tetrahydrofuran-3-yloxy)-7-hydroxy-quinazoline $R_f$ value: 0.44 (silica gel, ethyl acetate/methanol=9:1)

Mass spectrum (ESI⁺): m/z=376, 378 [M+H]⁺

EXAMPLE 7

4-[(3-chloro-4-fluoro-phenyl)amino]-6-(tetrahydropyran-4-yloxy)-7-[3-(morpholin-4-yl)-propyloxy]-quinazoline A mixture of 300 mg 4-[(3-chloro-4-fluoro-phenyl)amino]-6-(tetrahydropyran-4-yloxy)-7-hydroxy-quinazoline, 130 mg 3-(morpholin-4-yl)-propylchloride and 530 mg potassium carbonate in 5 ml N,N-dimethylformamide is stirred overnight at 80° C. For working up the reaction mixture is diluted with 25 ml of water and extracted with ethyl acetate. The combined organic phases are washed with saturated sodium chloride solution, dried over magnesium sulphate and evaporated. The residue is stirred with diethyl ether, suction filtered and dried.

Yield: 250 mg (63% of theory)

melting point: 205° C.

Mass spectrum (ESI⁺): m/z=517, 519 [M+H]⁺

The following compounds are obtained analogously to Example 7:

(1) 4-[(3-chloro-4-fluoro-phenyl)amino]-6-(tetrahydropyran-4-yloxy)-7-[2-(morpholin-4-yl)-ethoxy]-quinazoline $R_f$ value: 0.33 (silica gel, ethyl acetate/methanol/conc. aqueous ammonia=40:10:0.5)

Mass spectrum (ESI⁺): m/z=503, 505 [M+H]⁺

(2) 4-[(3-chloro-4-fluoro-phenyl)amino]-6-(tetrahydropyran-4-yloxy)-7-ethoxy-quinazoline $R_f$ value: 0.76 (silica gel, ethyl acetate/methanol/conc. aqueous ammonia=90:10:1)

Mass spectrum (ESI⁺): m/z=418, 420 [M+H]⁺

(3) 4-[(3-chloro-4-fluoro-phenyl)amino]-6-((S)-tetrahydrofuran-3-yloxy)-7-[3-(morpholin-4-yl)-propyloxy]-quinazoline $R_f$ value: 0.20 (silica gel, ethyl acetate/methanol/conc. aqueous ammonia=90:10:1)

Mass spectrum (ESI⁻): m/z=501, 503[M−H]⁻

(4) 4-[(3-chloro-4-fluoro-phenyl)amino]-6-((S)-tetrahydrofuran-3-yloxy)-7-[2-(morpholin-4-yl)-ethoxy]-quinazoline $R_f$ value: 0.19 (silica gel, ethyl acetate/methanol/conc. aqueous ammonia=90:10:1)

Mass spectrum (ESI⁺): m/z=489, 491 [M+H]⁺

(5) 4-[(3-chloro-4-fluoro-phenyl)amino]-6-(tetrahydropyran-4-yloxy)-7-(2-methoxy-ethoxy)-quinazoline $R_f$ value: 0.57 (silica gel, methylene chloride/methanol= 9:1)

Mass spectrum (ESI$^+$): m/z=448, 450 [M+H]$^+$ (6) 4-[(3-chloro-4-fluoro-phenyl)amino]-6-(tetrahydropyran-4-yloxy)-7-[2-(tert.-butyloxycarbonylamino)-ethoxy]-quinazoline $R_f$ value: 0.64 (silica gel, ethyl acetate/methanol/conc. aqueous ammonia=95:5:0.1)

Mass spectrum (ESI$^+$): m/z=533, 535 [M+H]$^+$ (7) 4-[(3-chloro-4-fluoro-phenyl)amino]-6-(tetrahydropyran-4-yloxy)-7-[3-(tert.-butyloxycarbonylamino)-propyloxy]-quinazoline $R_f$ value: 0.74 (silica gel, ethyl acetate/methanol/conc. aqueous ammonia=95:5:0.1)

Mass spectrum (ESI$^+$): m/z=547, 549 [M+H]$^+$

EXAMPLE 8

4-[(3-chloro-4-fluoro-phenyl)amino]-6-(piperidin-4-yloxy)-quinazoline

A solution of 4.55 g 4-[(3-chloro-4-fluoro-phenyl)amino]-6-(1-trifluoroacetyl-piperidin-4-yloxy)-quinazoline-hydrochloride in 35 ml methanol is combined with 13 ml (3 N) sodium hydroxide solution and stirred for about half an hour at ambient temperature. For working up the reaction mixture is diluted with water and extracted with ethyl acetate. The combined organic phases are washed with saturated sodium chloride solution, dried over magnesium sulphate and evaporated. The residue is stirred with diethyl ether, suction filtered and dried.

Yield: 3.00 g (89% of theory)

$R_f$ value: 0.48 (Reversed phase ready-made TLC plate (E. Merck), acetonitrile/water/trifluoroacetic acid=50:50:1)

Mass spectrum (ESI$^+$): m/z=373, 375 [M+H]$^+$

The following compounds are obtained analogously to Example 8:

(1) 4-[(3-chloro-4-fluoro-phenyl)amino]-6-(piperidin-4-yloxy)-7-ethoxy-quinazoline $R_f$ value: 0.20 (silica gel, methylene chloride/methanol/conc. aqueous ammonia=90:10:1)

Mass spectrum (ESI$^+$): m/z=417, 419 [M+H]$^+$ (2) 4-[(3-chloro-4-fluoro-phenyl)amino]-6-(piperidin-4-yloxy)-7-(2-methoxy-ethoxy)-quinazoline $R_f$ value: 0.10 (silica gel, methylene chloride/methanol/conc. aqueous ammonia=90:10:1)

Mass spectrum (ESI$^+$): m/z=447, 449 [M+H]$^+$

EXAMPLE 9

4-[(3-chloro-4-fluoro-phenyl)amino]-6-{1-[(ethylamino)carbonyl]-piperidin-4-yloxy}-7-methoxy-quinazoline Prepared by reacting 4-[(3-chloro-4-fluoro-phenyl)amino]-6-(piperidin-4-yloxy)-7-methoxy-quinazoline with ethyl isocyanate in tetrahydrofuran at ambient temperature.

$R_f$ value: 0.53 (silica gel, ethyl acetate/methanol/conc. aqueous ammonia=90:10:1)

Mass spectrum (ESI$^+$): m/z=474, 476 [M+H]$^+$

The following compounds are obtained analogously to Example 9:

(1) 4-[(3-chloro-4-fluoro-phenyl)amino]-6-{1-[(isopropylamino)carbonyl]-piperidin-4-yloxy}-7-methoxy-quinazoline melting point: 236° C.

Mass spectrum (ESI$^-$): m/z=486, 488 [M−H]$^-$ (2) 4-[(3-chloro-4-fluoro-phenyl)amino]-6-{1-[(phenylamino)carbonyl]-piperidin-4-yloxy}-7-methoxy-quinazoline $R_f$ value: 0.70 (silica gel, ethyl acetate/methanol/conc. aqueous ammonia=95:5:0.1)

Mass spectrum (ESI$^+$): m/z=522, 524 (M+H]$^+$ (3) 4-[(3-chloro-4-fluoro-phenyl)amino]-6-(cis-4-{(N-[(ethylamino)carbonyl]-N-methyl-amino}-cyclohexan-1-yloxy)-7-methoxy-quinazoline $R_f$ value: 0.38 (silica gel, methylene chloride/methanol= 9:1)

Mass spectrum (ESI$^+$): m/z=502, 504 [M+H]$^+$

EXAMPLE 10

4-[(3-chloro-4-fluoro-phenyl)amino]-6-{1-[(dimethylamino)carbonylmethyl]-piperidin-4-yloxy}-quinazoline Prepared by reacting 4-[(3-chloro-4-fluoro-phenyl)amino]-6-(piperidin-4-yloxy)-quinazoline with 2-chloro-N,N-dimethylacetamide in the presence of potassium carbonate in N,N-dimethylformamide at ambient temperature.

$R_f$ value: 0.24 (silica gel, methylene chloride/methanol= 9:1)

Mass spectrum (ESI$^+$): m/z=458, 460 [M+H]$^+$

The following compounds are obtained analogously to Example 10:

(1) 4-[(3-chloro-4-fluoro-phenyl)amino]-6-{1-[(morpholin-4-yl)carbonylmethyl]-piperidin-4-yloxy}-quinazoline $R_f$ value: 0.42 (Reversed phase ready-made TLC plate (E. Merck), acetonitrile/water/trifluoroacetic acid=50:50:1)

Mass spectrum (ESI$^+$): m/z=500, 502 [M+H]$^+$ (2) 4-[(3-chloro-4-fluoro-phenyl)amino]-6-(1-aminocarbonylmethyl-piperidin-4-yloxy)-7-methoxy-quinazoline melting point: 251° C.

Mass spectrum (ESI$^+$): m/z=460, 462 [M+H]$^+$ (3) 4-[(3-chloro-4-fluoro-phenyl)amino]-6-{1-[(dimethylamino)carbonylmethyl]-piperidin-4-yloxy}-7-methoxy-quinazoline melting point: 233° C.

Mass spectrum (ESI$^+$): m/z=488, 490 [M+H]$^+$ (4) 4-[(3-chloro-4-fluoro-phenyl)amino]-6-{1-[(morpholin-4-yl)carbonylmethyl]-piperidin-4-yloxy}-7-methoxy-quinazoline melting point: 245° C.

Mass spectrum (ESI$^+$): m/z=530, 532 [M+H]$^+$ (5) 4-[(3-chloro-4-fluoro-phenyl)amino]-6-[1-(2-methoxyethyl)-piperidin-4-yloxy}-7-methoxy-quinazoline melting point: 178° C.

Mass spectrum (ESI$^+$): m/z=461, 463 [M+H]$^+$ (6) 4-[(3-chloro-4-fluoro-phenyl)amino]-6-{1-[2-(2-oxopyrrolidin-1-yl)ethyl]-piperidin-4-yloxy}-7-methoxy-quinazoline melting point: 234° C.

$R_f$ value: 0.28 (silica gel, methylene chloride/methanol/conc. aqueous ammonia=90:10:1)

Mass spectrum (ESI$^+$): m/z=514, 516 [M+H]$^+$

EXAMPLE 11

4-[(3-chloro-4-fluoro-phenyl)amino]-6-{1-[(tetrahydropyran-4-yl)carbonyl]-piperidin-4-yloxy}-7-methoxy-quinazoline 90 mg 1-hydroxy-1H-benzotriazole and 250 mg 2-(1H-benzotriazol-1-yl)-1,1,3,3-tetramethyluroniumtetrafluoroborate are added to a mixture of 300 mg 4-[(3-chloro-4-fluoro-phenyl)amino]-6-(piperidin-4-yloxy)-7-methoxy-quinazoline-dihydrochloride, 82 mg tetrahydropyran-4-carboxylic acid and 0.54 ml Hünig base in 5 ml N,N-dimethylformamide. The reaction mixture is stirred overnight at ambient temperature. For working up it is combined with 25 ml ethyl acetate and washed with water, 10% potassium carbonate solution and saturated sodium chloride solution. The organic phase is dried over magnesium sulphate and evaporated. The residue is stirred with a little ethyl acetate, suction filtered and dried.

Yield: 250 mg (77% of theory)

$R_f$ value: 0.43 (silica gel, ethyl acetate/methanol/conc. aqueous ammonia=90:10:1)

Mass spectrum (ESI$^+$): m/z=515, 517 [M+H]$^+$

The following compounds are obtained analogously to Example 11:

(1) 4-[(3-chloro-4-fluoro-phenyl)amino]-6-{trans-4-[(tetrahydropyran-4-yl)carbonylamino]-cyclohexan-1-yloxy}-7-methoxy-quinazoline $R_f$ value: 0.44 (silica gel, ethyl acetate/methanol/conc. aqueous ammonia=90:10:1)

Mass spectrum (ESI$^+$): m/z=529, 531 [M+H]$^+$ (2) 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline $R_f$ value: 0.31 (silica gel, ethyl acetate/methanol=9:1)

Mass spectrum (ESI$^+$): m/z=543, 545 [M+H]$^+$ (3) 4-[(3-chloro-4-fluoro-phenyl)amino]-6-{1-[(R)-(tetrahydrofuran-2-yl)carbonyl]-piperidin-4-yloxy)-7-methoxy-quinazoline Melting point: 243° C.

(4) 4-[(3-chloro-4-fluoro-phenyl)amino]-6-{1-[(S)-(tetrahydrofuran-2-yl)carbonyl]-piperidin-4-yloxy)-7-methoxy-quinazoline $R_f$ value: 0.34 (silica gel, ethyl acetate/methanol/conc. aqueous ammonia 90:10:1)

(5) 4-[(3-chloro-4-fluoro-phenyl)amino]-6-{1-[(2-methoxyethyl)carbonyl]-piperidin-4-yloxy)-7-methoxy-quinazoline $R_f$ value: 0.31 (silica gel, methylene chloride/methanol/conc. aqueous ammonia=90:10:1)

Mass spectrum (ESI$^+$): m/z=487, 489 [M−H]$^-$

EXAMPLE 12

4-[(3-chloro-4-fluoro-phenyl)amino]-6-{1-[([1,4]oxazepan-4-yl)carbonyl)-piperidin-4-yloxy}-7-methoxy-quinazoline 4-[(3-chloro-4-fluoro-phenyl)amino]-6-(piperidin-4-yloxy)-7-methoxy-quinazoline-dihydrochloride and 1.05 ml triethylamine are added to 900 mg of 1-methyl-3-[([1,4]oxazepan-4-yl)carbonyl]-3H-imidazol-1-ium-iodide in 10 ml methylene chloride. The yellowish suspension is stirred for about 24 hours at ambient temperature. For working up the reaction mixture is combined with 50 ml methylene chloride and extracted with water as well as 10% citric acid. The organic phase is washed with saturated sodium chloride solution, dried over magnesium sulphate and evaporated down. The residue is chromatographed through a silica gel column with methylene chloride/methanol/conc. ammonia as eluant. The desired product is stirred with diethyl ether, suction filtered and dried.

Yield: 800 mg (80% of theory)

$R_f$ value: 0.30 (silica gel, methylene chloride/methanol/conc. aqueous ammonia=90:10:1)

Mass spectrum (ESI$^+$): m/z=530, 532 [M+H]$^+$

The following compounds are obtained analogously to Example 12:

(1) 4-[(3-chloro-4-fluoro-phenyl)amino]-6-{1-[(cis-2,6-dimethyl-morpholin-4-yl)carbonyl]-piperidin-4-yloxy}-7-methoxy-quinazoline $R_f$ value: 0.41 (silica gel, ethyl acetate/methanol/conc. aqueous ammonia=90:10:1)

Mass spectrum (ESI$^+$): m/z=544, 546 [M+H]$^+$ (2) 4-((3-chloro-4-fluoro-phenyl)amino]-6-{1-[(2-methyl-morpholin-4-yl)carbonyl]-piperidin-4-yloxy}-7-methoxy-quinazoline $R_f$ value: 0.50 (silica gel, ethyl acetate/methanol/conc. aqueous ammonia=90:10:1)

Mass spectrum (ESI$^+$): m/z=530, 532 [M+H]$^+$ (3) 4-[(3-chloro-4-fluoro-phenyl)amino]-6-{1-[(S,S)-(2-oxa-5-aza-bicyclo[2.2.1]hept-5-yl) carbonyl]-piperidin-4-yloxy)-7-methoxy-quinazoline Melting point: 193° C.

(4) 4-[(3-chloro-4-fluoro-phenyl)amino]-6-{1-[(N-methyl-N-2-methoxyethyl-amino)carbonyl]-piperidin-4-yloxy)-7-methoxy-quinazoline Melting point: 171° C.

(5) 4-[(3-chloro-4-fluoro-phenyl)amino]-6-{1-[(N-methyl-N-3-methoxypropyl-amino)carbonyl]-piperidin-4-yloxy)-7-methoxy-quinazoline $R_f$ value: 0.23 (silica gel, methylene chloride/methanol/conc. aqueous ammonia=90:10:1)

Mass spectrum (ESI$^+$): m/z=532, 534 [M+H]$^+$

EXAMPLE 13

4-[(3-chloro-4-fluoro-phenyl)amino]-6-(1-methyl-piperidin-4-yloxy)-7-ethoxy-quinazoline 35 µl 37% aqueous formalin solution and 110 mg of sodium triacetoxyborohydride are added to 175 mg 4-[(3-chloro-4-fluoro-phenyl)amino]-6-(piperidin-4-yloxy)-7-ethoxy-quinazoline in 1 ml of tetrahydrofuran. The reaction mixture is stirred for about four hours at ambient temperature. For working up 5 ml saturated sodium hydrogen carbonate solution are added and the mixture is stirred thoroughly. Then 20 ml ethyl acetate are added and the aqueous phase is separated off. The organic phase is washed with water and saturated sodium chloride solution, dried over magnesium sulphate and evaporated. The residue is stirred with diisopropylether, suction filtered and dried.

Yield: 144 mg (80% of theory)

$R_f$ value: 0.80 (silica gel, methylene chloride/methanol/conc. aqueous ammonia=60:10:1)

Mass spectrum (ESI$^+$): m/z=431, 433 [M+H]$^+$

The following compounds are obtained analogously to Example 13:

(1) 4-[(3-chloro-4-fluoro-phenyl)amino]-6-(1-methyl-piperidin-4-yloxy)-7(2-methoxy-ethoxy)-quinazoline $R_f$ value: 0.85 (silica gel, methylene chloride/methanol/conc. aqueous ammonia=60:10:1)

Mass spectrum (ESI$^+$): m/z=461, 463 [M+H]$^+$ (2) 4-[(3-ethynyl-phenyl)amino]-6-(1-methyl-piperidin-4-yloxy)-7-methoxy-quinazoline-hydrochloride $R_f$ value: 0.26 (silica gel, methylene chloride/methanol/conc. aqueous ammonia=90:10:1)

Mass spectrum (ESI$^+$): m/z=389 [M+H]$^+$ (3) 4-[(3-chloro-4-fluoro-phenyl)amino]-6-(trans-4-dimethylamino-cyclohexan-1-yloxy)-7-methoxy-quinazoline $R_f$ value: 0.80 (aluminium oxide, methylene chloride/methanol=9:1)

Mass spectrum (ESI⁺): m/z=445, 447 [M+H]⁺

(4) 4-[(3-chloro-4-fluoro-phenyl)amino]-S-(1-ethyl-piperidin-4-yloxy)-7-methoxy-quinazoline hydrochloride Carried out with acetaldehyde $R_f$ value: 0.44 (Reversed phase ready-made TLC plate (E. Merck), acetonitrile/water/trifluoroacetic acid=50:50:1)

Mass spectrum (ESI⁺): m/z=431, 433 [M+H]⁺

(5) 4-{[3-methyl-4-(pyridin-3-yloxy)-phenyl]amino}-6-(1-methyl-piperidin-4-yloxy)-7-methoxy-quinazoline $R_f$ value: 0.68 (silica gel, methylene chloride/methanol/conc. aqueous ammonia=60:10:1)

Mass spectrum (ESI⁺): m/z=472 [M+H]⁺

(6) 4-({3-chloro-4-[(3-fluorobenzyl)oxy]-phenyl}amino)-6-(1-methyl-piperidin-4-yloxy)-7-methoxy-quinazoline $R_f$ value: 0.70 (silica gel, methylene chloride/methanol/conc. aqueous ammonia=90:10:1)

Mass spectrum (ESI⁺): m/z=523, 525 [M+H]⁺

EXAMPLE 14

4-[(3-ethynyl-phenyl)amino]-6-[1-(tert.-butyloxycarbonyl)-piperidin-4-yloxy]-7-methoxy-quinazoline A mixture of 3.00 g 4-[(3-ethynyl-phenyl)amino]-6-hydroxy-7-methoxy-quinazoline, 4.50 g 1-(tert.-butyloxycarbonyl)-4-(p-toluolsulphonyloxy)-piperidin and 2.90 g potassium carbonate in 30 ml N,N-dimethylformamide is stirred for two days at 60° C. For working up the mixture is combined with 200 ml ethyl acetate and extracted with water. The organic phase is washed with saturated sodium chloride solution, dried over magnesium sulphate and evaporated. The crude product is purified over a silica gel column with methylene chloride/methanol/conc. ammonia as eluant.

Yield: 3.25 g (67% of theory)

$R_f$ value: 0.25 (silica gel, methylene chloride/methanol/conc. aqueous ammonia=95:5:1)

Mass spectrum (ESI⁺): m/z=475 [M+H]⁺

The following compounds are obtained analogously to Example 14:

(1) 4-[(3-ethynyl-phenyl)amino]-6-(tetrahydropyran-4-yloxy]-7-methoxy-quinazoline $R_f$ value: 0.40 (silica gel, methylene chloride/methanol/conc. aqueous ammonia=90:10:1)

Mass spectrum (ESI⁺): m/z=376 [M+H]⁺

(2) 4-({3-chloro-4-[(3-fluorobenzyl)oxy]-phenyl}amino)-6-(tetrahydropyran-4-yloxy]-7-methoxy-quinazoline $R_f$ value: 0.32 (silica gel, methylene chloride/methanol=20:1)

Mass spectrum (ESI⁺): m/z=510, 512 [M+H]⁺

(3) 4-{[3-methyl-4-(pyridin-3-yloxy)-phenyl]amino}-6-(tetrahydropyran-4-yloxy]-7-methoxy-quinazoline $R_f$ value: 0.55 (silica gel, methylene chloride/methanol=9:1)

Mass spectrum (ESI⁺): m/z=459 [M+H]⁺

(4) 4-{[3-methyl-4-(pyridin-3-yloxy)-phenyl]amino}-6-(1-tert.butyloxycarbonyl-piperidin-4-yloxy)-7-methoxy-quinazoline $R_f$ value: 0.40 (silica gel, methylene chloride/methanol=9:1)

Mass spectrum (ESI⁺): m/z=558 [M+H]⁺

(5) 4-({3-chloro-4-[(3-fluorobenzyl)oxy]-phenyl}amino)-6-(1-tert. butyloxycarbonyl-piperidin-4-yloxy)-7-methoxy-quinazoline $R_f$ value: 0.65 (silica gel, methylene chloride/methanol=9:1)

Mass spectrum (ESI⁺): m/z=609, 611 [M+H]⁺

(6) 4-{[3-methyl-4-(pyridin-3-yloxy)-phenyl]amino}-6-[trans-4-(tert.butyloxycarbonylamino)-cyclohexan-1-yloxy)-7-methoxy-quinazoline The alkylating agent used, cis-4-(tert.butyloxycarbonylamino)-1-(4-methylphenylsulphonyloxy)-cyclohexane (mass spectrum (ESI⁺): m/z=370 [M+H]⁺) was prepared by reacting cis-4-(tert.butyloxycarbonylamino)-cyclohexanol with 4-methylphenyl-sulphonyl chloride in pyridine.

Mass spectrum (ESI⁺): m/z=572 [M+H]⁺

(7) 4-({3-chloro-4-[(3-fluorobenzyl)oxy]-phenyl}amino)-6-[trans-4-(tert.butyloxycarbonylamino)-cyclohexan-1-yloxy)-7-methoxy-quinazoline The alkylating agent used, cis-4-(tert.butyloxycarbonylamino)-1-(4-methylphenylsulphonyloxy)-cyclohexane (mass spectrum (ESI⁺): m/z=370 [M+H]⁺) was prepared by reacting cis-4-(tert.butyloxycarbonylamino)-cyclohexanol with 4-methylphenyl-sulphonyl chloride in pyridine.

Mass spectrum (ESI⁺): m/z=623, 625 [M+H]⁺

EXAMPLE 15

4-[(3-chloro-4-fluoro-phenyl)amino]-6-{1-[2-(tert.-butyloxycarbonylamino)-ethyl]-piperidin-4-yloxy}-7-methoxy-quinazoline A mixture of 410 mg of 4-[(3-chloro-4-fluoro-phenyl)amino]-6-(piperidin-4-yloxy)-7-methoxy-quinazoline-dihydrochloride, 240 mg of N-(tert.-butyloxycarbonyl)-2-bromo-ethylamine and 360 mg of potassium carbonate in 5 ml N,N-dimethylformamide is stirred overnight at ambient temperature. Then another 80 mg N-(tert.-butyloxycarbonyl)-2-bromo-ethylamine are added and the reaction mixture is stirred for a further four hours at ambient temperature. For working up it is diluted with water and extracted with ethyl acetate. The combined organic phases are washed with saturated sodium chloride solution, dried over magnesium sulphate and evaporated. The residue is chromatographed through a silica gel column with ethyl acetate/methanol (95:5 to 90:1) as eluant.

Yield: 370 mg (79% of theory)

$R_f$ value: 0.33 (Reversed phase ready-made TLC plate (E. Merck), acetonitrile/water/trifluoroacetic acid=50:50:1)

Mass spectrum (ESI⁻): m/z=544, 546 [M−H]⁻

The following compound is obtained analogously to Example 15:

(1) 4-[(3-chloro-4-fluoro-phenyl)amino]-6-{1-[2-(tert.-butyloxycarbonylamino)-ethyl]-piperidin-4-yloxy}-quinazoline $R_f$ value: 0.38 (Reversed phase ready-made TLC plate (E. Merck), acetonitrile/water/trifluoroacetic acid=50:50:1)

Mass spectrum (ESI⁺): m/z=516, 518 [M+H]⁺

EXAMPLE 16

4-[(3-chloro-4-fluoro-phenyl)amino]-6-{1-[(3-methoxypropyl-amino)-carbonyl]-piperidin-4-yloxy}-7-methoxy-quinazoline Prepared by reacting 4-[(3-chloro-4-fluoro-phenyl)amino]-6-{1-[(4-nitrophenyloxy)-carbonyl]-piperidin-4-yloxy}-7-methoxy-quinazoline with 3-methoxypropylamine at 60° C.

$R_f$ value: 0.33 (silica gel, methylene chloride/methanol/conc. aqueous ammonia=90:10:1)

Mass spectrum (ESI$^+$): m/z=518, 520 [M+H]$^+$

The following compound is obtained analogously to Example 15:

(1) 4-[(3-chloro-4-fluoro-phenyl)amino]-6-{1-[(2-methoxyethyl-amino)-carbonyl]-piperidin-4-yloxy}-7-methoxy-quinazoline Mass spectrum (ESI$^+$): m/z=504, 506 [M+H]$^+$ The following compounds may also be prepared analogously to the foregoing Examples and other methods known from the literature:

| Example No. | Structure |
|---|---|
| (1) | 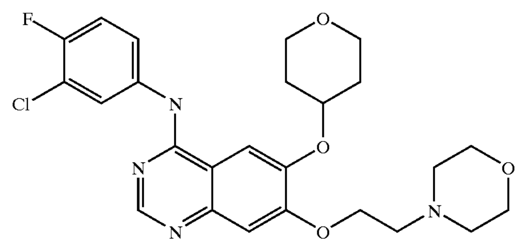 |
| (2) | 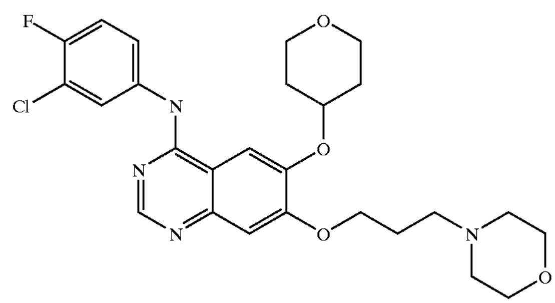 |
| (3) | 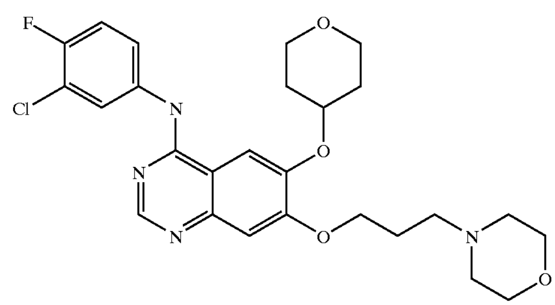 |
| (4) | 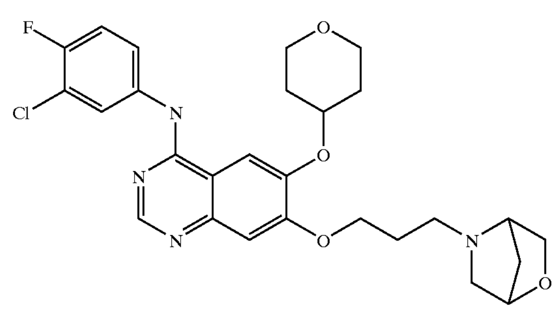 |

-continued
| Example No. | Structure |
|---|---|
| (5) | 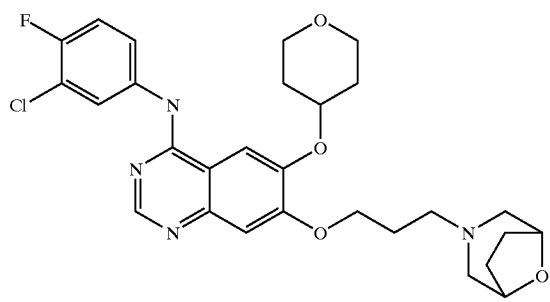 |
| (6) | 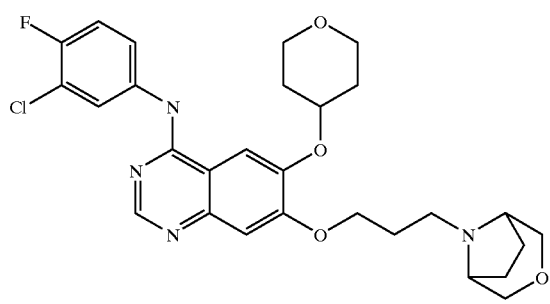 |
| (7) | 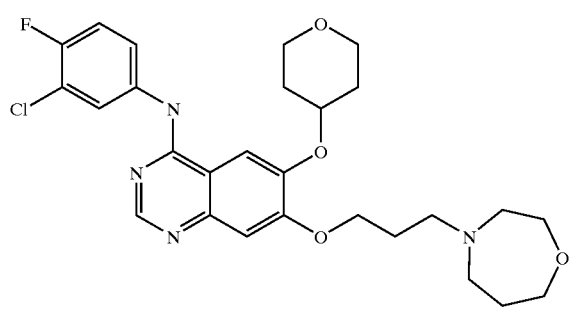 |
| (8) | 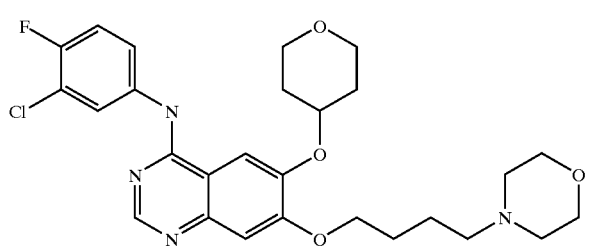 |
| (9) | 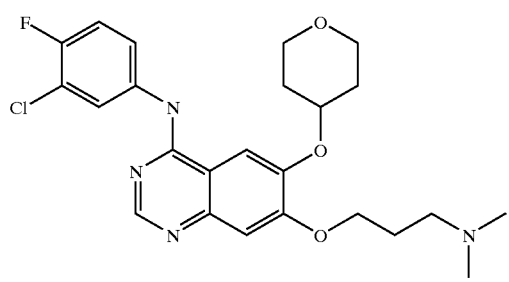 |

-continued
| Example No. | Structure |
|---|---|
| (10) | 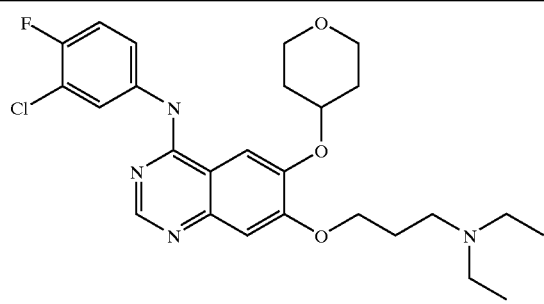 |
| (11) | 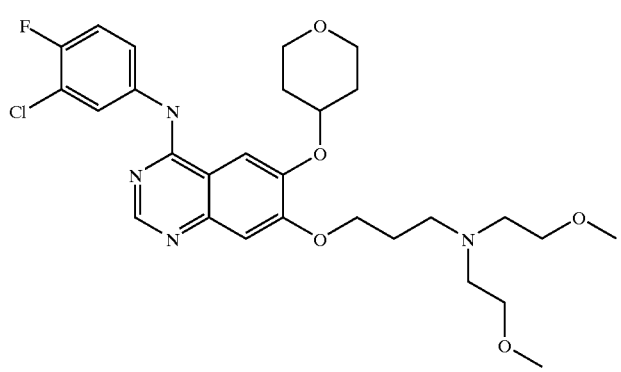 |
| (12) | 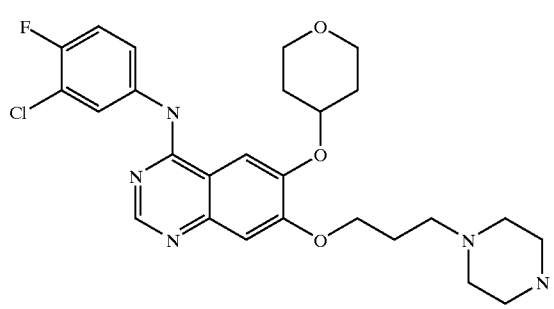 |
| (13) | 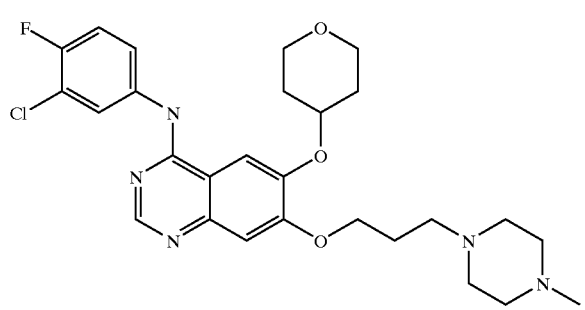 |
| (14) | 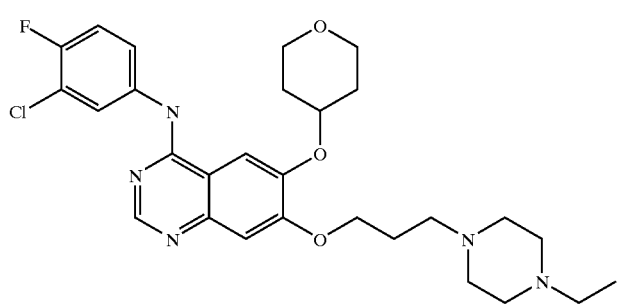 |

-continued
| Example No. | Structure |
|---|---|
| (15) | 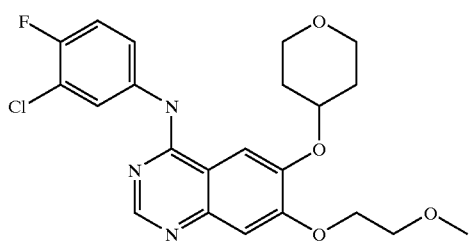 |
| (16) | 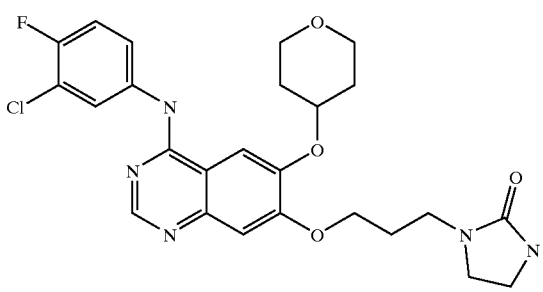 |
| (17) | 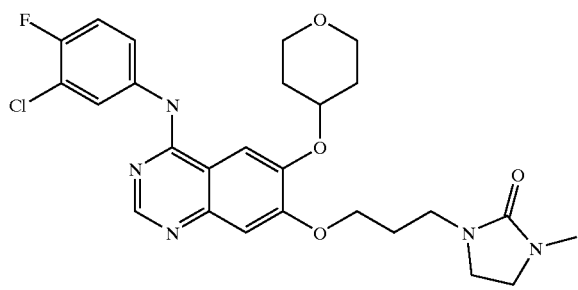 |
| (18) | 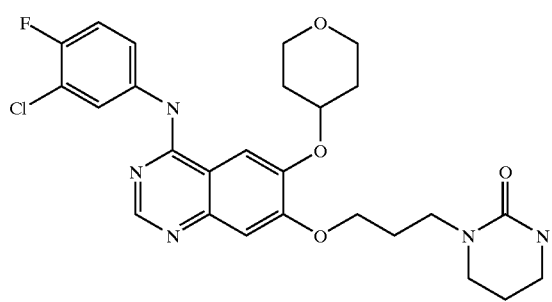 |
| (19) | 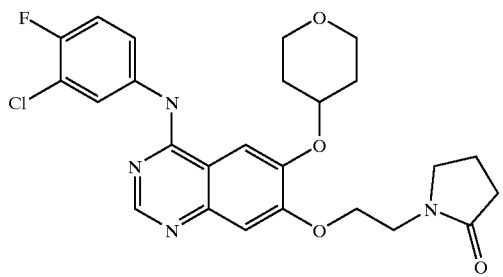 |

-continued
| Example No. | Structure |
|---|---|
| (20) | 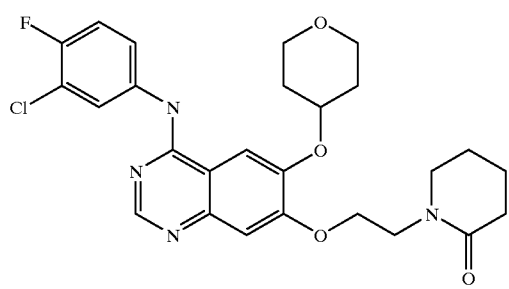 |
| (21) | 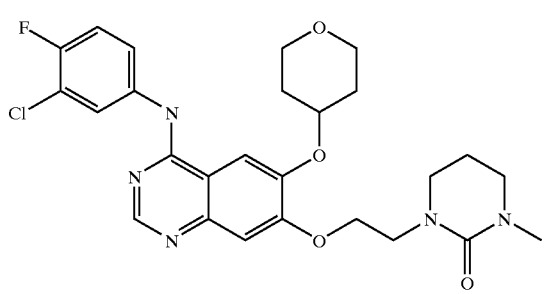 |
| (22) | 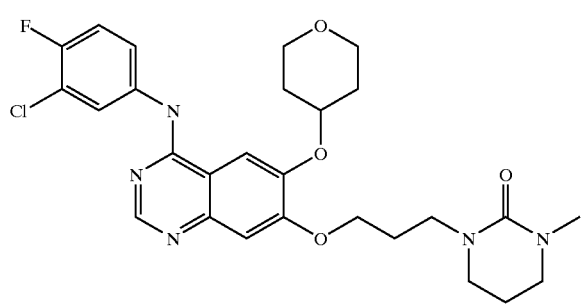 |
| (23) | 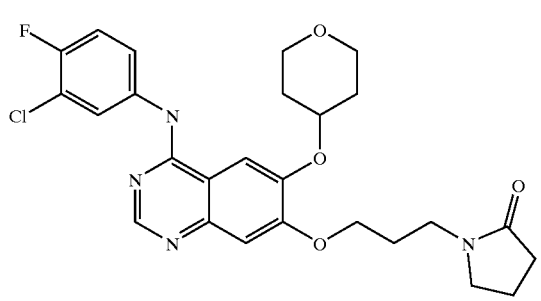 |
| (24) | 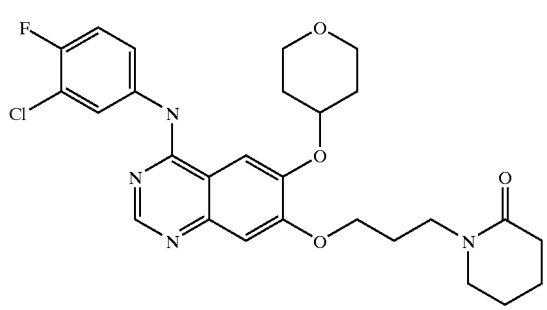 |

-continued
| Example No. | Structure |
|---|---|
| (25) | 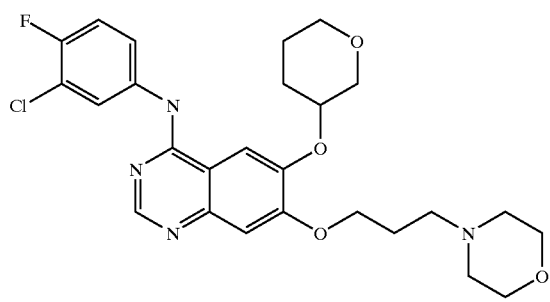 |
| (26) | 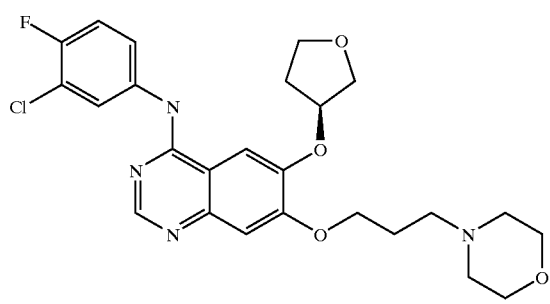 |
| (27) | 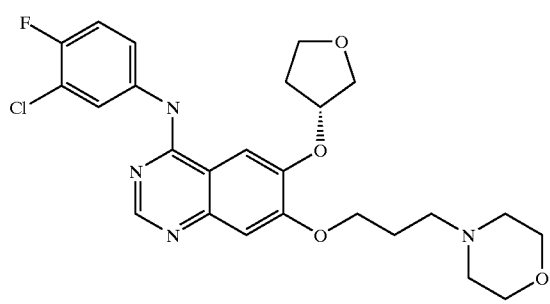 |
| (28) | 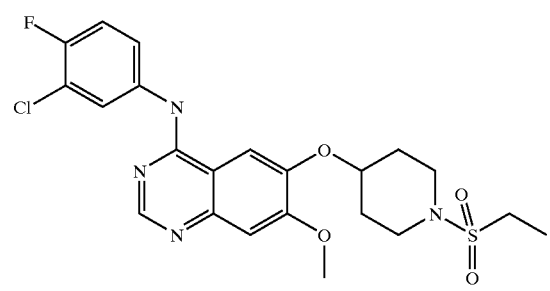 |
| (29) | 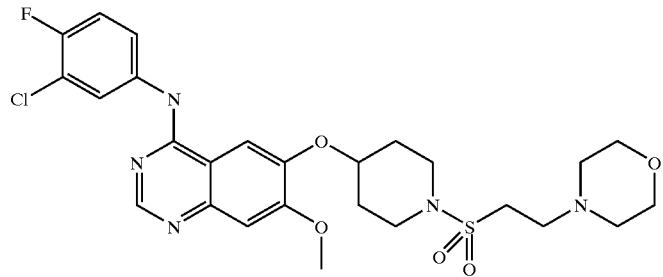 |

-continued
| Example No. | Structure |
|---|---|
| (30) | 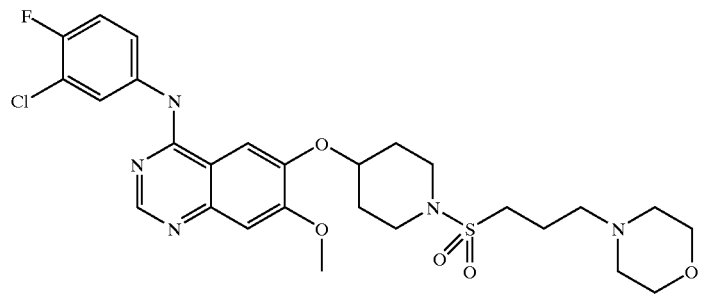 |
| (31) | 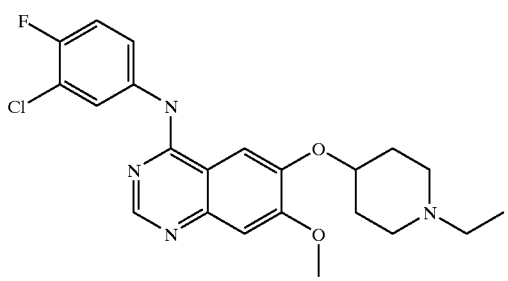 |
| (32) | 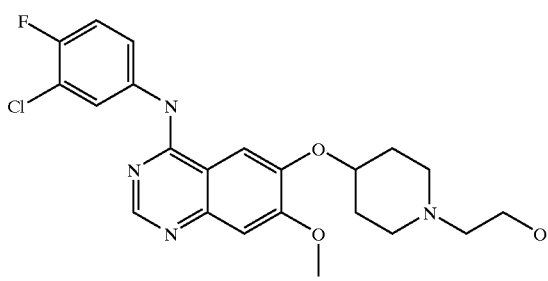 |
| (33) | 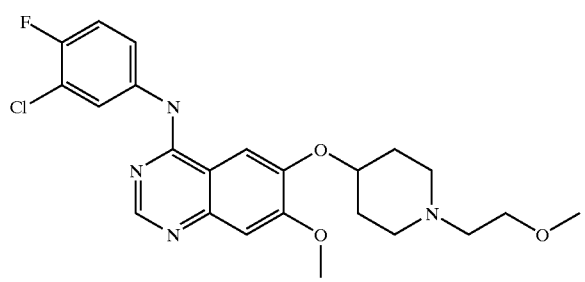 |
| (34) | 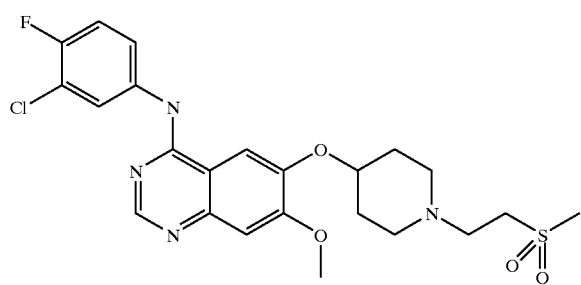 |

| Example No. | Structure |
|---|---|
| (35) | 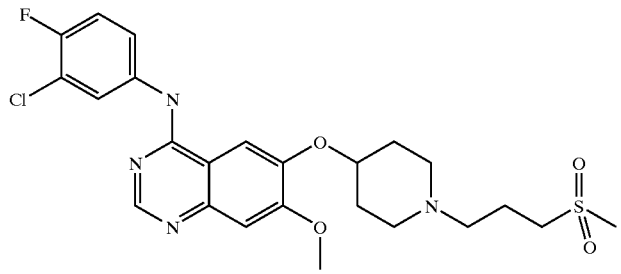 |
| (36) | 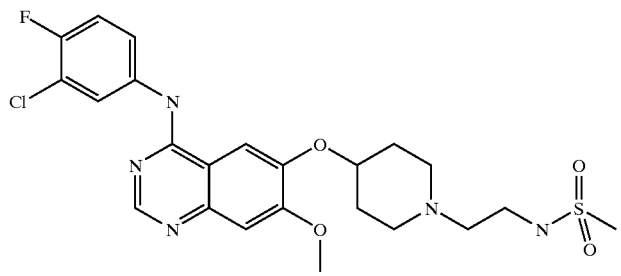 |
| (37) | 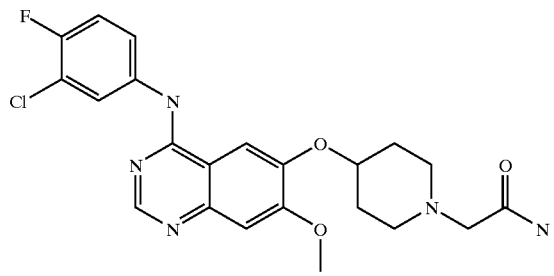 |
| (38) | 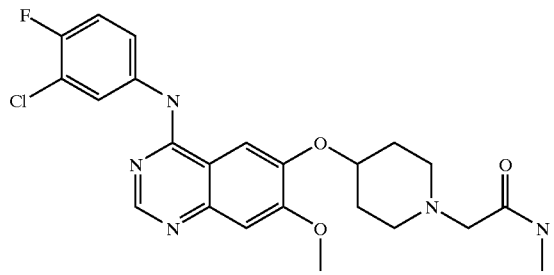 |
| (39) | 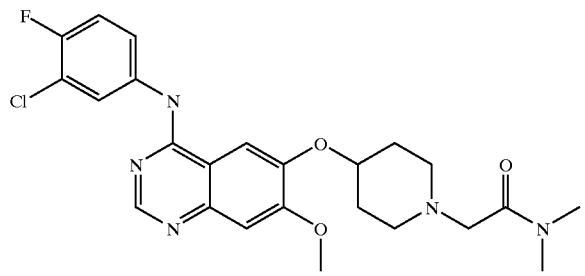 |

| Example No. | Structure |
|---|---|
| (40) | 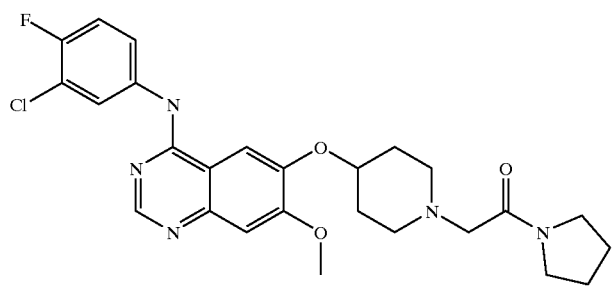 |
| (41) | 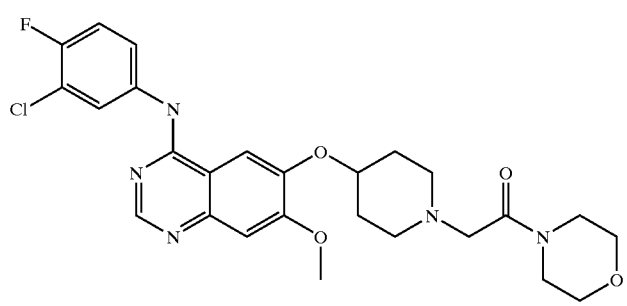 |
| (42) | 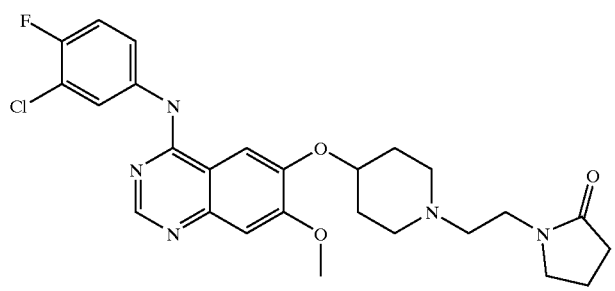 |
| (43) | 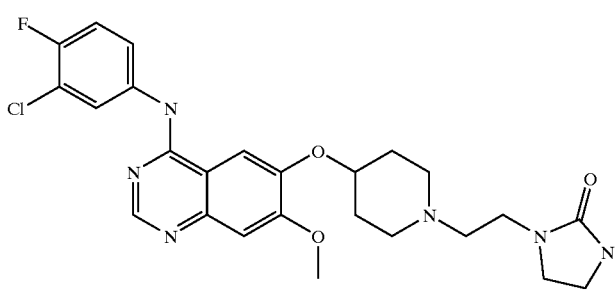 |
| (44) | 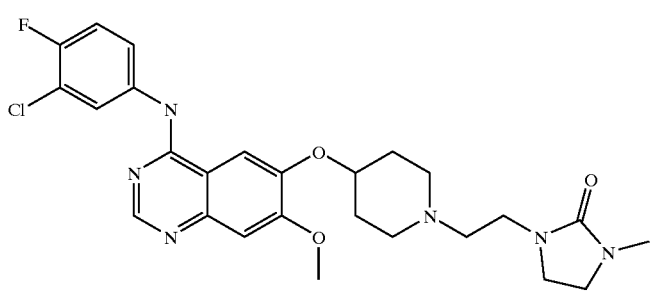 |

-continued

| Example No. | Structure |
|---|---|
| (45) | 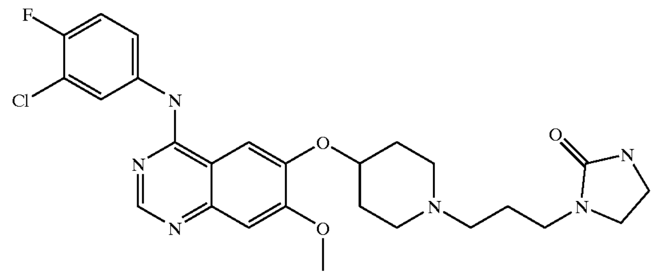 |
| (46) | 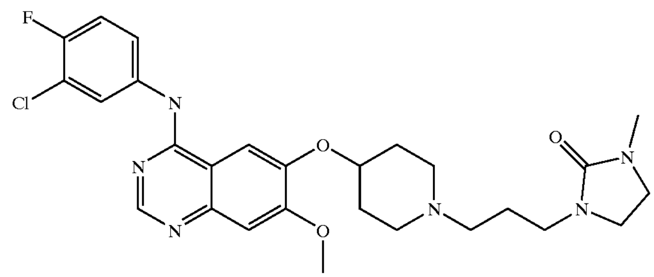 |
| (47) | 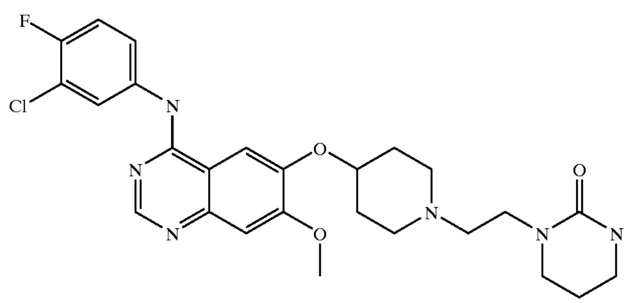 |
| (48) | 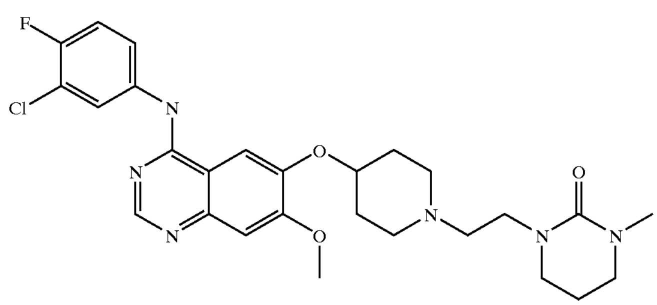 |
| (49) | 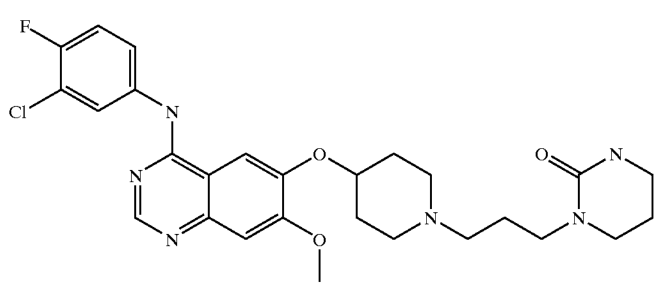 |

-continued
| Example No. | Structure |
|---|---|
| (50) | 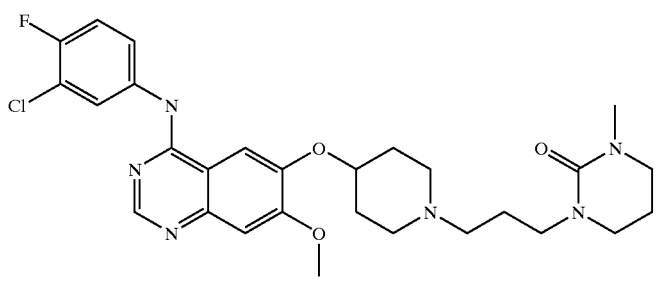 |
| (51) | 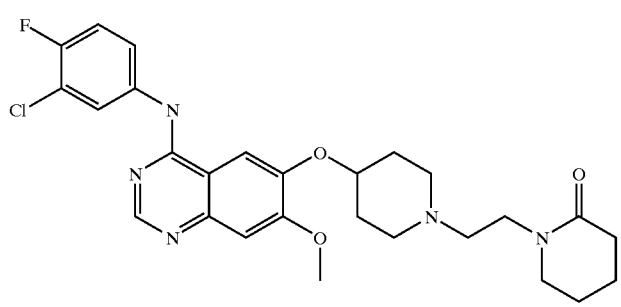 |
| (52) | 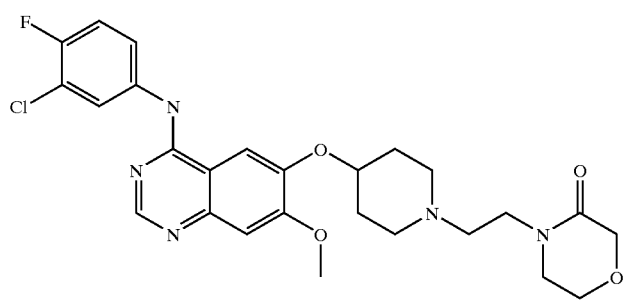 |
| (53) | 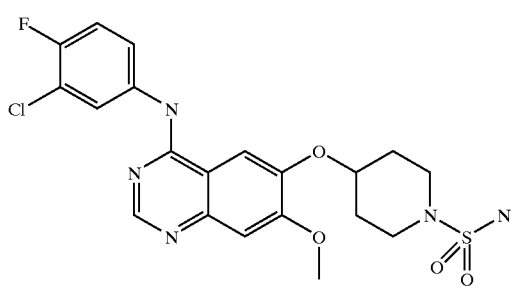 |
| (54) | 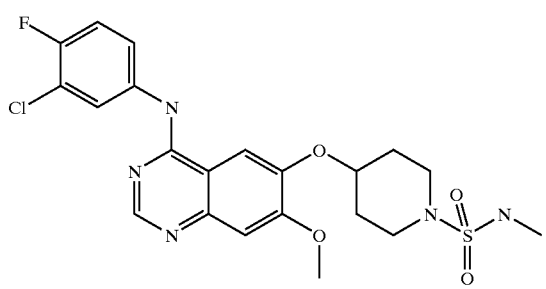 |

-continued
| Example No. | Structure |
|---|---|
| (55) | 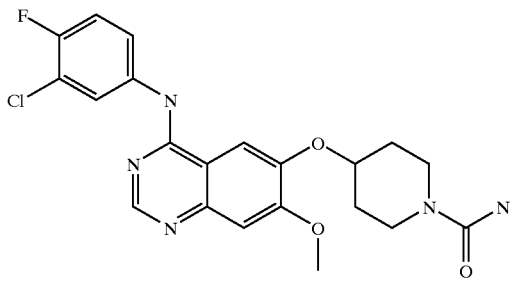 |
| (56) | 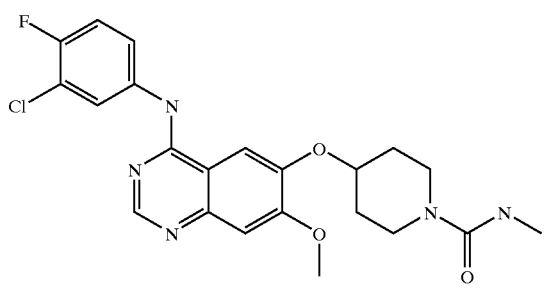 |
| (57) | 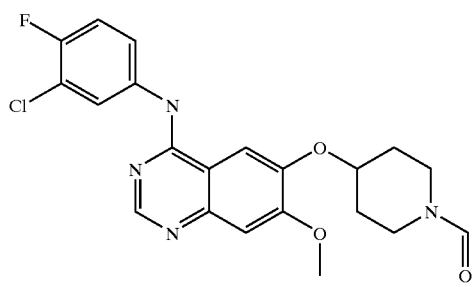 |
| (58) | 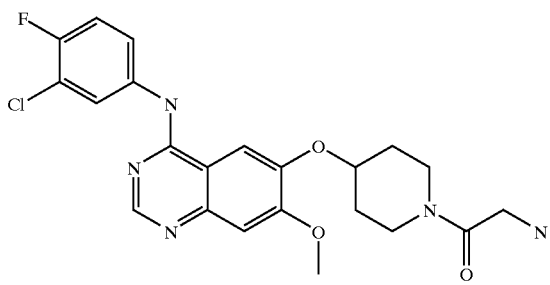 |
| (59) | 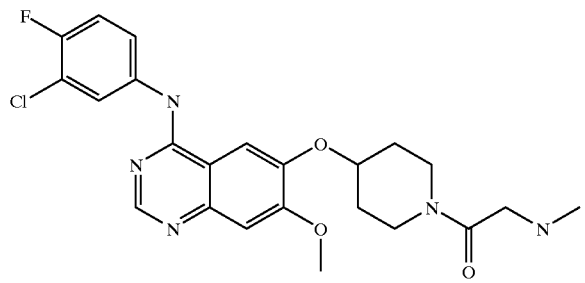 |

-continued
| Example No. | Structure |
|---|---|
| (60) | 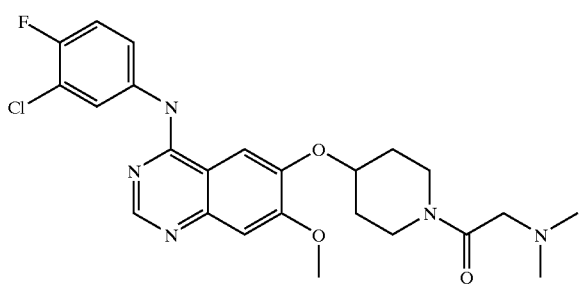 |
| (61) | 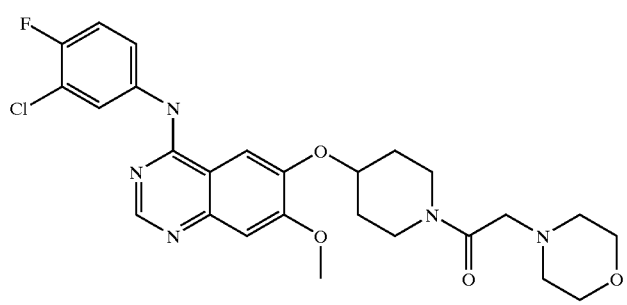 |
| (62) | 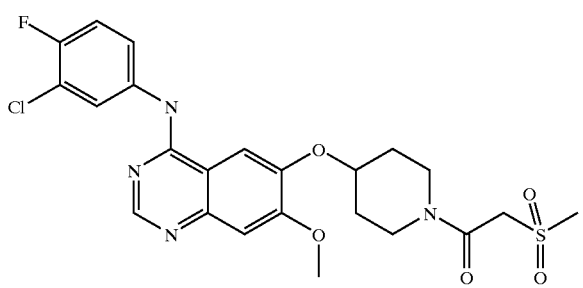 |
| (63) | 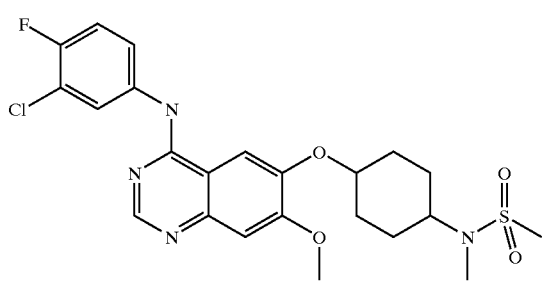 |
| (64) | 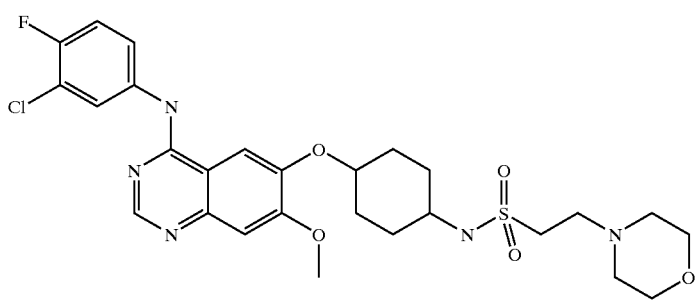 |

-continued
| Example No. | Structure |
|---|---|
| (65) | 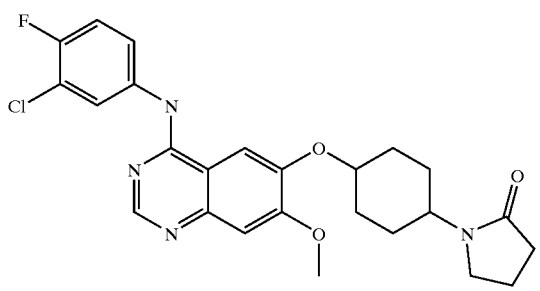 |
| (66) | 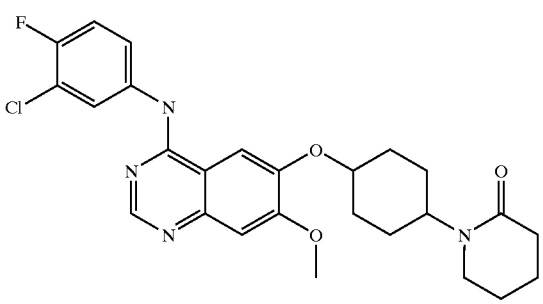 |
| (67) | 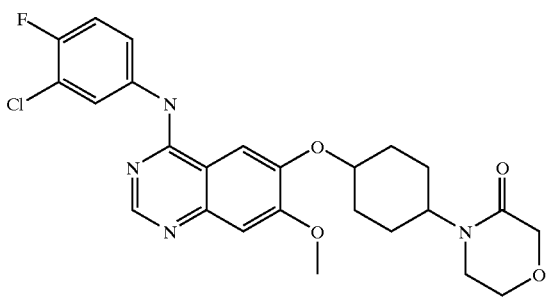 |
| (68) | 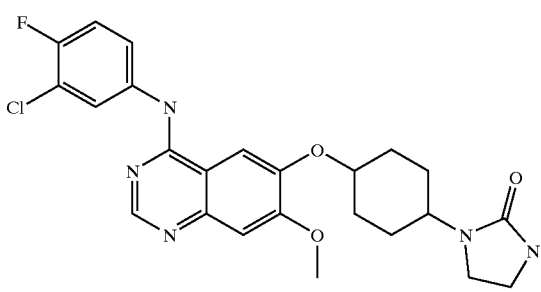 |
| (69) | 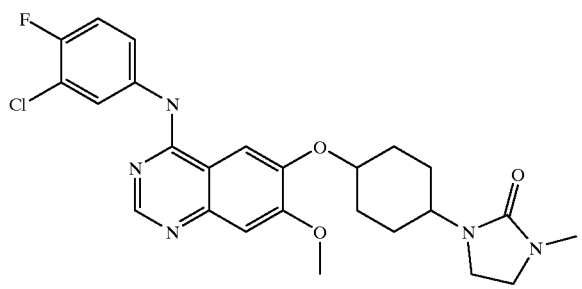 |

-continued
| Example No. | Structure |
|---|---|
| (70) | 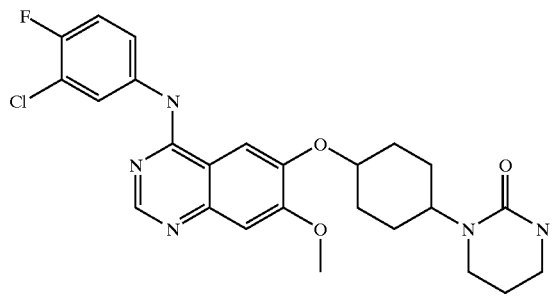 |
| (71) | 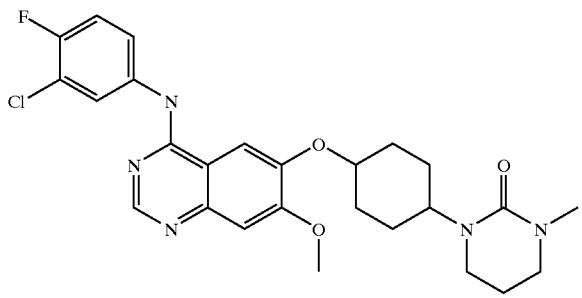 |
| (72) | 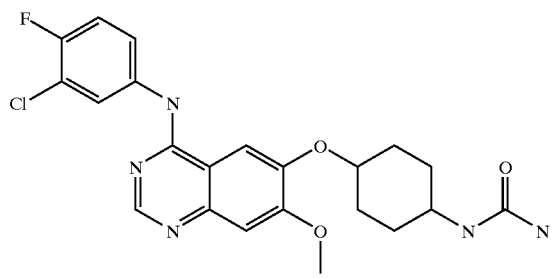 |
| (73) | 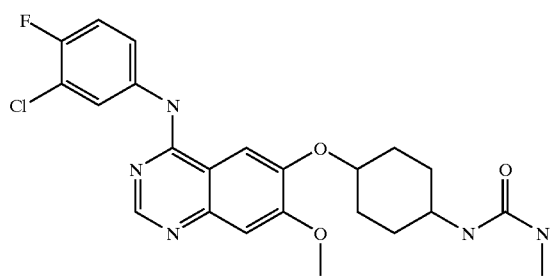 |
| (74) | 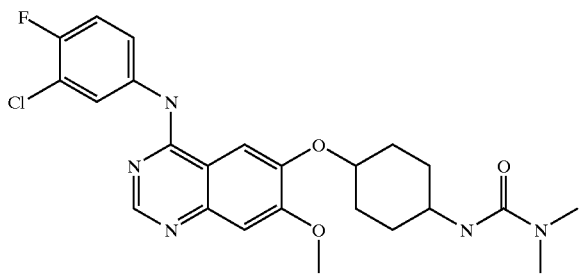 |

| Example No. | Structure |
|---|---|
| (75) | 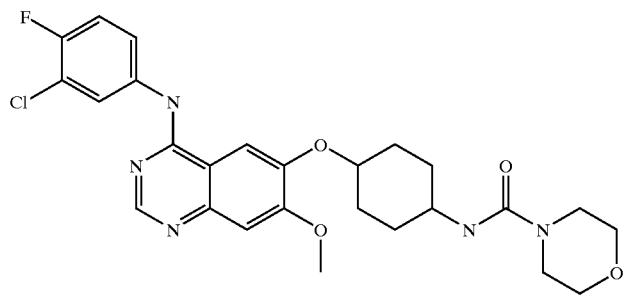 |
| (76) | 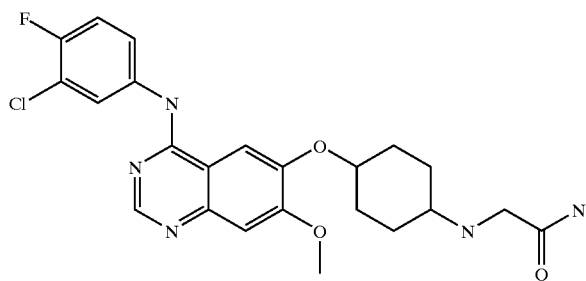 |
| (77) | 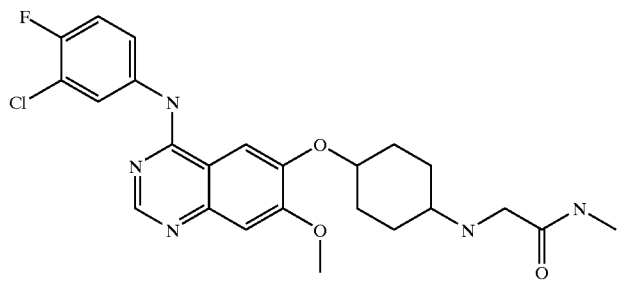 |
| (78) | 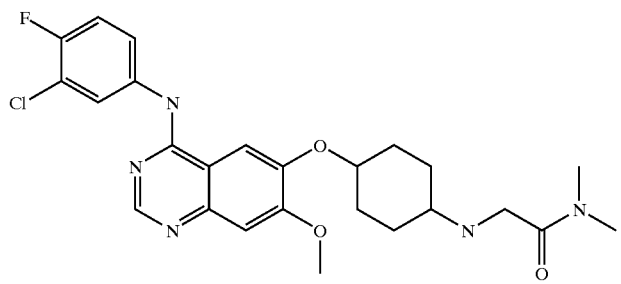 |
| (79) | 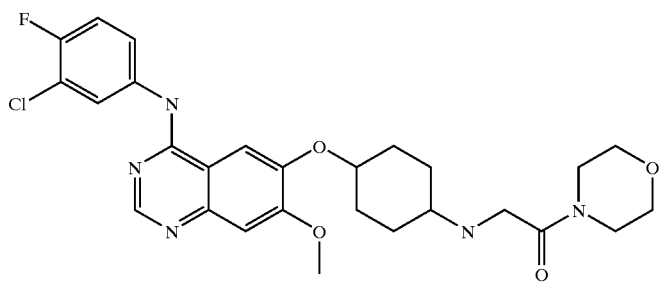 |

-continued

| Example No. | Structure |
|---|---|
| (80) | 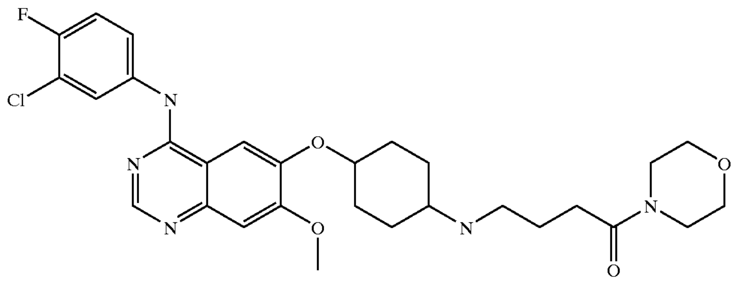 |
| (81) | 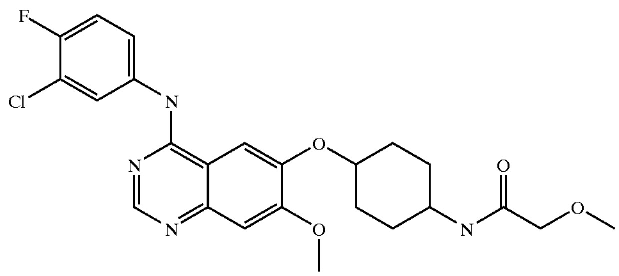 |
| (82) | 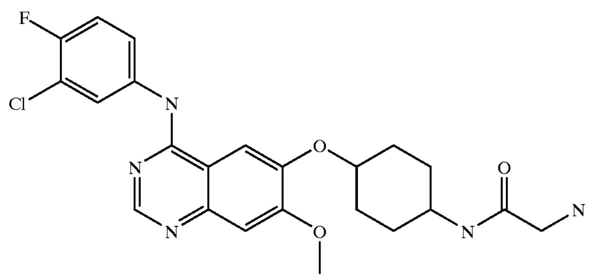 |
| (83) | 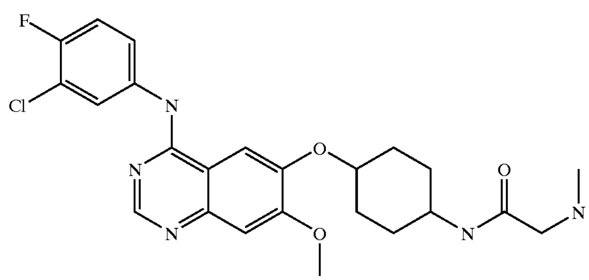 |
| (84) | 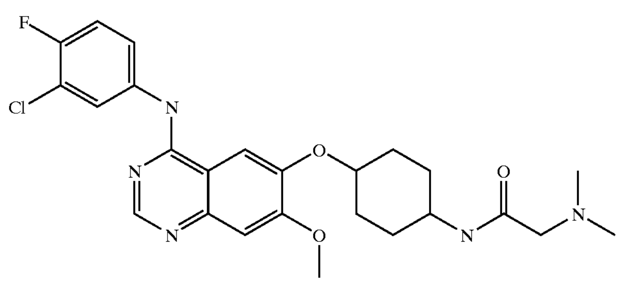 |

-continued
| Example No. | Structure |
|---|---|
| (85) | 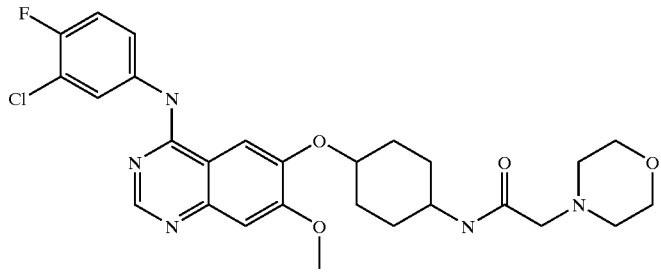 |
| (86) | 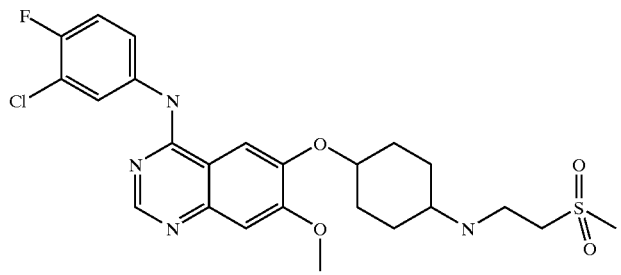 |
| (87) | 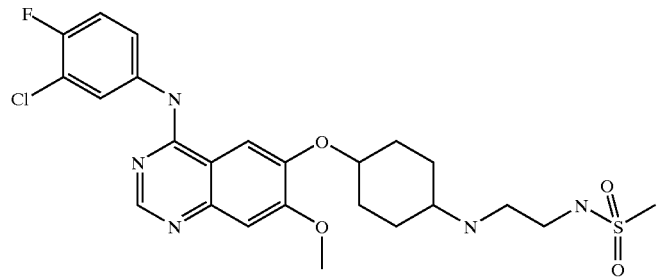 |
| (88) | 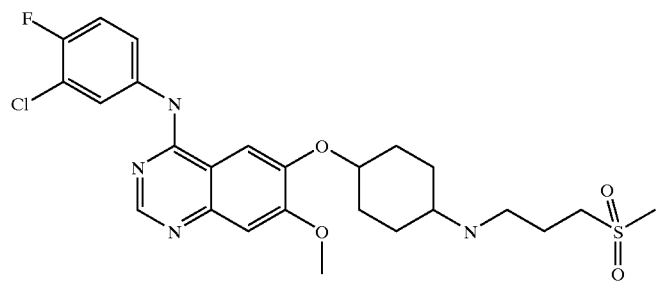 |
| (89) | 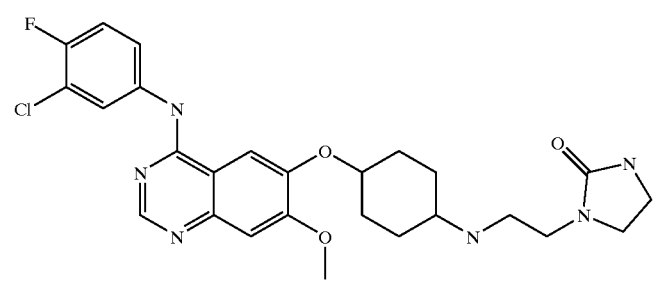 |

| Example No. | Structure |
|---|---|
| (90) | 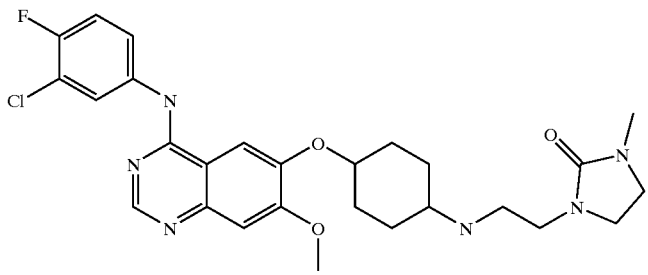 |
| (91) | 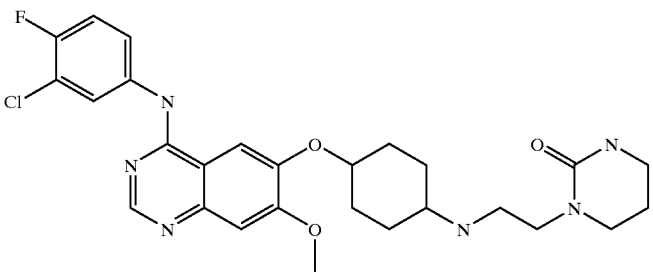 |
| (92) | 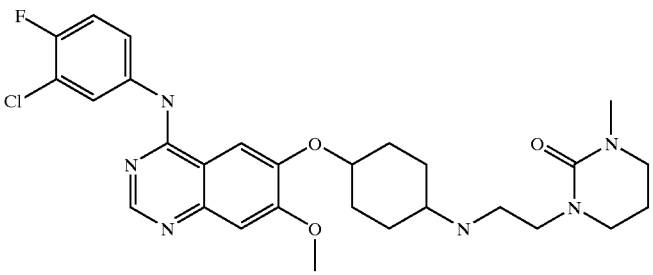 |
| (93) | 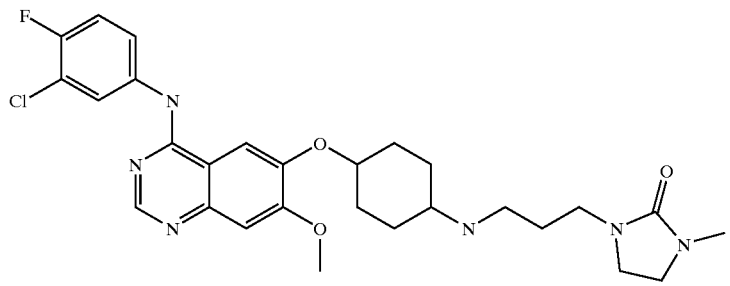 |
| (94) | 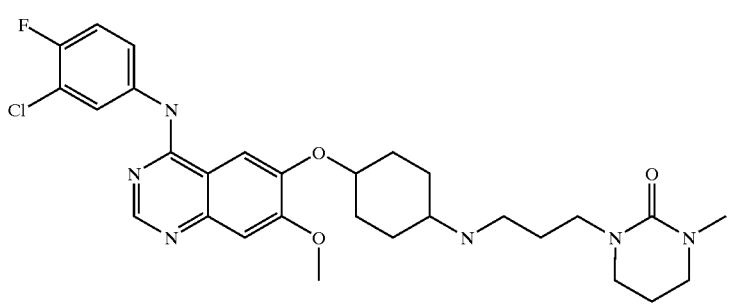 |

-continued
| Example No. | Structure |
|---|---|
| (95) | 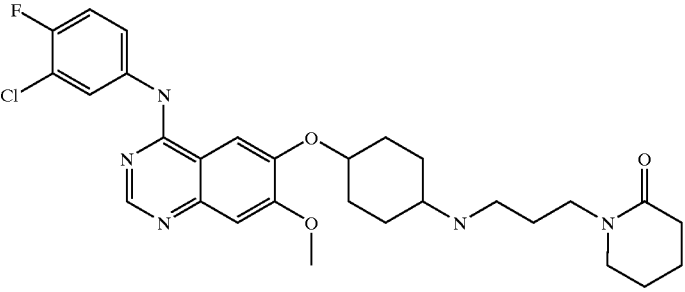 |
| (96) | 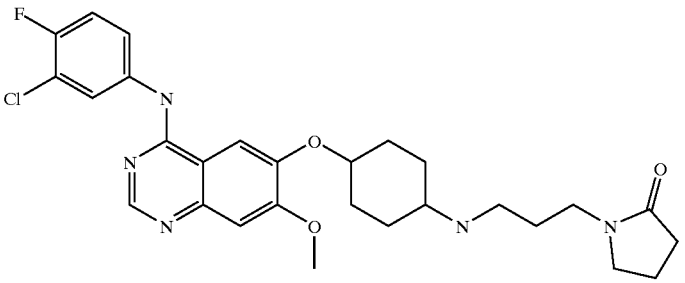 |
| (97) | 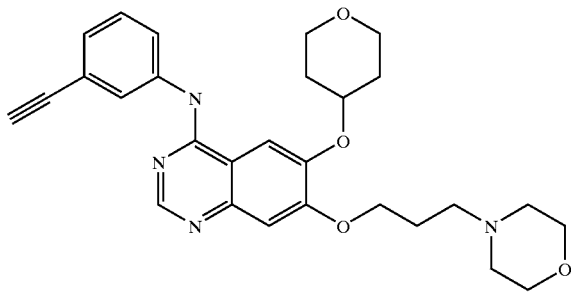 |
| (98) | 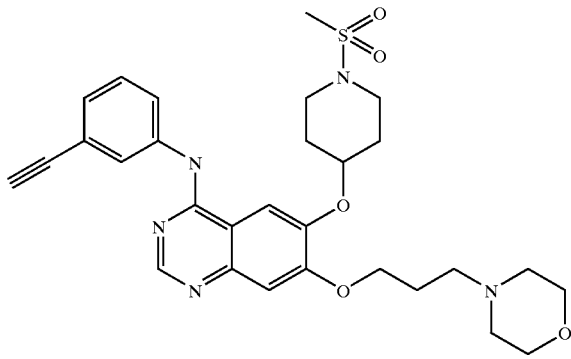 |
| (99) | 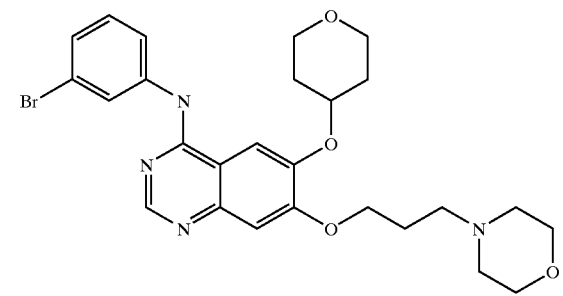 |

| Example No. | Structure |
|---|---|
| (100) | 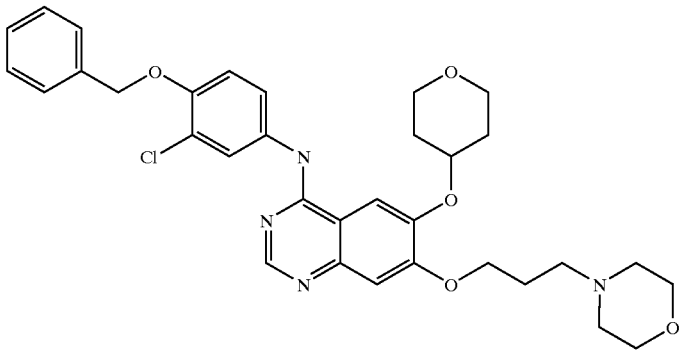 |
| (101) | 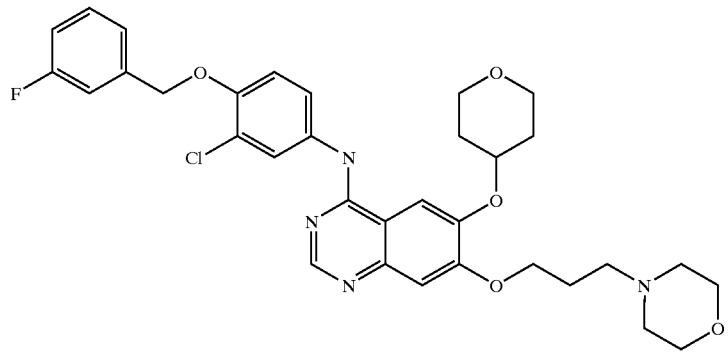 |
| (102) | 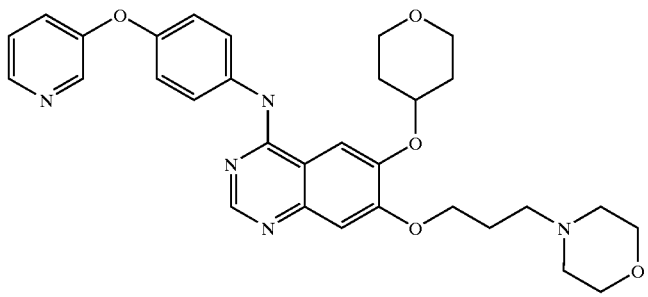 |
| (103) | 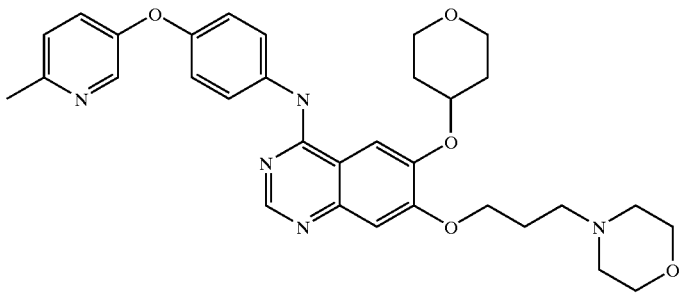 |

-continued
| Example No. | Structure |
|---|---|
| (104) | 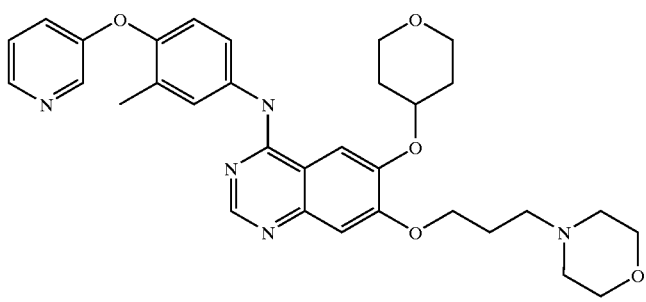 |
| (105) | 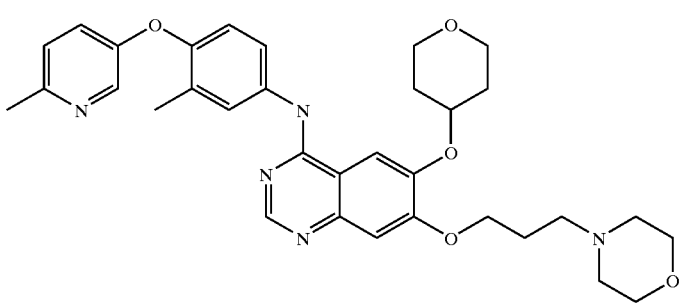 |
| (106) | 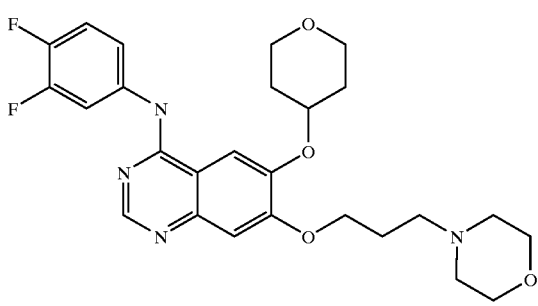 |
| (107) | 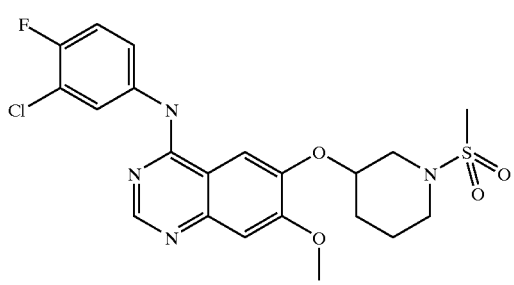 |
| (108) | 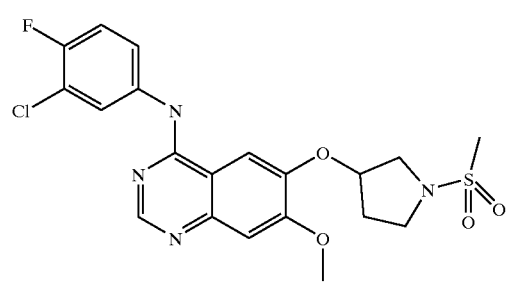 |

-continued

| Example No. | Structure |
|---|---|
| (109) | *[chemical structure: N-(3-chloro-4-fluorophenyl)-6-(tetrahydropyran-4-yloxy)quinazolin-4-amine]* |
| (110) | *[chemical structure: N-(3-chloro-4-fluorophenyl)-6-(1-methylpiperidin-4-yloxy)quinazolin-4-amine]* |
| (111) | *[chemical structure: N-(3-chloro-4-fluorophenyl)-6-[1-(methoxyacetyl)piperidin-4-yloxy]quinazolin-4-amine]* |
| (112) | *[chemical structure: N-(3-chloro-4-fluorophenyl)-6-[1-(morpholine-4-carbonyl)piperidin-4-yloxy]quinazolin-4-amine]* |
| (113) | *[chemical structure: N-(3-chloro-4-fluorophenyl)-6-(1-cyanopiperidin-4-yloxy)quinazolin-4-amine]* |
| (114) | *[chemical structure: N-(3-chloro-4-fluorophenyl)-6-(4-aminocyclohexyloxy)quinazolin-4-amine]* |

| Example No. | Structure |
|---|---|
| (115) | 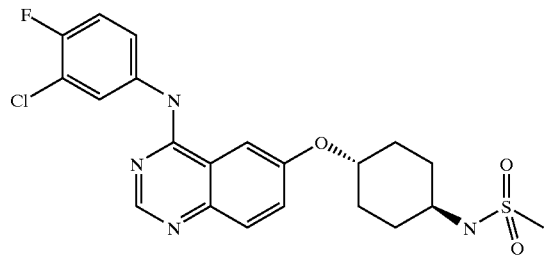 |
| (116) | 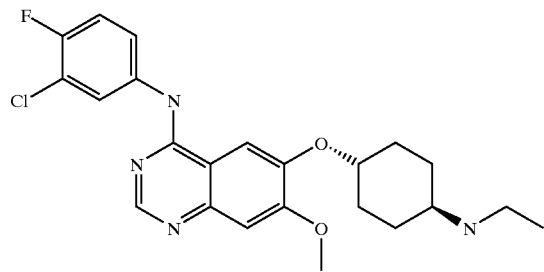 |
| (117) | 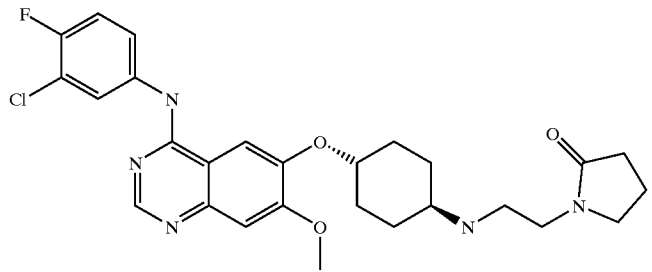 |
| (118) | 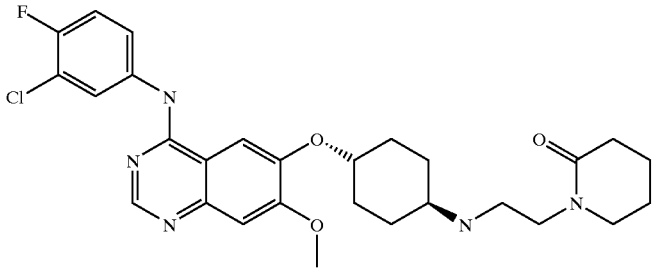 |
| (119) | 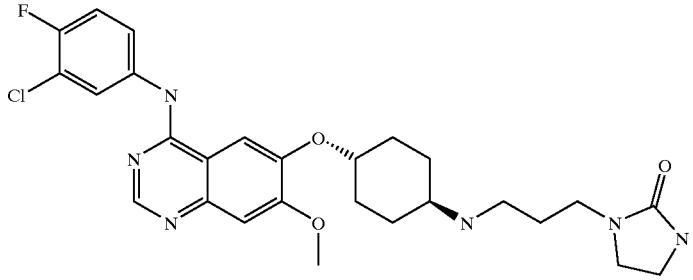 |

-continued
| Example No. | Structure |
|---|---|
| (120) | 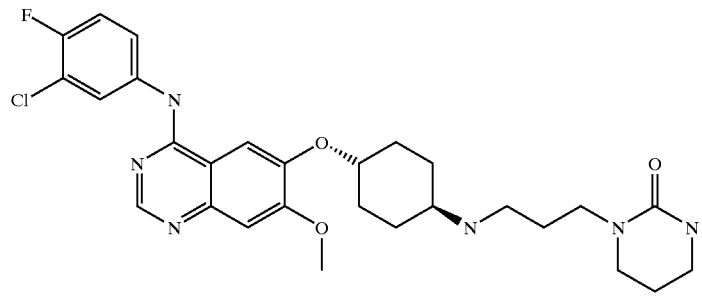 |
| (121) | 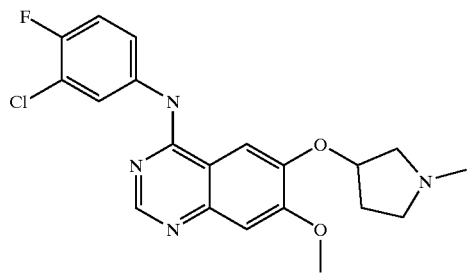 |
| (122) | 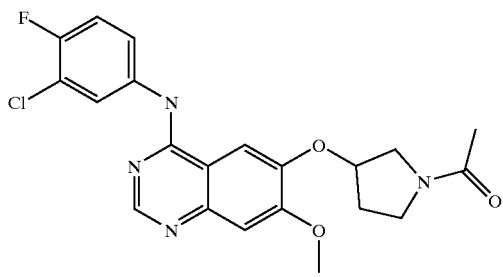 |
| (123) | 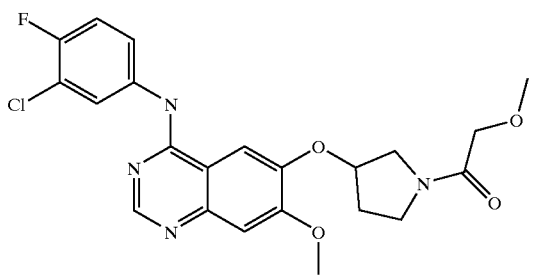 |
| (124) | 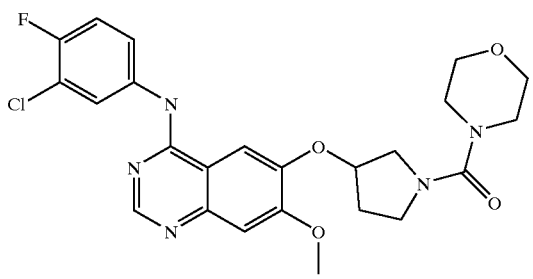 |

| Example No. | Structure |
|---|---|
| (125) | 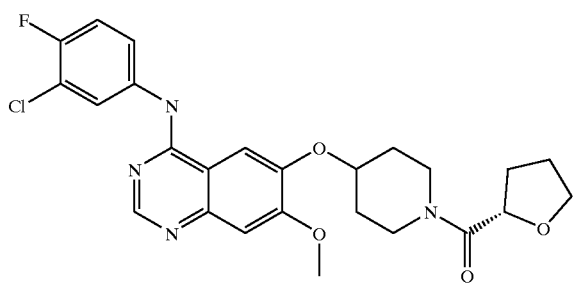 |
| (126) | 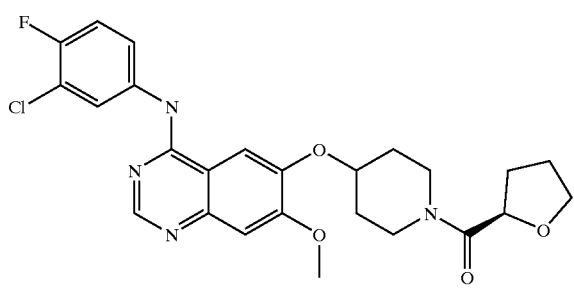 |
| (127) | 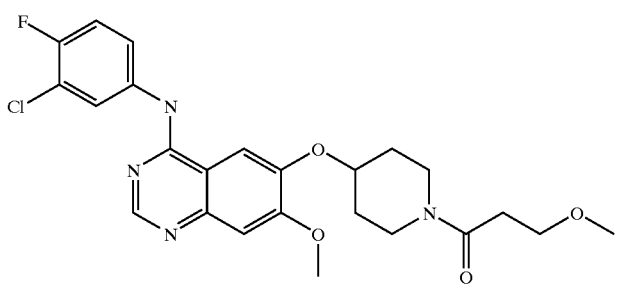 |
| (128) | 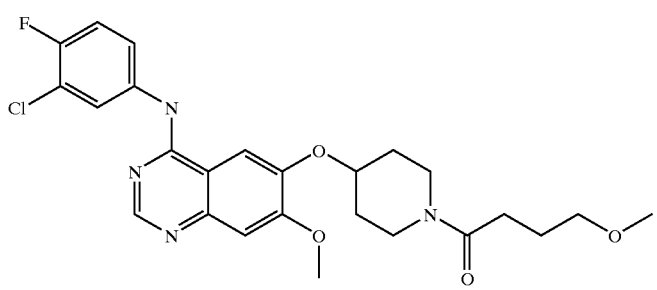 |
| (129) | 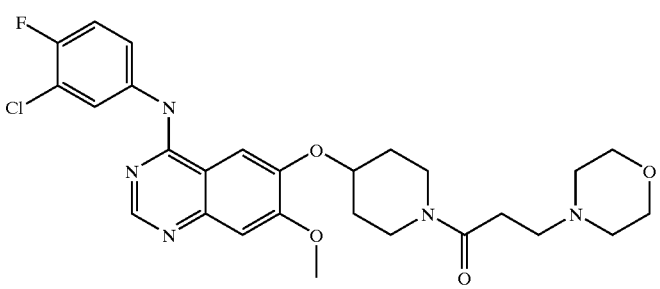 |

| Example No. | Structure |
|---|---|
| (130) | 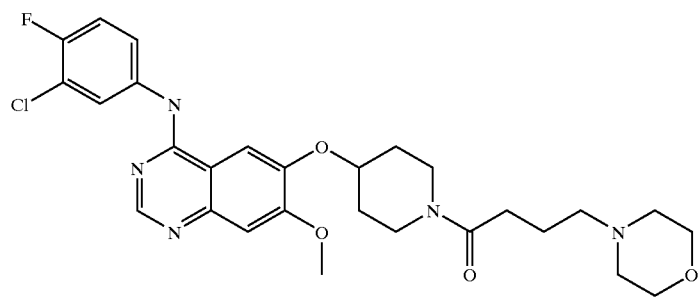 |
| (131) | 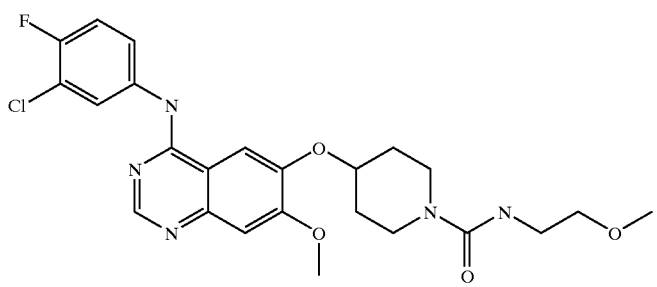 |
| (132) | 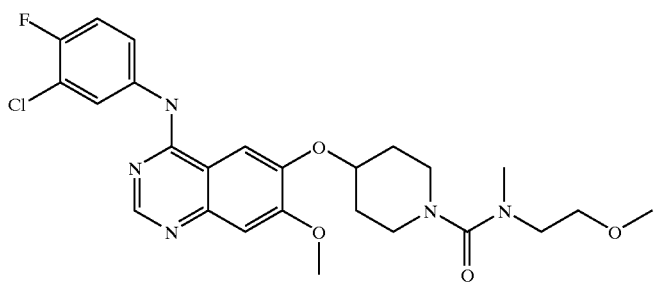 |
| (133) | 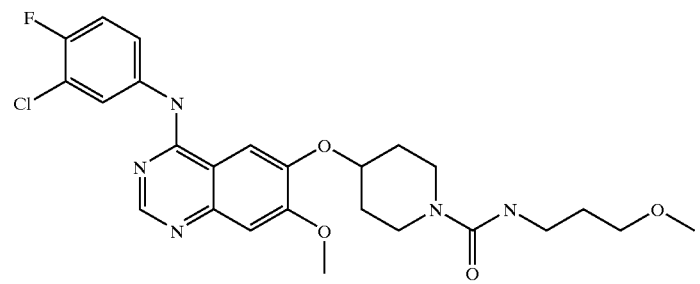 |
| (134) | 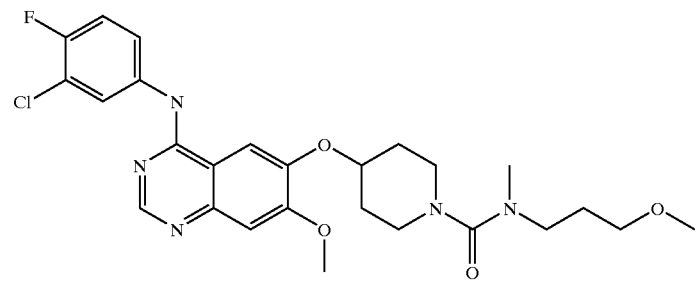 |

-continued
| Example No. | Structure |
|---|---|
| (135) | 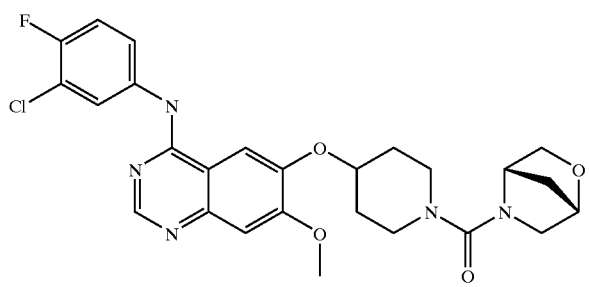 |
| (136) | 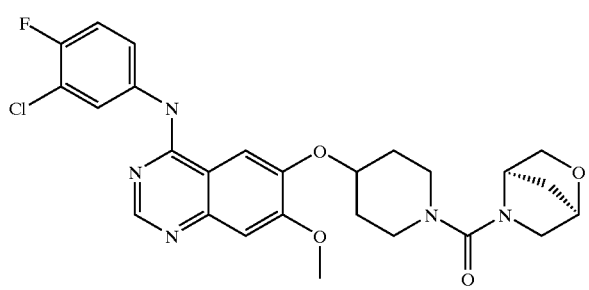 |
| (137) | 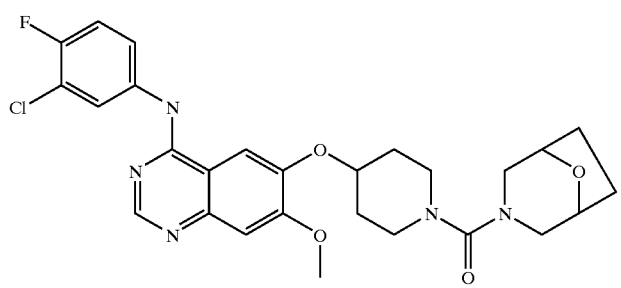 |
| (138) | 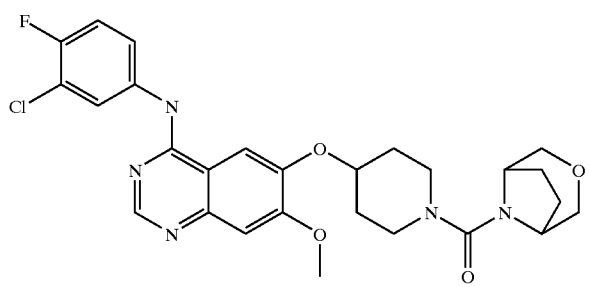 |
| (139) | 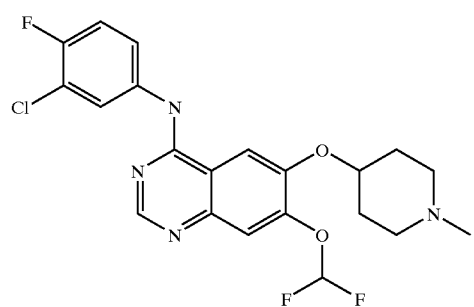 |

| Example No. | Structure |
|---|---|
| (140) | 4-({[4-(3-chloro-4-fluoroanilino)-7-methoxyquinazolin-6-yl]oxy}piperidin-1-yl)-3-(morpholin-4-yl)-3-oxopropyl structure |
| (141) | 4-({[4-(3-chloro-4-fluoroanilino)-7-methoxyquinazolin-6-yl]oxy}piperidin-1-yl)-4-(morpholin-4-yl)-4-oxobutyl structure |
| (142) | 4-(3-chloro-4-fluoroanilino)-7-methoxy-6-[(1-propylpiperidin-4-yl)oxy]quinazoline |
| (143) | 4-(3-chloro-4-fluoroanilino)-6-[(1-isopropylpiperidin-4-yl)oxy]-7-methoxyquinazoline |
| (144) | 4-(3-chloro-4-fluoroanilino)-7-methoxy-6-{[1-(3-methoxypropyl)piperidin-4-yl]oxy}quinazoline |

-continued

| Example No. | Structure |
|---|---|
| (145) | 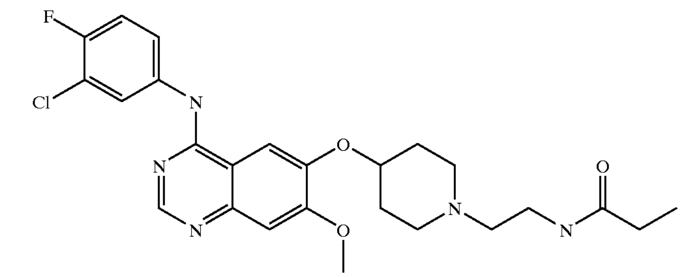 |
| (146) | 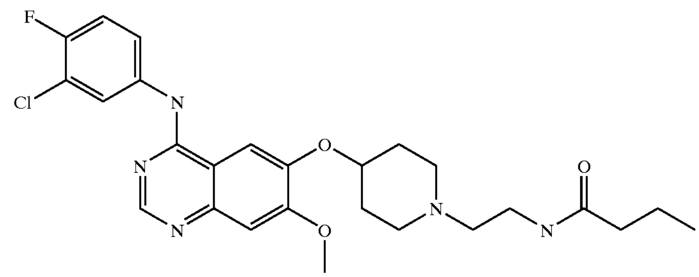 |
| (147) | 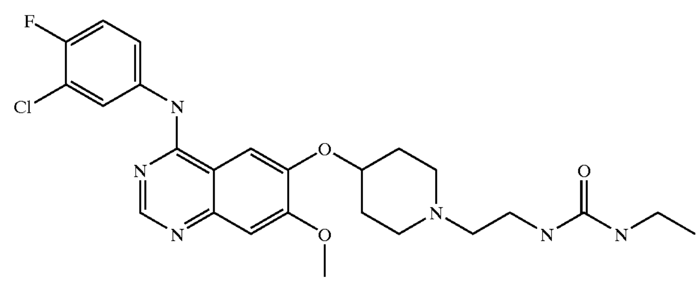 |
| (148) | 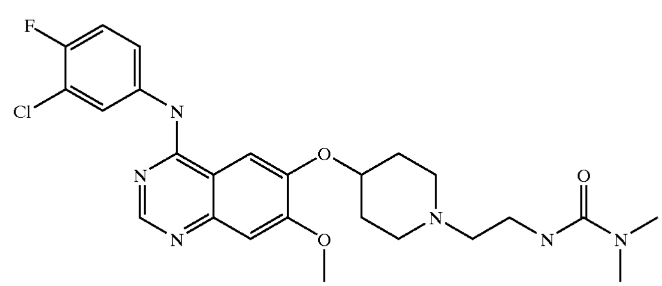 |
| (149) | 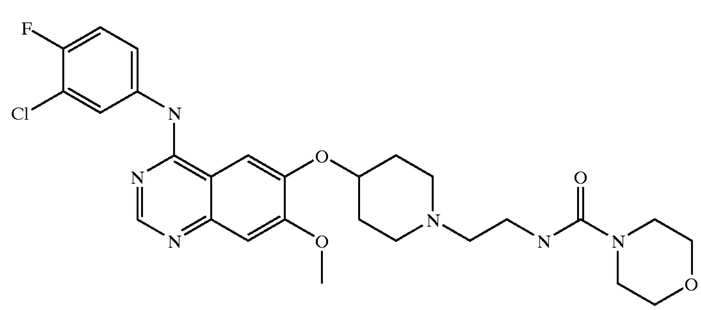 |

-continued
| Example No. | Structure |
|---|---|
| (150) | 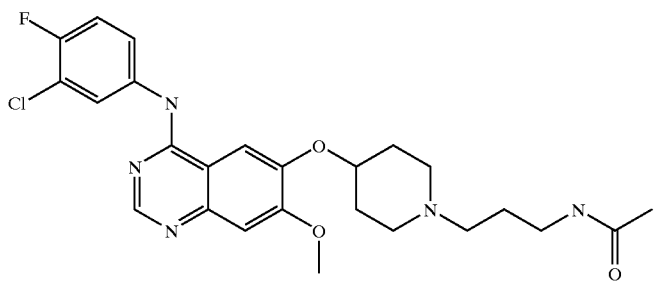 |
| (151) | 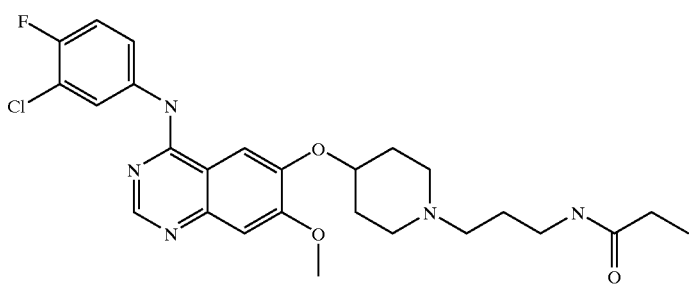 |
| (152) | 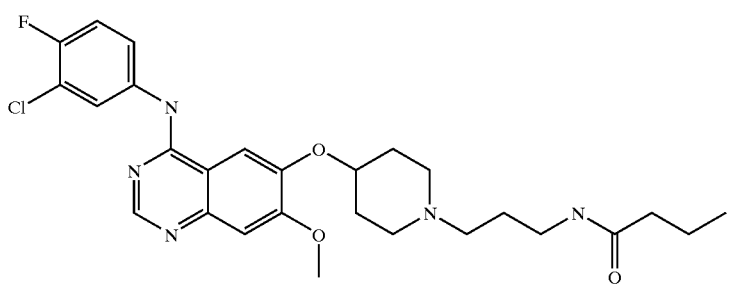 |
| (153) | 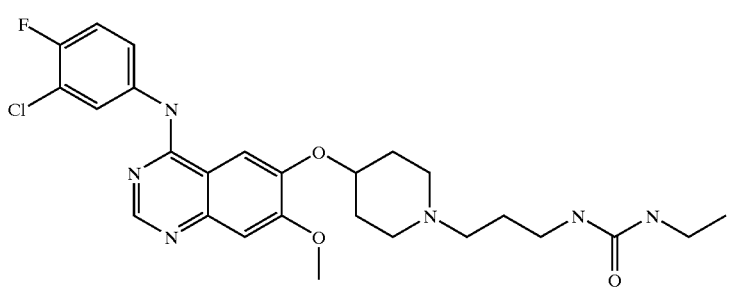 |
| (154) | 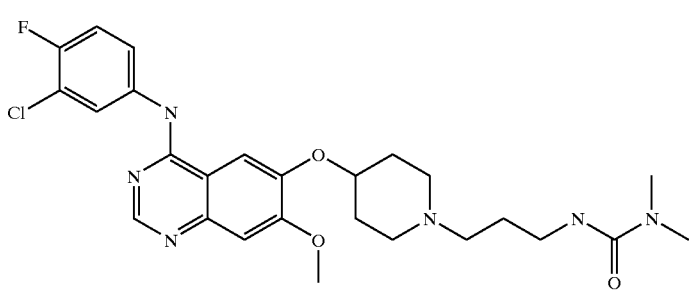 |

| Example No. | Structure |
|---|---|
| (156) | 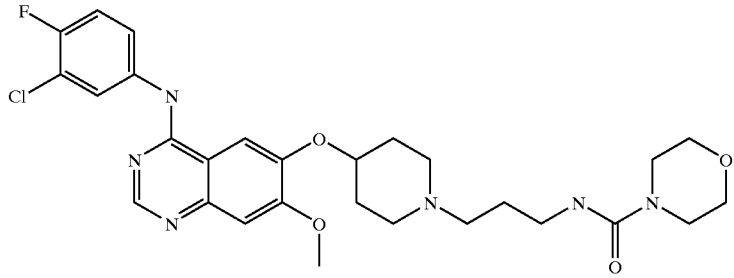 |
| (157) | 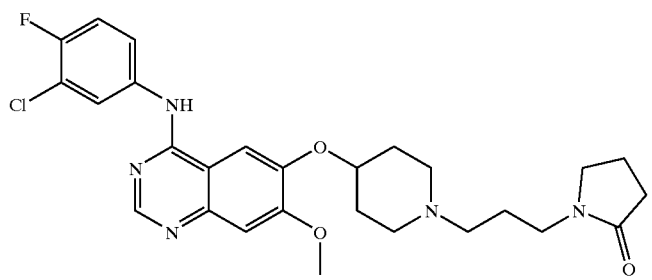 |
| (158) | 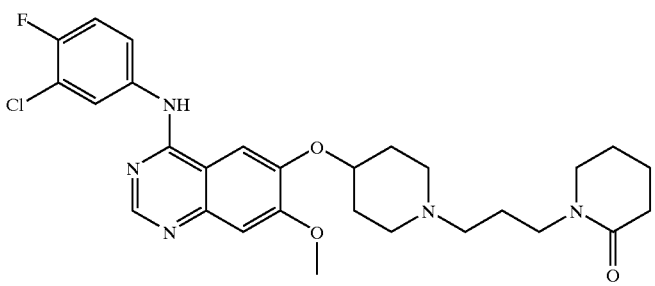 |
| (159) | 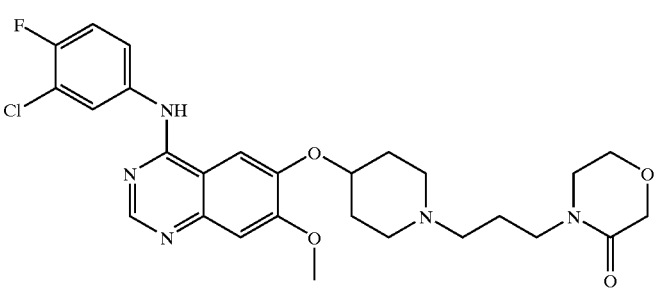 |
| (160) | 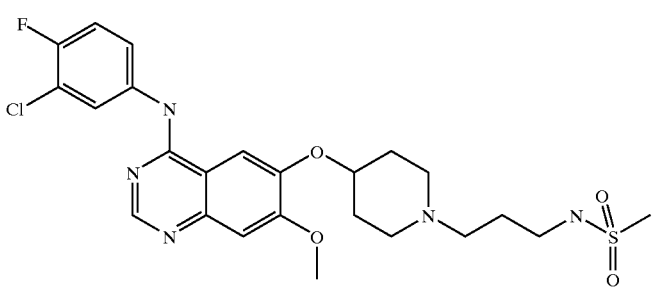 |

-continued
| Example No. | Structure |
|---|---|
| (161) | 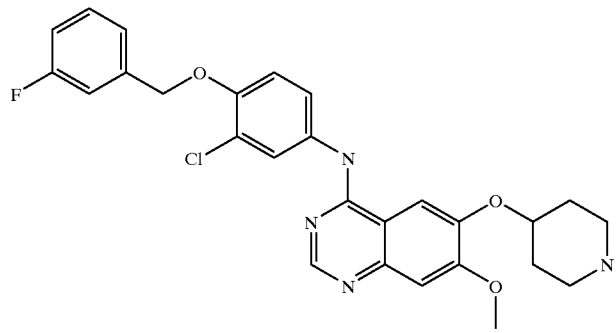 |
| (162) | 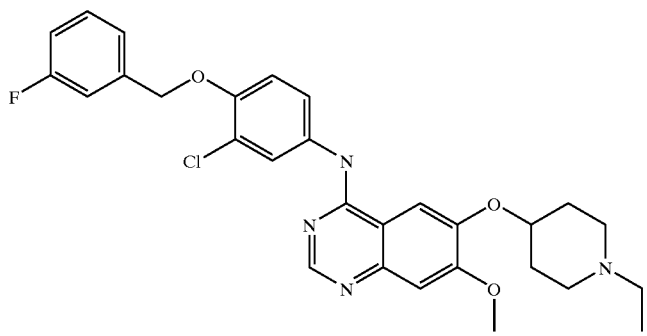 |
| (163) | 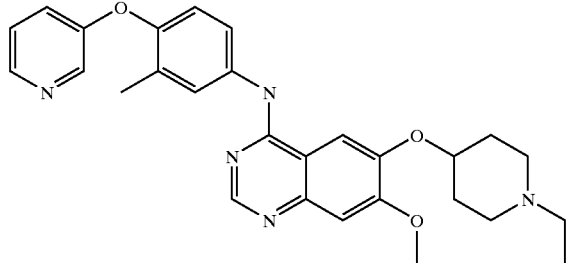 |
| (164) | 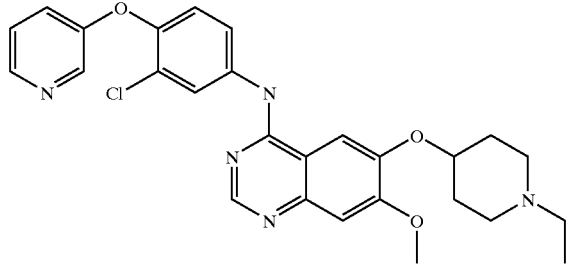 |
| (165) | 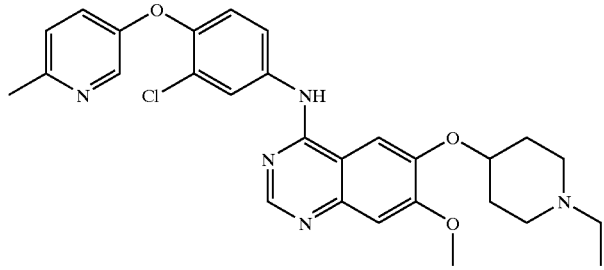 |

| Example No. | Structure |
|---|---|
| (166) | 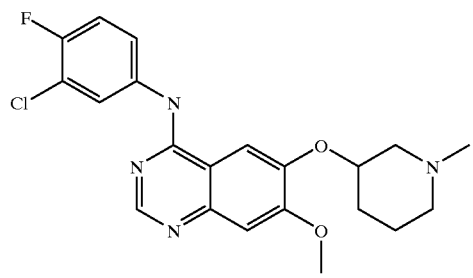 |
| (167) | 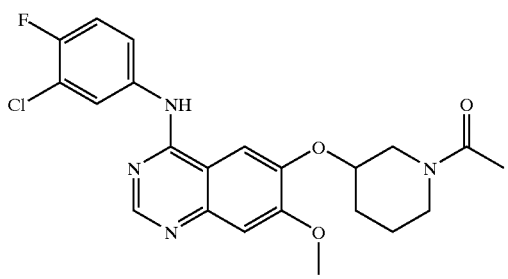 |
| (168) | 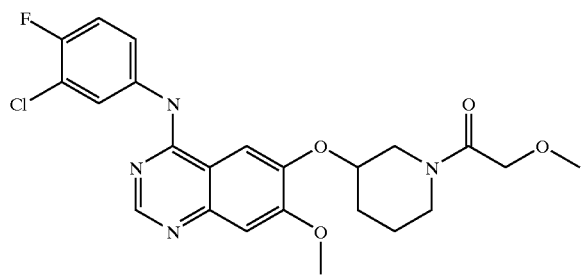 |
| (169) | 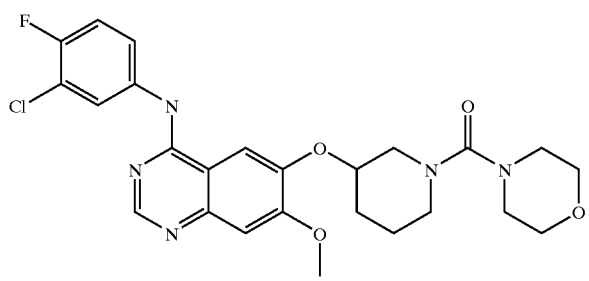 |
| (170) | 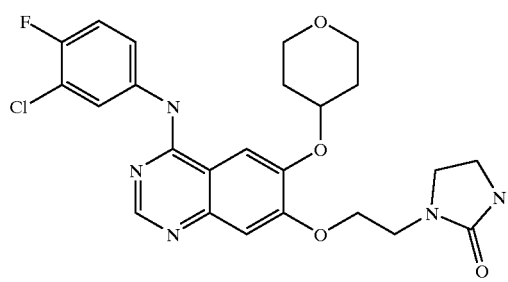 |

-continued
| Example No. | Structure |
|---|---|
| (171) | 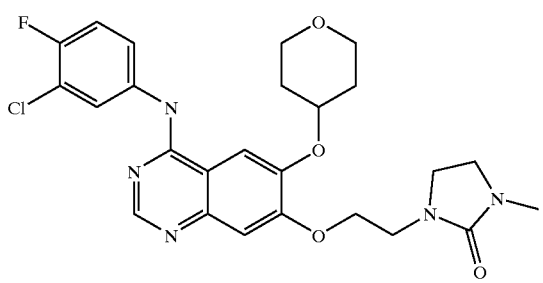 |
| (172) | 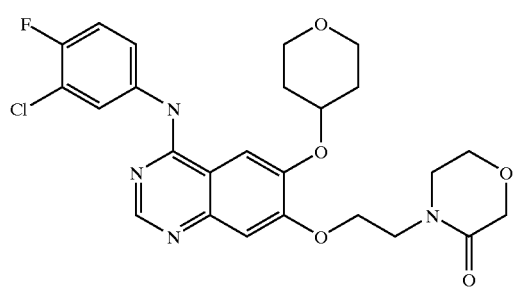 |
| (173) | 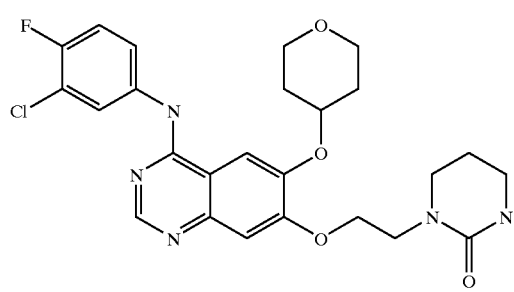 |
| (174) | 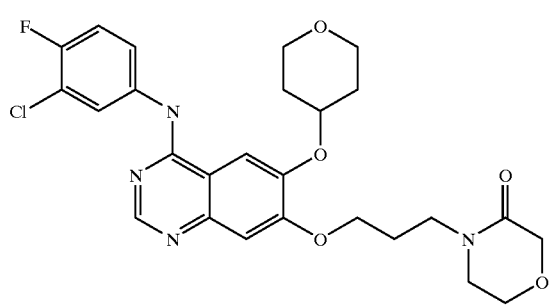 |
| (175) | 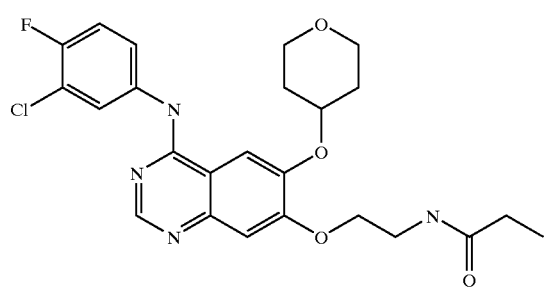 |

-continued
| Example No. | Structure |
|---|---|
| (176) | 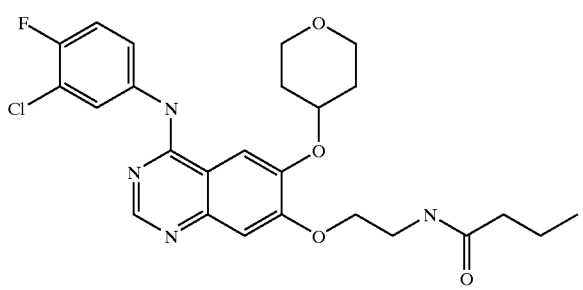 |
| (178) | 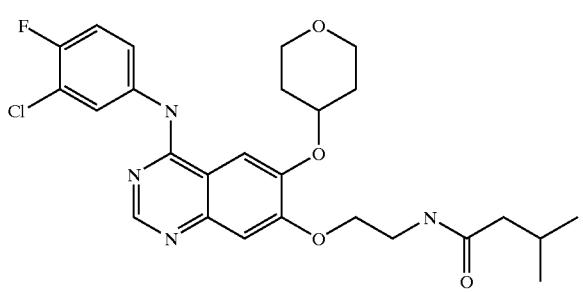 |
| (179) | 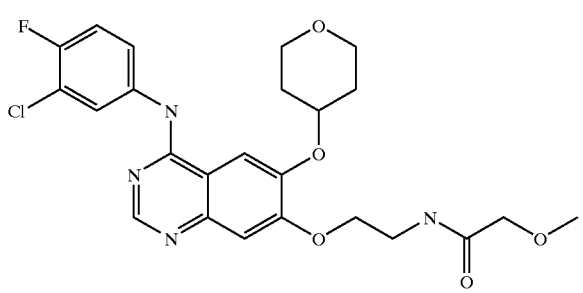 |
| (180) | 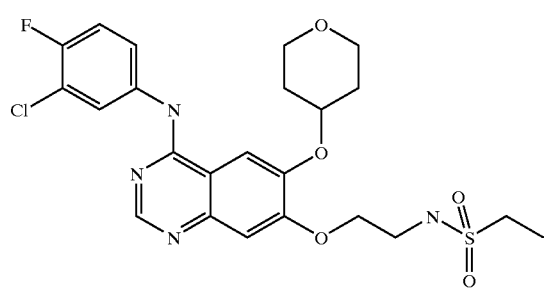 |
| (181) | 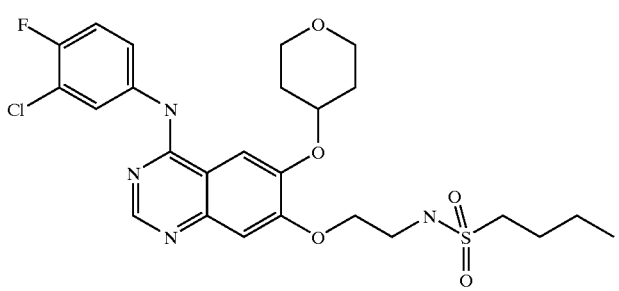 |

-continued
| Example No. | Structure |
|---|---|
| (182) | 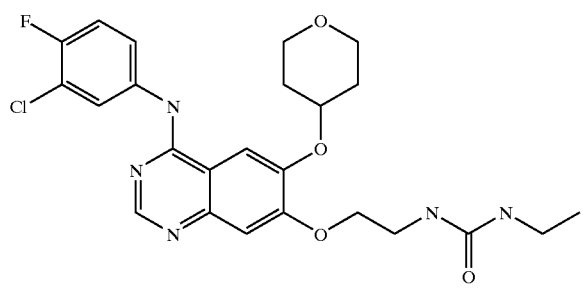 |
| (183) | 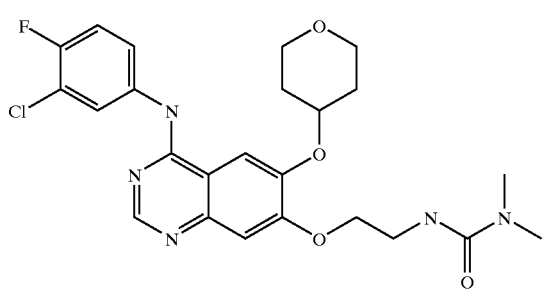 |
| (184) | 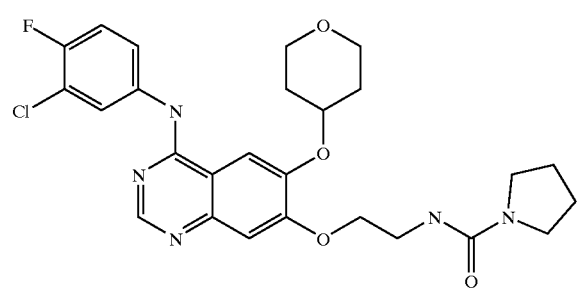 |
| (185) | 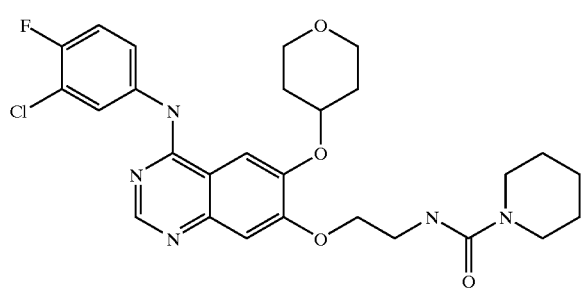 |
| (186) | 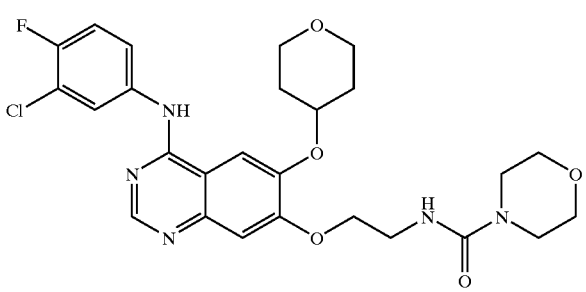 |

EXAMPLE 16

Coated Tablets Containing 75 mg of Active Substance

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| Weight of core: | 230 mg |
|---|---|
| die: | 9 mm, convex |

The tablet cores thus produced are coated with a film consisting essentially of hydroxypropylmethylcellulose. The finished film-coated tablets are polished with beeswax.

| Weight of coated tablet: | 245 mg. |
|---|---|

EXAMPLE 17

Tablets Containing 100 mg of Active Substance

| Composition: 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| Weight of tablet: | 220 mg |
|---|---|
| Diameter: | 10 mm, biplanar, facetted on both sides and notched on one side. |

EXAMPLE 18

Tablets Containing 150 mg of Active Substance

| Composition: 1 tablet contains: | |
|---|---|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
|---|---|
| die: | 10 mm, flat |

EXAMPLE 19

Hard Gelatine Capsules Containing 150 mg of Active Substance

| 1 capsule contains: | | |
|---|---|---|
| active substance | | 50.0 mg |
| corn starch (dried) | approx. | 80.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| Capsule filling: | approx. 320 mg |
|---|---|
| Capsule shell: | size 1 hard gelatine capsule. |

EXAMPLE 20

Suppositories Containing 150 mg of Active Substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2000.0 mg |

Preparation:

After the suppository mass has been melted the active substance is homogeneously distributed therein and the melt is poured into chilled moulds.

EXAMPLE 21

Suspension Containing 50 mg of Active Substance

| 100 ml of suspension contain: | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 22

Ampoules Containing 10 mg Active Substance

| Composition: | |
|---|---|
| active substance | 10.0 mg |
| 0.01 N hydrochloric acid q.s. | 2.0 ml |
| double-distilled water | |

Preparation:

The active substance is dissolved in the necessary amount of 0.01 N HCl, made isotonic with common salt, filtered sterile and transferred into 2 ml ampoules.

EXAMPLE 23

Ampoules Containing 50 mg of Active Substance

| Composition: | |
|---|---|
| active substance | 50.0 mg |
| 0.01 N hydrochloric acid q.s. | 10.0 ml |
| double-distilled water | |

Preparation:

The active substance is dissolved in the necessary amount of 0.01 N HCl, made isotonic with common salt, filtered sterile and transferred into 10 ml ampoules.

EXAMPLE 24

Capsules for Powder Inhalation Containing 5 mg of Active Substance

| 1 capsule contains: | |
|---|---|
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

| weight of capsule: | 70.0 mg |
|---|---|
| size of capsule = | 3 |

EXAMPLE 25

Inhalable Solution for Hand-held Nebulisers Containing 2.5 mg Active Substance

| 1 spray contains: | |
|---|---|
| active substance | 2.500 mg |
| benzalkonium chloride | 0.001 mg |
| 1 N hydrochloric acid q.s. | 15.000 mg |
| ethanol/water (50/50) | |

Preparation:

The active substance and benzalkonium chloride are dissolved in ethanol/water (50/50). The pH of the solution is adjusted with 1 N hydrochloric acid. The resulting solution is filtered and transferred into suitable containers for use in hand-held nebulisers (cartridges).

| Contents of the container: | 4.5 g |
|---|---|

We claim:
1. A compound of the general formula

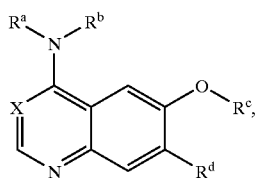

(I)

wherein
$R^a$ denotes a hydrogen atom or a $C_{1-4}$-alkyl group,
$R^b$ denotes a phenyl or 1-phenylethyl group, wherein the phenyl nucleus is substituted in each case by the groups $R^1$ to $R^3$, while
$R^1$ and $R^2$, which may be identical or different, in each case denote a hydrogen, fluorine, chlorine, bromine or iodine atom,
a $C_{1-4}$-alkyl, hydroxy, $C_{1-4}$-alkoxy, $C_{2-3}$-alkenyl or $C_{2-3}$-alkynyl group,
an aryl, aryloxy, arylmethyl or arylmethoxy group,
a heteroaryl, heteroaryloxy, heteroarylmethyl or heteroarylmethoxy group,
a methyl or methoxy group substituted by 1 to 3 fluorine atoms or
a cyano, nitro or amino group, and
$R^3$ denotes a hydrogen, fluorine, chlorine or bromine atom or
a methyl or trifluoromethyl group,
$R^c$ denotes a cyclobutyl, cyclopentyl or cyclohexyl group which is substituted in each case by a group $R^4$—N—$R^5$, while
$R^4$ denotes a hydrogen atom or a $C_{1-3}$-alkyl group and
$R^5$ denotes a hydrogen atom or a $C_{1-3}$-alkyl group,
an aminocarbonyl-$C_{1-3}$-alkyl, $C_{1-3}$-alkylaminocarbonyl-$C_{1-3}$-alkyl, di-($C_{1-3}$-alkyl)aminocarbonyl-$C_{1-3}$-alkyl, pyrrolidin-1-ylcarbonyl-$C_{1-3}$-alkyl, piperidin-1-ylcarbonyl-$C_{1-3}$-alkyl, homopiperidin-1-ylcarbonyl-$C_{1-3}$-alkyl, morpholin-4-ylcarbonyl-$C_{1-3}$-alkyl, homomorpholin-4-ylcarbonyl-$C_{1-3}$-alkyl, piperazin-1-ylcarbonyl-$C_{1-3}$-alkyl, 4-$C_{1-3}$-alkyl-piperazin-1-ylcarbonyl-$C_{1-3}$-alkyl, homopiperazin-1-ylcarbonyl-$C_{1-3}$-alkyl or a 4-$C_{1-3}$-alkyl-homopiperazin-1-ylcarbonyl-$C_{1-3}$-alkyl group,
a hydroxy-$C_{2-4}$-alkyl, $C_{1-3}$-alkyloxy-$C_{2-4}$-alkyl, $C_{1-4}$-alkyloxy-carbonylamino-$C_{2-4}$-alkyl, amino-$C_{2-4}$-alkyl, $C_{1-3}$-alkylamino-$C_{2-4}$-alkyl, di-($C_{1-3}$-alkyl)amino-$C_{2-4}$-alkyl, $C_{1-3}$-alkylcarbonylamino-$C_{2-4}$-alkyl, aminocarbonylamino-$C_{2-4}$-alkyl, $C_{1-3}$-alkylaminocarbonygamino-$C_{2-4}$-alkyl, di-($C_{1-3}$-alkyl)amino-carbonylamino-$C_{2-4}$-alkyl, pyrrolidin-1-ylcarbonylamino-$C_{2-4}$-alkyl, piperidin-1-ylcarbonylamino-$C_{2-4}$-alkyl, morpholin-4-ylcarbonylamino-$C_{2-4}$-alkyl, $C_{1-3}$-alkylsulphonyl-$C_{2-4}$-alkyl or a $C_{1-3}$-alkylsulphonylamino-$C_{2-4}$-alkyl group,
a (2-oxo-pyrrolidin-1-yl)-$C_{2-4}$-alkyl, (2-oxopiperidin-1-yl)-$C_{2-4}$-alkyl, (3-oxo-morpholin-4-yl)-$C_{2-4}$-alkyl, (2-oxo-imidazolidin-1-yl)-$C_{2-4}$-alkyl, (2-oxo-3-$C_{1-3}$-alkyl-imidazolidin-1-yl)-$C_{2-4}$-alkyl, (2-oxo-hexahydropyrimidin-1-yl)-$C_{2-4}$-alkyl or a (2-oxo-3-$C_{1-3}$-alkyl-hexahydropyrimidin-1-yl)-$C_{2-4}$-alkyl group,
a $C_{1-4}$-alkylsulphonyl, chloro-$C_{1-4}$-alkylsulphonyl, bromo-$C_{1-4}$-alkylsulphonyl, amino-$C_{1-4}$-alkylsulphonyl, $C_{1-3}$-alkylamino-$C_{1-4}$-alkylsulphonyl, di-($C_{1-3}$-alkyl)amino-$C_{1-4}$-alkylsulphonyl, (pyrrolidin-1-yl)-$C_{1-4}$-alkylsulphonyl, (piperidin-1-yl)-$C_{1-4}$-alkylsulphonyl, (homopiperidin-1-yl)-$C_{1-4}$-alkylsulphonyl, (morpholin-4-yl)-$C_{1-4}$-alkylsulphonyl, (homomorpholin-4-yl)-$C_{1-4}$-alkylsulphonyl, (piperazin-1-yl)-$C_{1-4}$-alkylsulphonyl, (4-$C_{1-3}$-alkyl-piperazin-1-yl)-$C_{1-4}$-alkylsulphonyl, (homopiperazin-1-yl)-$C_{1-4}$-alkylsulphonyl or a (4-$C_{1-3}$-alkyl-homopiperazin-1-yl)-$C_{1-4}$-alkylsulphonyl group,
a $C_{1-4}$-alkyloxycarbonyl group,
a formyl, $C_{1-4}$-alkyl-carbonyl, $C_{1-3}$-alkyloxy-$C_{1-4}$-alkyl-carbonyl, tetrahydrofuranylcarbonyl, tetrahydropyranylcarbonyl, amino-$C_{1-4}$-alkyl-carbonyl, $C_{1-3}$-alkylamino-$C_{1-4}$-alkyl-carbonyl, di-($C_{1-3}$-alkyl)amino-$C_{1-4}$-alkyl-carbonyl, pyrrolidin-1-yl-$C_{1-4}$-alkyl-carbonyl, piperidin-1-yl-$C_{1-4}$-alkyl-carbonyl, (homopiperidin-1-yl)-$C_{1-4}$-alkyl-carbonyl, morpholin-4-yl-$C_{1-4}$-alkyl-carbonyl, (homomorpholin-4-yl)-$C_{1-4}$-alkyl-carbonyl, (piperazin-1-yl)-$C_{1-4}$-alkyl-carbonyl, (4-$C_{1-3}$-alkyl-piperazin-1-yl)-$C_{1-4}$-alkyl-carbonyl, (homopiperazin-1-yl)-$C_{1-4}$-alkyl-carbonyl, (4-$C_{1-3}$-alkyl-homopiperazin-1-yl)-$C_{1-4}$-alkyl-carbonyl or a $C_{1-3}$-alkylsulphonyl-$C_{1-4}$-alkyl-carbonyl group,
a cyano, aminocarbonyl, $C_{1-3}$-alkyl-aminocarbonyl, di-($C_{1-3}$-alkyl)aminocarbonyl, ($C_{1-3}$-alkyloxy-$C_{2-4}$-alkyl)aminocarbonyl, N-($C_{1-3}$-alkyl)-N-($C_{1-3}$-alkyloxy-$C_{2-4}$-alkyl)aminocarbonyl, arylaminocarbonyl, pyrrolidin-1-ylcarbonyl, piperidin-1-ylcarbonyl, homopiperidin-1-ylcarbonyl, morpholin-4-ylcarbonyl, homomorpholin-4-ylcarbonyl, 2-oxa-5-aza-bicyclo[2.2.1]hept-5-ylcarbonyl, 3-oxa-8-aza-bicyclo[3.2.1]oct-8-ylcarbonyl, 8-oxa-3-aza-bicyclo[3.2.1]oct-3-ylcarbonyl, piperazin-1-ylcarbonyl, 4-$C_{1-3}$-alkyl-piperazin-1-ylcarbonyl, homopiperazin-1-ylcarbonyl, 4-$C_{1-3}$-alkyl-homopiperazin-1-ylcarbonyl, aminosulphonyl, $C_{1-3}$-alkyl-aminosulphonyl, di-($C_{1-3}$-alkyl)amino-sulphonyl, pyrrolidin-1-yl-sulphonyl, piperidin-1-ylsulphonyl, homopiperidin-1-ylsulphonyl, morpholin-4-ylsulphonyl, homomorpholin-4-ylsulphonyl, piperazin-1-ylsulphonyl, 4-$C_{1-3}$-alkyl-piperazin-1-ylsulphonyl, homopiperazin-1-ylsulphonyl or a 4-$C_{1-3}$-alkyl-homopiperazin-1-ylsulphonyl group,
a cyclobutyl, cyclopentyl or cyclohexyl group which is substituted in each case by a group $R^6$, where
$R^6$ denotes a 2-oxo-pyrrolidin-1-yl, 2-oxopiperidin-1-yl, 3-oxo-morpholin-4-yl, 2-oxo-imidazolidin-1-yl, 2-oxo-3-$C_{1-3}$-alkyl-imidazoldin-1-yl, 2-oxo-hexahydropyrimidin-1-yl or a 2-oxo-3-$C_{1-3}$-alkyl-hexahydropyrimidin-1-yl group,
an azetidin-3-yl group which is substituted in the 1 position by the group $R^5$, while $R^5$ is as hereinbefore defined,
a pyrrolidin-3-yl group which is substituted in the 1 position by the group $R^5$, while $R^5$ is as hereinbefore defined,
a piperidin-3-yl group which is substituted in the 1 position by the group $R^5$, while $R^5$ is as hereinbefore defined,
a piperidin-4-yl group which is substituted in the 1 position by the group $R^5$, while $R^5$ is as hereinbefore defined, or a tetrahydrofuran-3-yl, tetrahydropyran-3-yl or tetrahydropyran-4-yl group, $R^d$ denotes a hydrogen atom or a fluorine, chlorine or bromine atom, a hydroxy group, a $C_{1-4}$-alkyloxy group, a methoxy group substituted by 1 to 3 fluorine atoms, an ethyloxy group substituted by 1 to 5 fluorine atoms, a $C_{2-4}$-alkyloxy group which is substituted by a group $R^6$ or $R^7$, while $R^6$ is as hereinbefore defined and $R^7$ denotes a hydroxy, $C_{1-3}$-alkyloxy, $C_{1-3}$-cycloalkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, 2-oxa-5-aza-bicyclo[2.2.1]hept-5-yl, 3-oxa-8-aza-bicyclo[3.2.1]oct-8-yl, 8-oxa-3-aza-bicyclo[3.2.1]oct-3-yl, piperazin-1-yl, 4-$C_{1-3}$-alkyl-piperazin-1-yl, homopiperazin-1-yl or $C_{1-3}$-alkyl-homopiperazin-1-yl group, or a formylamino, $C_{1-3}$-alkylcarbonylamino, $C_{1-3}$-alkyloxy-$C_{1-3}$-alkyl-carbonylamino, $C_{1-4}$-alkyloxycarbonylamino, aminocarbonylamino, $C_{1-3}$-alkylaminocarbonylamino, di-($C_{1-3}$-alkyl) aminocarbonylamino pyrrolidin-1-ylcarbonylamino, piperidin-1-ylcarbonylamino, piperazin-1-ylcarbonylamino, 4-$C_{1-3}$-alkyl-piperazin-1-ylcarbonylamino, morpholin-4-ylcarbonylamino or a $C_{1-4}$-alkylsulphonylamino group, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a $C_{1-4}$-alkoxy group which is substituted by a pyrrolidinyl, piperidinyl or homopiperidinyl group substituted in the 1 position by the group $R^8$, while $R^8$ denotes a hydrogen atom or a $C_{1-3}$-alkyl group, or a $C_{1-4}$-alkoxy group which is substituted by a morpholinyl group substituted in the 4 position by the group $R^8$, while $R^8$ is as hereinbefore defined, and X denotes a nitrogen atom, and by the aryl groups mentioned in the definition of the above groups is meant in each case a phenyl group which is mono- or disubstituted by $R^9$, while the substituents may be identical or different and $R^9$ denotes a hydrogen atom, a fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group, by the heteroaryl groups mentioned in the definition of the above groups is meant a pyridyl, pyridazinyl, pyrimidinyl or pyrazinyl group, while said heteroaryl groups are each mono- or disubstituted by the group $R^9$, while the substituents may be identical or different and $R^9$ is as hereinbefore defined, and said pyrrolidinyl, piperidinyl, piperazinyl and morpholinyl groups may be substituted in each case by one or two $C_{1-3}$-alkyl groups, and unless otherwise stated, said alkyl groups may be straight-chained or branched, with the proviso that the compound 4-[(3-chloro-4-fluoro-phenyl)amino]-6((S)-tetrahydrofuran-3-yloxy)-7-hydroxy-quinazoline is excluded, their tautomers, their stereoisomers, their mixtures and their salts.

2. A bicyclic heterocyclic compound of general formula I according to claim 1, wherein $R^a$ denotes a hydrogen atom, $R^b$ denotes a phenyl group substituted by the groups $R^1$ to $R^3$, while $R^1$ denotes a hydrogen, fluorine, chlorine or bromine atom, a methyl, trifluoromethyl or ethynyl group, a phenyloxy or phenylmethoxy group, while the phenyl moiety of the abovementioned groups is optionally substituted by a fluorine or chlorine atom, or a pyridyloxy or pyridinylmethoxy group, while the pyridinyl moiety of the abovementioned groups is optionally substituted by a methyl or trifluoromethyl group, $R^2$ denotes a hydrogen, fluorine or chlorine atom or a methyl group and $R^3$ denotes a hydrogen atom, $R^c$ denotes a cyclopentyl group which is substituted in the 3 position by a group $R^4$—N—$R^5$, while $R^4$ denotes a hydrogen atom or a $C_{1-3}$-alkyl group and $R^5$ denotes a hydrogen atom or a $C_{1-3}$-alkyl group, an aminocarbonyl-$C_{1-3}$-alkyl, $C_{1-3}$-alkylaminocarbonyl-$C_{1-3}$-alkyl, di-($C_{1-3}$-alkyl)aminocarbonyl-$C_{1-3}$-alkyl, pyrrolidin-1-ylcarbonyl-$C_{1-3}$-alkyl, piperidin-1-ylcarbonyl-$C_{1-3}$-alkyl, piperazin-1-ylcarbonyl-$C_{1-3}$-alkyl, 4-$C_{1-3}$-alkyl-piperazin-1-yl-carbonyl-$C_{1-3}$-alkyl or morpholin-4-ylcarbonyl-$C_{1-3}$-alkyl group, a hydroxy-$C_{2-4}$-alkyl, $C_{1-3}$-alkyloxy-$C_{2-4}$-alkyl, $C_{1-4}$-alkyloxy-carbonylamino-$C_{2-4}$-alkyl, amino-$C_{2-4}$-alkyl, $C_{1-3}$-alkylamino-$C_{2-4}$-alkyl, di-($C_{1-3}$-alkyl)amino-$C_{2-4}$-alkyl, $C_{1-3}$-alkylcarbonylamino-$C_{2-4}$-alkyl, aminocarbonylamino-$C_{2-4}$-alkyl, $C_{1-3}$-alkylaminocarbonylamino-$C_{2-4}$-alkyl, di-($C_{1-3}$-alkyl)amino-carbonylamino-$C_{2-4}$-alkyl, morpholin-4-ylcarbonylamino-$C_{2-4}$-alkyl, $C_{1-3}$-alkylsulphonyl-$C_{2-4}$-alkyl or $C_{1-3}$-alkylsulphonylamino-$C_{2-4}$-alkyl group, a (2-oxo-pyrrolidin-1-yl)-$C_{2-4}$-alkyl, (2-oxopiperidin-1-yl)-$C_{2-4}$-alkyl, (3-oxo-morpholin-4-yl)-$C_{2-4}$-alkyl, (2-oxo-imidazolidin-1-yl)-$C_{2-4}$-alkyl, (2-oxo-3-methyl-imidazolidin-1-yl)-$C_{2-4}$-alkyl, (2-oxo-hexahydropyrimidin-1-yl)-$C_{2-4}$-alkyl or (2-oxo-3-methyl-hexahydropyrimidin-1-yl)-$C_{2-4}$-alkyl group, a $C_{1-3}$-alkylsulphonyl, chloro-$C_{2-4}$-alkylsulphonyl, bromo-$C_{2-4}$-alkylsulphonyl, amino-$C_{2-4}$-alkylsulphonyl, $C_{1-3}$-alkylamino-$C_{2-4}$-alkylsulphonyl, di-($C_{1-3}$-alkyl)amino-$C_{2-4}$-alkylsulphonyl, (pyrrolidin-1-yl)-$C_{2-4}$-alkylsulphonyl, (piperidin-1-yl)-$C_{2-4}$-alkylsulphonyl or (morpholin-4-yl)-$C_{2-4}$-alkylsulphonyl group, a $C_{1-4}$-alkyloxy-carbonyl group, a formyl, $C_{1-3}$-alkyl-carbonyl, $C_{1-3}$-alkyloxy-$C_{1-3}$-alkyl-carbonyl, tetrahydrofuranylcarbonyl, tetrahydropyranylcarbonyl, amino-$C_{1-3}$-alkyl-carbonyl, $C_{1-3}$-alkylamino-$C_{1-3}$-alkyl-carbonyl, di-($C_{1-3}$-alkyl)amino-$C_{1-3}$-alkyl-carbonyl, pyrrolidin-1-yl-$C_{1-3}$-alkyl-carbonyl, piperidin-1-yl-$C_{1-3}$-alkyl-carbonyl, piperazin-1-yl-$C_{1-3}$-alkyl-carbonyl, 4-$C_{1-3}$-alkyl-piperazin-1-yl-$C_{1-3}$-alkyl-carbonyl, morpholin-4-yl-$C_{1-3}$-alkyl-carbonyl or a $C_{1-3}$-alkylsulphonyl-$C_{1-3}$-alkyl-carbonyl group, a cyano, aminocarbonyl, $C_{1-3}$-alkyl-aminocarbonyl, di-($C_{1-3}$-alkyl)aminocarbonyl, ($C_{1-3}$-alkyloxy-$C_{2-4}$- alkyl)aminocarbonyl, N-($C_{1-3}$-alkyl)-N-($C_{1-3}$-alkyloxy-$C_{2-4}$-alkyl)aminocarbonyl, phenylaminocarbonyl, pyrrolidin-1-ylcarbonyl, piperidin-1-ylcarbonyl, morpholin-4-ylcarbonyl, $C_{1-3}$-alkyl-morpholin4-ylcarbonyl, di-($C_{1-3}$-alkyl) morpholin-4-ylcarbonyl, homomorpholin-4-ylcarbonyl, 2-oxa-5-aza-bicyclo[2.2.1]hept-5-ylcarbonyl, 3-oxa-8-aza-bicyclo[3.2.1]oct-8-ylcarbonyl, 8-oxa-3-aza-bicyclo[3.2.1]oct-3-ylcarbonyl, piperazin-1-ylcarbonyl, 4-($C_{1-3}$-alkyl)-piperazin-1-ylcarbonyl, aminosulphonyl, $C_{1-3}$-alkyl-aminosulphonyl, di-($C_{1-3}$-alkyl)amino-sulphonyl, pyrrolidin-1-yl-sulphonyl, piperidin-1-ylsulphonyl or a morpholin-4-ylsulphonyl group, or a cyclopentyl group which is substituted in the 3 position by a group $R^6$, while $R^6$ denotes a 2-oxo-pyrrolidin-1-yl, 2-oxopiperidin-1-yl, 3-oxo-morpholin-4-yl, 2-oxo-imidazolidin-1-yl, 2-oxo-3-methyl-imidazolidin-1-yl, 2-oxo-hexahydropyrimidin-1-yl or a 2-oxo-3-methyl-hexahydropyrimidin-1-yl group, a cyclohexyl group which is substituted in the 3 position or in the 4 position by a group $R^4$—N—$R^5$, while $R^4$ and $R^5$ are as hereinbefore defined, a cyclohexyl group which is substituted in the 3 position or in the 4 position by a group $R^6$, while $R^6$ is as hereinbefore defined, a pyrrolidin-3-yl group which is substituted in the 1 position by the group $R^5$, while $R^5$ is as hereinbefore defined, a piperidin-3-yl group which is substituted in the 1 position by the group $R^5$, while $R^5$ is as hereinbefore defined, a piperidin-4-yl group which is substituted in the 1 position by the group $R^5$, while $R^5$ is as hereinbefore defined, or a tetrahydrofuran-3-yl, tetrahydropyran-3-yl or tetrahydropyran-4-yl group, $R^d$ denotes a hydrogen atom, a $C_{1-3}$-alkyloxy group, a methoxy group which is substituted by one to three fluorine atoms, an ethyloxy group which is substituted in the 2 position by a group $R^6$ or $R^7$, while $R^6$ is as hereinbefore defined and $R^7$ denotes a hydroxy, $C_{1-3}$-alkyloxy, amino, $C_{1-3}$-alkylamino, di-($C_{1-3}$-alkyl)amino, bis-(2-methoxyethyl)-amino pyrrolidin-1-yl, piperidin-1-yl, morpholin-4-yl, homomorpholin-4-yl, 2-oxa-5-aza-bicyclo[2.2.1]hept-5-yl, 3-oxa-8-aza-bicyclo[3.2.1]oct-8-yl, 8-oxa-3-aza-bicyclo[3.2.1]oct-3-yl, piperazin-1-yl or a 4-$C_{1-3}$-alkyl-piperazin-1-yl group, or a formylamino, $C_{1-4}$-alkylcarbonylamino, $C_{1-3}$-alkyloxy-$C_{1-3}$-alkyl-carbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, piperazin-1-ylcarbonylamino, 4-$C_{1-3}$-alkyl-piperazin-1-ylcarbonylamino- morpholin-4-ylcarbonylamino or a $C_{1-4}$-alkylsulphonylamino group, a propyloxy group which is substituted in the 3 position by a group $R^6$ or $R^7$, while $R^6$ and $R^7$ are as hereinbefore defined, or a butyloxy group which is substituted in the 4 position by a group $R^6$ or $R^7$, while $R^6$ and $R^7$ are as hereinbefore defined, and X denotes a nitrogen atom, while, unless stated otherwise, said alkyl groups may be straight-chained or branched, their tautomers, their stereoisomers, their mixtures and their salts.

3. Bicyclic heterocyclic compound of general formula 1 according to claim 1, wherein $R^a$ denotes a hydrogen atom, $R^b$ denotes a 3-ethynylphenyl, 3-bromophenyl, 3,4-difluorophenyl or 3-chloro-4-fluoro-phenyl group, a 3-chloro-4-benzyloxy-phenyl, 3-chloro-4-[(3-fluorobenzyl)oxy]-phenyl, 4-(pyridin-3-yloxy)-phenyl, 4-[(6-methyl-pyridin-3-yl)oxy]-phenyl, 3-methyl-4-(pyridin-3-yloxy)-phenyl, 3-methyl-4-[(6-methyl-pyridin-3-yl)oxy]-phenyl, 3-chloro-4-(pyridin-3-yloxy)-phenyl or 3-chloro-4-[(6-methyl-pyndin-3-yl)oxy]-phenyl group, $R^c$ denotes acyclohexyl group which is substituted in the 3 position or in the 4 position by a group $R^4$—N—$R^5$, while $R^4$ denotes a hydrogen atom, a methyl or ethyl group and $R^5$ denotes a hydrogen atom, a methyl, aminocarbonylmethyl, methylaminocarbonylmethyl, dimethylaminocarbonylmethyl, pyrrolidin-1-ylcarbonylmethyl, piperidin-1-ylcarbonylmethyl, piperazin-1-ylcarbonylmethyl, 4-methylpiperazin-1-ylcarbonylmethyl, morpholin-4-ylcarbonylmethyl, 2-(morpholin-4-yl-carbonyl)ethyl or 3-(morpholin-4-yl-carbonyl)propyl group, an ethyl, propyl, 2-hydroxyethyl, 3-hydroxypropyl, 2-methoxyethyl, 3-methoxypropyl, 2-(butyloxycarbonylamino)-ethyl, 2-aminoethyl, 3-aminopropyl, 2-(acetylamino)ethyl, 3-(acetylamino)propyl, 2-(ethylcarbonylamino)ethyl, 3-(ethylcarbonylamino)propyl, 2-(propylcarbonylamino)ethyl, 3-(propylcarbonylamino)propyl, 2-(ethylaminocarbonylamino)ethyl, 3-(ethylaminocarbonylamino)propyl, 2-(dimethylaminocarbonylamino)ethyl, 3-(dimethylaminocarbonylamino)propyl, 2-(morpholin-4-ylcarbonylamino)ethyl, 3-(morpholin-4-yloarbonylamino)propyl, 2-(methylsulphonyl)ethyl, 3-(methylsulphonyl)propyl, 2-(methylsulphonylamino)ethyl or a 3-(methylsulphonylamino)propyl group, a 2-(2-oxo-pyrrolidin-1-yl)ethyl, 2-(2-oxopiperidin-1-yl)ethyl, 2-(3-oxo-morpholin-4-yl)ethyl, 2-(2-oxo-imidazolidin-1-yl)ethyl, 2-(2-oxo-3-methyl-imidazolidin-1-yl)ethyl, 2-(2-oxo-hexahydropyrimidin-1-yl)ethyl or a 2-(2-oxo-3-methyl-hexahydropyrimidin-1-yl)ethyl group, a 3-(2-oxo-pyrrolidin-1-yl)propyl, 3-(2-oxopiperidin-1-yl)propyl, 3-(3-oxo-morpholin-4-yl)propyl, 3-(2-oxo-imidazolidin-1-yl)propyl, 3-(2-oxo-3-methyl-imidazolidin-1-yl)propyl, 3-(2-oxo-hexahydropyrimidin-1-yl)propyl or a 3-(2-oxo-3-methyl-hexahydropyrimidin-1-yl)propyl group, a methylsulphonyl, ethylsulphonyl, 3-chloropropylsulphonyl, 2-(morpholin-4-yl)-ethylsulphonyl or a 3-(morpholin-4-yl)-propylsulphonyl group, a propyloxycarbonyl or butyloxycarbonyl group, a formyl, acetyl, ethylcarbonyl, propylcarbonyl, methoxyacetyl, (2-methoxyethyl)carbonyl, (3-methoxypropyl)carbonyl, tetrahydrofuran-2-ylcarbonyl, tetrahydropyran-4-ylcarbonyl, aminoacetyl, methylaminoacetyl, dimethylaminoacetyl, morpholin-4-ylacetyl, [2-(morpholin-4-yl)ethyl]carbonyl, [3-(morpholin-4-yl)propyl]carbonyl or a methylsulphonylacetyl group, a cyano, aminocarbonyl, methylaminocarbonyl, dimethylaminocarbonyl, ethylaminocarbonyl, diethylaminocarbonyl, propylaminocarbonyl, (2-methoxyethyl)aminocarbonyl, N-methyl-N-(2-methoxyethyl)-aminocarbonyl, (3-methoxypropyl) aminocarbonyl, N-methyl-N-(3-methoxypropyl)-aminocarbonyl, phenylaminocarbonyl, pyrrolidin-1-ylcarbonyl, piperidin-1-ylcarbonyl, morpholin-4-ylcarbonyl, 2-methylmorpholin-4-ylcarbonyl, 2,6-dimethylmorpholin-4-ylcarbonyl, homomorpholin-4-ylcarbonyl, 2-oxa-5-aza-bicyclo[2.2.1]hept-5-ylcarbonyl, 3-oxa-8-aza-bicyclo[3.2.1]oct-8-ylcarbonyl, 8-oxa-3-aza-bicyclo[3.2.1]oct-3-ylcarbonyl, 4-methylplperazin-1-ylcarbonyl, aminosulphonyl, methylaminosulphonyl, dimethylaminosulphonyl or a morpholin-4-ylsulphonyl group, a cyclohexyl group which is substituted in the 3 position or in the 4 position by a group $R^6$, while $R^6$ denotes a 2-oxo-pyrrolidin-1-yl, 2-oxopiperidin-1-yl, 3-oxo-morpholin-4-yl, 2-oxo-imidazolidin-1-yl, 2-oxo-3-methyl-imidazolidin-1-yl, 2-oxo-hexahydropyrimidin-1-yl or a 2-oxo-3-methyl-hexahydropyrimidin-1-yl group, a pyrrolidin-3-yl group which is substituted in the 1 position by the group $R^5$, while $R^5$ is as hereinbefore defined, a piperidin-3-yl group which is substituted in the 1 position by the group $R^5$, while $R^5$ is as hereinbefore defined, a piperidin-4-yl group which is substituted in the 1 position by the group $R^5$, while $R^5$ is as hereinbefore defined, a tetrahydrofuran-3-yl, tetrahydropyran-3-yl or tetrahydropyran-4-yl group, $R^d$ denotes a hydrogen atom, a methoxy, difluoromethoxy or ethyloxy group, an ethyloxy group which is substituted in the 2 position by a group $R^6$ or $R^7$, while $R^6$ is as hereinbefore defined and $R^7$ denotes a hydroxy, methoxy, ethoxy, amino, dimethylamino, diethylamino, bis-(2-methoxyethyl)-amino, pyrrolidin-1-yl, piperidin-1-yl, morpholin-4-yl, homomorpholin-4-yl, 2-oxa-5-aza-bicyclo[2.2.1]hept-5-yl, 3-oxa-8-aza-bicyclo[3.2.1]oct-8-yl, 8-oxa-3-aza-bicyclo[3.2.1]oct-3-yl, piperazin-1-yl, 4-methylpiperazin-1-yl or 4-ethylpiperazin-1-yl group, or an acetylamino, ethylcarbonylamino, propylcarbonylamino, butylcarbonylamino, methoxyacetylamino, butyloxycarbonylamino, ethylaminocarbonylamino, dimethylaminocarbonylamino, pyrrolidin-1-ylcarbonylamino, piperidin-1-ylcarbonylamino, morpholin-4-ylcarbonylamino, methylsulphonylamino, ethylsulphonylamino or butylsulphonylamino group, a propyloxy group which is substituted in the 3 position by a group $R^6$ or $R^7$, while $R^6$ and $R^7$ are as hereinbefore defined, or a butyloxy group which is substituted in the 4 position by a group $R^6$ or $R^7$, while $R^6$ and $R^7$ are as hereinbefore defined, and X denotes a nitrogen atom, while, unless stated otherwise, said alkyl groups may be straight-chained or branched, their tautomers, their stereoisomers, their mixtures and their salts.

4. A bicyclic heterocyclic compound of general formula I according to claim 1, wherein $R^a$ denotes a hydrogen atom, $R^b$ denotes a 3-bromophenyl, 3,4-difluorophenyl, 3-chloro-4-fluoro-phenyl or a 3-ethynylphenyl group, or a 3-chloro-4-benzyloxy-phenyl, 3-chloro-4-[(3-fluorbenzyl)oxy]-phenyl, 4-(pyridin-3-yloxy)-phenyl, 4-[(6-methyl-pyridin-3-yl)oxy]-phenyl, 3-methyl-4-(pyridin-3-yloxy)-phenyl, 3-methyl-4-[(6-methyl-pyridin-3-yl)oxy]-phenyl, 3-chloro-4-(pyridin-3-yloxy)-phenyl or 3-chloro-4-[(6-methyl-pyridin-3-yl)oxy]-phenyl group, $R^c$ denotes a cyclohexyl group which is substituted in the 3 position by an amino, acetylamino, tert.-butyloxycarbonylamino or methylsulphonylamino group, a cyclohexyl group which is substituted in the 4 position by an amino, methylamino, ethylamino, dimethylamino, aminocarbonylmethylamino, methylaminocarbonylmethylamino, dimethylaminocarbonylmethylamino, morpholin-4-ylcarbonylmethylamino, [3-(morpholin-4-ylcarbonyl)propyl]amino, [2-(methylsulphonyl)ethyl]amino, [3-(methylsulphonyl)propyl]amino or [2-(methylsulphonylamino)ethyl]amino group, a cyclohexyl group which is substituted in the 4 position by a [2-(2-oxo-pyrrolidin-1-yl)ethyl]amino, [2-(2-oxopiperidin-1-yl)ethyl]amino, [2-(2-oxo-imidazolidin-1-yl)ethyl]amino, [2-(2-oxo-3-methyl-imidazolidin-1-yl)ethyl]amino, [2-(2-oxo-hexahydropyrimidin-1-yl)ethyl]amino or [2-(2-oxo-3-methyl-hexahydropyrimidin-1-yl)ethyl]amino group, a cyclohexyl group which is substituted in the 4 position by a [3-(2-oxo-pyrrolidin-1-yl)propyl]amino, [3-(2-oxopiperidin-1-yl)propyl]amino, [3-(2-oxo-imidazolidin-1-yl)propyl]amino, [3-(2-oxo-3-methyl-imidazolidin-1-yl)propyl]amino, [3-(2-oxo-hexahydropyrimidin-1-yl)propyl]amino or [3-(2-oxo-3-methyl-hexahydropyrimidin1-yl)propyl]amino group, a cyclohexyl group which is substituted in the 4 position by an acetylamino, N-(acetyl)-methylamino, aminomethylcarbonylamino, methylaminomethylcarbonylamino, dimethylaminomethylcarbonylamino, morpholin-4-ylmethylcarbonylamino, methoxyacetylamino, N-(methoxyacetyl)-methylamino, tetrahydropyran-4-ylcarbonylamino N-(tetrahydropyran-4-ylcarbonyl)-methylamino, tert.-butyloxycarbonylamino, N-(tert.-butyloxycarbonyl)-methylamino, aminocarbonylamino, methylaminocarbonylamino, N-(ethylaminocarbonyl)methylamino, dimethylaminocarbonylamino, N-(dimethylaminocarbonyl)methylamino N-(piperidin-1-ylcarbonyl)-methylamino, morpholin-4-ylcarbonylamino, N-(morpholin-4-ylcarbonyl)methylamino or N-(4-methylpiperazin-1-ylcarbonyl)-methylamino group, a cyclohexyl group which is substituted in the 4 position by a 2-oxo-pyrrolidin-1-yl, 2-oxopiperidin-1-yl, 3-oxomorpholin-4-yl, 2-oxo-imidazolidin-1-yl, 2-oxo-3-methyl-imidazolidin-1-yl, 2-oxo-hexahydropyrimidin-1-yl or a 2-oxo-3-methyl-hexahydropyrimidin-1-yl group, a cyclohexyl group which is substituted in the 4 position by a methylsulphonylamino, N-(methylsulphonyl)-methylamino, ethylsulphonylamino, N-(ethylsulphonyl)-methylamino, dimethylaminosulphonylamino, N-(dimethylaminosulphonyl)-methylamino, morpholin-4-ylsulphonylamino, N-(morpholin-4-ylsulphonyl)-methylamino-3-chloropropylsulphonylamino, [2-(morpholin-4-yl)-ethyl]sulphonylamino or [3-(morpholin-4-yl)-propyl]sulphonylamino- group, a pyrrolidin-3-yl group, a pyrrolidin-3-yl group which is substituted in the 1 position by a methyl, acetyl, methoxyacetyl, tert.-butyloxycarbonyl, morpholin-4-ylcarbonyl or methyl-sulphonyl group, a piperidin-3-yl group, a piperidin-3-yl group which is substituted in the 1 position by a methyl, acetyl, methoxyacetyl, tert.-butyloxycarbonyl, morpholin-4-ylcarbonyl or methyl-sulphonyl group, a piperidin-4-yl group which is substituted in the 1 position by a methyl, ethyl, propyl, isopropyl, 2-hydroxyethyl, 2-methoxyethyl, 3-methoxypropyl, 2-(methylsulphonyl)-ethyl, 3-(methylsulphonyl)-propyl, 2-(tert.-butyloxycarbonylamino)-ethyl, 2-aminoethyl, 2-(acetylamino)-ethyl, 2-(ethylcarbonylamino)-ethyl, 2-(propylcarbonylamino)-ethyl, 2-(ethylaminocarbonylamino)-ethyl, 2-(dimethylaminocarbonylamino)-ethyl, 2-(morpholin-4-ylcarbonylamino)-ethyl, 3-(acetylamino)-propyl, 3-(ethylcarbonylamino)-propyl, 3-(propylcarbonylamino)-propyl, 3-(ethylaminocarbonylamino)-propyl, 3-(dimethylaminocarbonylamino)-propyl, 3-(morpholin-4-ylcarbonylamino)-propyl, 2-(methylsulphonylamino)-ethyl, 3-(methylsulphonylamino)-propyl, (aminocarbonyl)methyl, (methylaminocarbonyl)methyl, (dimethylaminocarbonyl)methyl, (pyrrolidin-1-ylcarbonyl)methyl, (morpholin-4-ylcarbonyl)methyl, 2-(morpholin-4-ylcarbonyl)-ethyl or 3-(morpholin-4-ylcarbonyl)-propyl group, a piperidin-4-yl group which is substituted in the 1 position by a 2-(2-oxo-pyrrolidin-1-yl)-ethyl, 2-(2-oxopiperidin-1-yl)-ethyl, 2-(3-oxomorpholin-4-yl)-ethyl, 2-(2-oxo-imidazolidin-1-yl)-ethyl, 2-(2-oxo-3-methyl-imidazolidin-1-yl)-ethyl, 2-(2-oxo-hexahydropyrimidin-1-yl)-ethyl or 2-(2-oxo-3-methyl-hexahydropyrimidin-1-yl)-ethyl group, a piperidin-4-yl group which is substituted in the 1 position by a 3-(2-oxo-pyrrolidin-1-yl)-propyl, 3-(2-oxopiperidin-1-yl)-propyl, 3-(3-oxomorpholin-4-yl)-propyl, 3-(2-oxo-imidazolidin-1-yl)-propyl, 3-(2-oxo-3-methyl-imidazolidin-1-yl)-propyl, 3-(2-oxo-hexahydropyrimidin-1-yl)-propyl or 3-(2-oxo-3-methyl-hexahydropyrimidin-1-yl)-propyl group, a piperidin-4-yl group which is substituted in the 1 position by a formyl, acetyl, methoxyacetyl, (2-methoxyethyl)carbonyl, (3-methoxypropyl)carbonyl, methylsulphonylacetyl, aminoacetyl, methylaminoacetyl, (dimethylamino)acetyl, (morpholin-4-yl)acetyl, [2-(morpholin-4-yl)-ethyl]carbonyl, [3-(morpholin-4-yl)-propyl]carbonyl, tetrahydrofuran-2-ylcarbonyl or tetrahydropyran-4-ylcarbonyl group, a piperidin-4-yl group which is substituted in the 1 position by a cyano, aminocarbonyl, methylaminocarbonyl, ethylaminocarbonyl, (2-methoxyethyl)aminocarbonyl, N-methyl-N-(2-methoxyethyl)-aminocarbonyl, (3-methoxypropyl)aminocarbonyl, N-methyl-N-(3-methoxypropyl)-aminocarbonyl, isopropylaminocarbonyl, phenylaminocarbonyl, dimethylaminocarbonyl, diethylaminocarbonyl, pyrrolidin-1-ylcarbonyl, piperidin-1-ylcarbonyl, morpholin-4-ylcarbonyl, 2-methylmorpholin-4-ylcarbonyl, 2,6-dirnethylmorpholin-4-ylcarbonyl, homomorpholin-4-ylcarbonyl, 2-oxa-5-aza-bicyclo[2.2.1]hept-5-ylcarbonyl, 3-oxa-8-aza-bicyclo[3.2.1]oct-8-ylcarbonyl, 8-oxa-3-aza-bicyclo[3.2.1]oct-3-ylcarbonyl, 4-methylpiperazin-1-ylcarbonyl, isopropyloxycarbonyl or tert.-butyloxycarbonyl group, a piperidin-4-yl group which is substituted in the 1 position by a methylsulphonyl, ethylsulphonyl, [2-(morpholin-4-yl)-ethyl]sulphonyl, [3-(morpholin-4-yl)-propyl]sulphonyl, aminosulphonyl, methylaminosulphonyl, dimethylaminosulphonyl or morpholin-4-ylsulphonyl group, or a tetrahydrofuran-3-yl, tetrahydropyran-3-yl or tetrahydropyran-4-yl group, $R^d$ denotes a hydrogen atom, a methoxy, difluoromethoxy or ethyloxy group, a 2(morpholin-4-yl)ethyloxy, 3-(morpholin-4-yl)propyloxy or 4-(morpholin-4-yl)butyloxy group, a 3-(dimethylamino)propyloxy, 3-(diethylamino)propyloxy, 3-[bis-(2-methoxyethyl)-amino]propyloxy, 3-(piperazin-1-yl)propyloxy, 3-(4-methylpiperazin-1-yl)propyloxy or 3-(4-ethylpiperazin-1-yl)propyloxy group, a 3-(homomorpholin-4-yl)-propyloxy, 3-(2-oxa-5-aza-bicyclo[2.2.1]hept-5-yl)-propyloxy, 3-(3-oxa-8-aza-bicyclo[3.2.1]oct8-yl)-propyloxy or 3-(8-oxa-3-aza-bicyclo[3.2.1]oct-3-yl)-propyloxy group, a 2-(2-oxo-pyrrolidin-1-yl)-ethyloxy, 2-(2-oxopiperidin-1-yl)-ethyloxy, 2-(3-oxomorpholin-4-yl)-ethyloxy, 2-(2-oxo-imidazolidin-1-yl)-ethyloxy, 2-(2-oxo-3-methyl-imidazolidin-1-yl)-ethyloxy, 2-(2-oxo-hexahydropyrimidin-1-yl)-ethyloxy or 2-(2-oxo-3-methyl-hexahydropyrimidin-1-yl)-ethyloxy group, a 3-(2-oxo-pyrrolidin-1-yl)-propyloxy, 3-(2-oxopiperidin-1-yl)-propyloxy, 3-(3-oxomorpholin-4-yl)-propyloxy, 3-(2-oxo-imidazolidin-1-yl)-propyloxy, 3-(2-oxo-3-methyl-imidazolidin-1-yl)-propyloxy, 3-(2-oxo-hexahydropyrimidin-1-yl)-propyloxy or 3-(2-oxo-3-methyl-hexahydropyrimidin-1-yl)-propyloxy group, a 2-(methoxy)-ethyloxy, 2-(tert.-butyloxycarbonylamino)-ethyloxy 2-(amino)-ethyloxy, 2-(acetylamino)-ethyloxy, 2-(ethylcarbonylamino)- ethyloxy, 2-(propylcarbonylamino)-ethyloxy, 2-(isobutylcarbonylamino)-ethyloxy, 2-(methoxyacetylamino)-ethyloxy, 2-(ethylaminocarbonylamino)-ethyloxy-, 2-(dimethylaminocarbonylamino)-ethyloxy, 2-(pyrrolidin-1-ylcarbonylamino)-ethyloxy, 2-(piperidin-1-ylcarbonylamino)-ethyloxy, 2-(morpholin-4-ylcarbonylamino)-ethyloxy, 2-(methylsulphonylamino)-ethyloxy group, 2-(ethylsulphonylamino)-ethyloxy or 2-(butylsulphonylamino)-ethyloxy group, or a 3-(tert.-butyloxycarbonylamino)propyloxy, 3-(amino)-propyloxy, 3-(acetylamino)-propyloxy or 3-(methylsulphonylamino)-propyloxy group, and X denotes a nitrogen atom, their tautomers, their stereoisomers, their mixtures and their salts.

5. A bicyclic heterocyclic compound of general formula I according to claim 1, wherein $R^a$ denotes a hydrogen atom, $R^b$ denotes a 3-chloro-4-fluoro-phenyl group or a 3-ethynylphenyl group, $R^c$ denotes a cyclohexyl group which is substituted in the 3 position by an amino, acetylamino, tert.-butyloxycarbonylamino or methylsulphonylamino group, a cyclohexyl group which is substituted in the 4 position by an amino, methylamino, dimethylamino, acetylamino, N-(acetyl)-methylamino, methoxyacetylamino, N-(methoxyacetyl)-methylamino tetrahydropyran-4-ylcarbonylamino, N-(tetrahydropyran-4-ylcarbonyl)methylamino, tert.-butyloxycarbonylamino, N-(tert.-butyloxycarbonyl) methylamino, N-(ethylaminocarbonyl)-methylamino, dimethylaminocarbonylamino, N-(dimethylaminocarbonyl)-methylamino, N-(piperidin-1-ylcarbonyl)-methylamino, morpholin-4-ylcarbonylamino, N-(morpholin-4-ylcarbonyl)-methylamino, N-(4-methylpiperazin-1-ylcarbonyl)-methylamino, methylsulphonylamino, N-(methylsulphonyl)-methylamino, ethylsulphonylamino, N-(ethylsulphonyl)-methylamino, dimethylaminosulphonylamino, N-(dimethylaminosulphonyl)-methylamino, morpholin-4-ylsulphonylamino, N-(morpholin-4-ylsulphonyl)methylamino, 3-chloropropylsulphonylamino, or [3-(morpholin-4-yl)-propyl]sulphonylamino group, a pyrrolidin-3-yl group, a pyrrolidin-3-yl group which is substituted in the 1 position by a tert.-butyloxycarbonyl or methylsulphonyl group, a piperidin-3-yl group, a piperidin-3-yl group which is substituted in the 1 position by a tert.-butyloxycarbonyl or methylsulphonyl group, a piperidin-4-yl group, a piperidin-4-yl group which is substituted in the 1 position by a methyl, (aminocarbonyl)methyl, (dimethylaminocarbonyl)methyl, (morpholin-4-ylcarbonyl)methyl, 2-(tert.-butyloxycarbonylamino) ethyl, 2-aminoethyl, 2-(acetylamino)ethyl, 2-(methylsulphonylamino)ethyl, cyano, acetyl, methoxyacetyl, (dimethylamino)acetyl, (morphoiin-4-yl)acetyl, tetrahydropyran-4-ylcarbonyl, ethylaminocarbonyl, isopropylaminocarbonyl, phenylaminocarbonyl, dimethylaminocarbonyl, diethylaminocarbonyl, pyrrolidin-1-ylcarbonyl, piperidin-1-ylcarbonyl, morpholin-4-ylcarbonyl, 2-methylmorpholin-4-ylcarbonyl, 2,6-dimethylmorpholin-4-ylcarbonyl, homomorpholin-4-ylcarbonyl, 4-methylpiperazin-1-ylcarbonyl, isopropyloxycarbonyl, tert.-butyloxycarbonyl, methylsulphonyl, dimethylaminosulphonyl or morpholin-4-ylsulphonyl group, or a tetrahydrofuran-3-yl, tetrahydropyran-3-yl or tetrahydropyran-4-yl group, $R^d$ denotes a hydrogen atom, a methoxy or ethyloxy group, a 2-(morphoiin-4-yl)ethyloxy, 3-(morpholin-4-yl) propyloxy or 4-(morpholin-4-yl)butyloxy group, a 2-(3-methyl-2-oxo-hexahydropyrimidin-1-yl)-ethyloxy group, a 2-(methoxy)-ethyloxy, 2-(tert.-butyloxycarbonylamino) ethyloxy 2-amino-ethyloxy, 2-(acetylamino)-ethyloxy or 2-(methylsulphonylamino)-ethyloxy group or a 3-(tert.-butyloxycarbonylamino)-propyloxy, 3-amino-propyloxy, 3-(acetylamino)-propyloxy or 3-(methylsulphonylamino)-propyloxy group, and X denotes a nitrogen atom, their tautomers, their stereoisomers, their mixtures and their salts.

6. The following compounds of general formula I according to claim 1:

(a) 4-[(3-chloro-4-fluoro-phenyl)amino]-6-((S)-tetrahydrofuran-3-yloxy)-7-methoxy-quinazoline, (b) 4-[(3-chloro-4-fluoro-phenyl)amino]-6-(tetrahydropyran-4-yloxy)-7-methoxy-quinazoline, (c) 4-[(3-chloro-4-fluoro-phenyl)amino]-6-((R)-tetrahydrofuran-3-yloxy)-7-methoxy-quinazoline, (d) 4-[(3-chloro-4-fluoro-phenyl)amino]-6-(trans-4-amino-cyclohexan-1-yloxy)-7-methoxy-quinazoline, (e) 4-[(3-chloro-4-fluoro-phenyl)amino]-6-(trans-4-methanesulphonylamino-cyclohexan-1-yloxy)-7-methoxy-quinazoline, (f) 4-[(3-chloro-4-fluoro-phenyl)amino]-6-(piperidin-4-yloxy)-7-methoxy-quinazoline, (g) 4-[(3-chloro-4-fluoro-phenyl)amino]-6-(1-methanesulphonyl-piperidin-4-yloxy)-7-methoxy-quinazoline, (h) 4-[(3-chloro-4-fluoro-phenyl)amino]-6-(cis-4-{[3-(morpholin-4-yl)-propyl]sulphonylamino}-cyclohexan-1-yloxy)-7-methoxy-quinazoline, (i) 4-[(3-chloro-4-fluoro-phenyl)amino]-6-(tetrahydropyran-3-yloxy)-7-methoxy-quinazoline, (k) 4-[(3-chloro-4-fluoro-phenyl)amino]-6-(trans-4-{[3-(morpholin-4-yl)-propyl]sulphonylamino)-cyclohexan-1-yloxy)-7-methoxy-quinazoline, (l) 4-[(3-chloro-4-fluoro-phenyl)amino]-6-(1-methyl-piperidin-4-yloxy)-7-methoxy-quinazoline, (m) 4-[(3-chloro-4-fluoro-phenyl)amino]-6-{1-[(morpholin-4-yl)carbonyl]-piperidin-4-yloxy}-7-methoxy-quinazoline, (n) 4-[(3-chloro-4-fluoro-phenyl)amino]-6-{1-[(methoxymethyl)carbonyl]-piperidin-4-yloxy}-7-methoxy-quinazoline, (o) 4-[(3-chloro-4-fluoro-phenyl)amino]-6-(1-cyano-piperidin-4-yloxy)7-methoxy-quinazoline, (p) 4-[(3-chloro-4-fluoro-phenyl)amino]-6-{1-[(morpholin-4-yl)sulphonyl]-piperidin-4-yloxy}-7-methoxy-quinazoline, (q) 4-[(3-chloro-4-fluoro-phenyl)amino]-6-[1-(2-acetylamino-ethyl)-piperidin-4-yloxy]-7-methoxy-quinazoline, (r) 4-[(3-chloro-4-fluoro-phenyl)amino]-6-{trans-4-[(dimethylamino)sulphonylamino-cyclohexan-1-yloxy}-7-methoxy-quinazoline, (s) 4-[(3-chloro-4-fluoro-phenyl)amino]-6-{trans-4-[(morpholin-4-yl)carbonylamino]-cyclohexan-1-yloxy}-7-methoxy-quinazoline, (t) 4-[(3-chloro-4-fluoro-phenyl)amino]-6-{trans-4-[(morpholin-4-yl)sulphonylamino-cyclohexan-1-yloxy)-7-methoxy-quinazoline, (u) 4-[(3-chloro-4-fluoro-phenyl)amino]-6-(tetrahydropyran-4-yloxy)-7-(2-acetylamino-ethoxy)-quinazoline, (v) 4-[(3-chloro-4-fluoro-phenyl)amino]-6-(tetrahydropyran-4-yloxy)-7-(2-methanesulphonylamino-ethoxy)-quinazoline and (w) 4-[(3-chloro-4-fluoro-phenyl)amino]-6-(tetrahydropyran-4-yloxy)-7-(2-methoxy-ethoxy)-quinazoline, and the salts thereof.

7. Physiologically acceptable salts of the compounds according to claim 1 with inorganic or organic acids or bases.

8. Pharmaceutical compositions containing a compound according to claim 1.

9. Pharmaceutical compositions containing a compound according to claim 7 optionally together with one or more inert carrier and/or diluents.

* * * * *